(12) United States Patent
Bourrier et al.

(10) Patent No.: US 9,024,022 B2
(45) Date of Patent: May 5, 2015

(54) SUBSTRATES OF O6-ALKYLGUANINE-DNA ALKYLTRANSFERASE AND MUTANTS THEREOF

(75) Inventors: Emmanuel Bourrier, Bagnols sur Cèze (FR); Michel Laget, Carsan (FR); Laurent Lamarque, Saint Victor la Coste (FR); Norbert Tinel, Lunel-Viel (FR); Eric Trinquet, Pont Saint Esprit (FR); Hervé Bazin, Villeneuve les Avignon (FR)

(73) Assignee: Cis Bio International, Gif Sur Yvette Cedex (FR)

( * ) Notice: Subject to any disclaimer, the term of this patent is extended or adjusted under 35 U.S.C. 154(b) by 803 days.

(21) Appl. No.: 13/120,197

(22) PCT Filed: Sep. 22, 2009

(86) PCT No.: PCT/FR2009/051787
§ 371 (c)(1),
(2), (4) Date: Jun. 13, 2011

(87) PCT Pub. No.: WO2010/034931
PCT Pub. Date: Apr. 1, 2010

(65) Prior Publication Data
US 2011/0236952 A1    Sep. 29, 2011

(30) Foreign Application Priority Data
Sep. 23, 2008  (FR) ..................... 08 56409

(51) Int. Cl.
| C07D 473/18 | (2006.01) |
| C07D 239/47 | (2006.01) |
| C07D 403/14 | (2006.01) |
| C07D 487/18 | (2006.01) |
| C07D 519/00 | (2006.01) |

(52) U.S. Cl.
CPC ............ *C07D 239/47* (2013.01); *C07D 403/14* (2013.01); *C07D 473/18* (2013.01); *C07D 487/18* (2013.01); *C07D 519/00* (2013.01)

(58) Field of Classification Search
CPC ............................. C07D 413/18; C07D 239/47
USPC .................................................. 544/276, 317
See application file for complete search history.

(56) References Cited

U.S. PATENT DOCUMENTS

| 2006/0024775 A1 | 2/2006 | Kindermann et al. |
| 2009/0186373 A1 | 7/2009 | Kindermann et al. |

FOREIGN PATENT DOCUMENTS

| EP | 1882688 A1 | 1/2008 |
| WO | 02083937 A2 | 10/2002 |
| WO | 2004031405 A | 4/2004 |
| WO | 2006114409 A1 | 11/2006 |

OTHER PUBLICATIONS

International Search Report, dated Feb. 2, 2010, issued in corresponding PCT/FR2009/051787.

*Primary Examiner* — Golam M M Shameem
*Assistant Examiner* — Laura Daniel
(74) *Attorney, Agent, or Firm* — Millen, White, Zelano, Branigan, P.C.

(57) ABSTRACT

The invention relates to compounds of formula (I'):

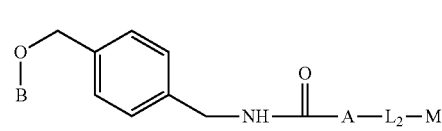

(I')

Figure 2:
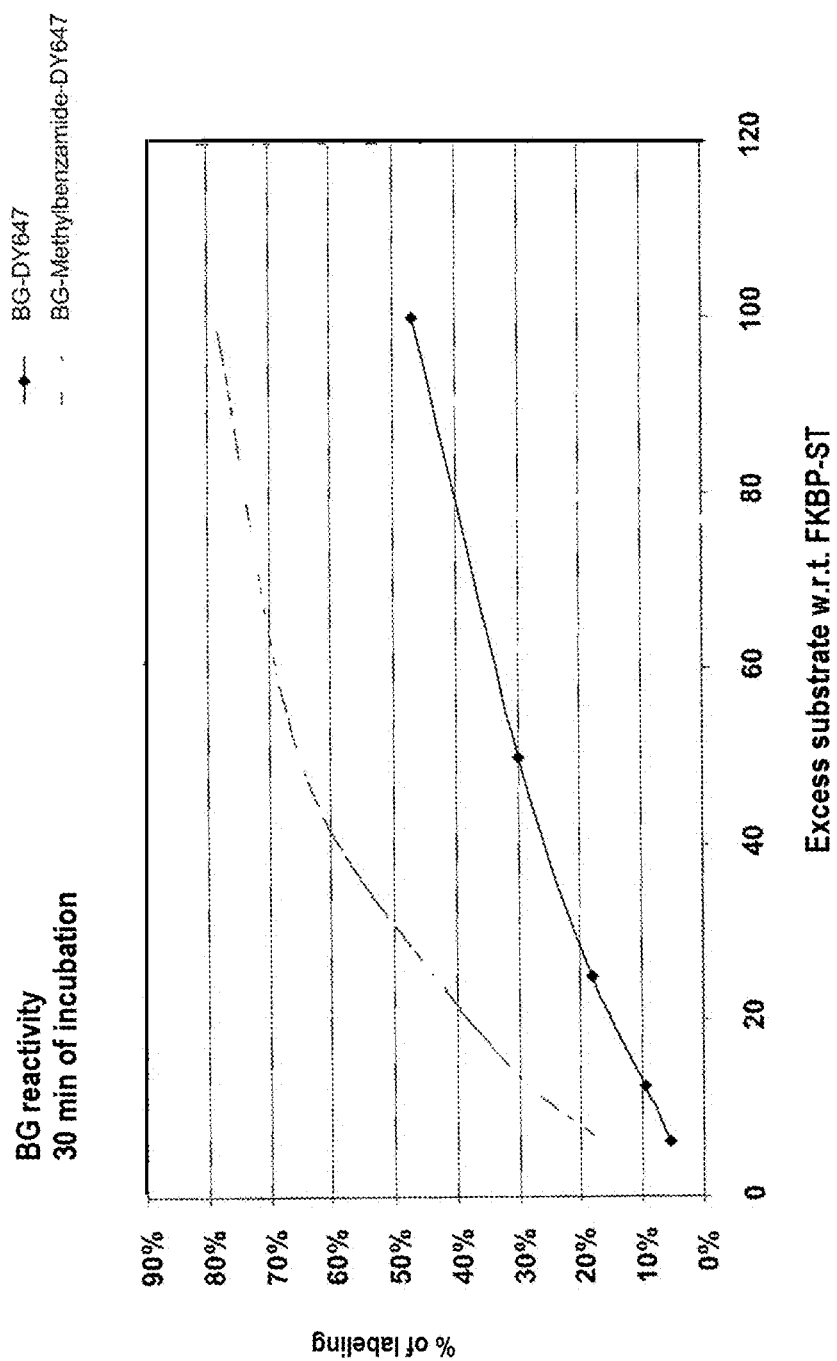

in which A, L2, M and B are as defined in the description. These compounds are substrates of O6-alkylguanine-DNA alkyltransferase and mutants thereof.

17 Claims, 13 Drawing Sheets

FIGURE 1A
Fluorophore
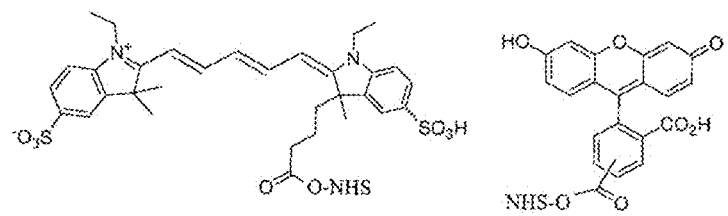
DY647
5,6-carboxyfluorescein
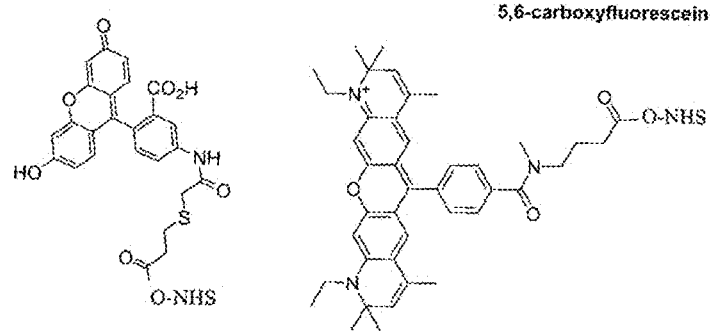
Fluorescein-5-EX
ATTO647N
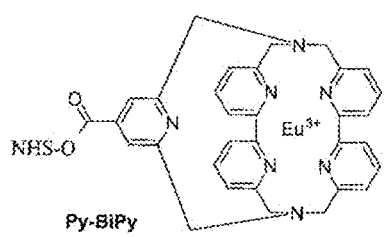
Py-BiPy
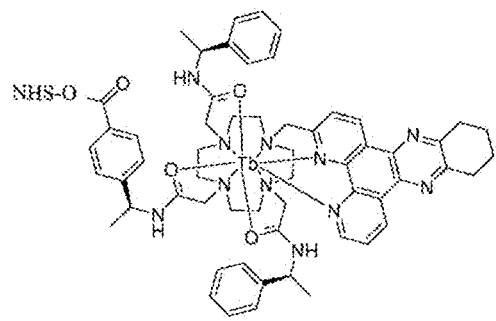
DOTA-TATP-Tb
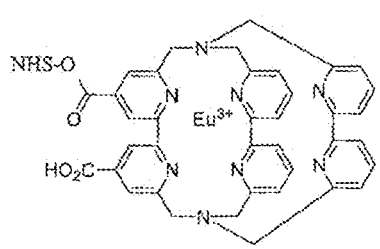
TrisBiPy-Eu

FIGURE 1B
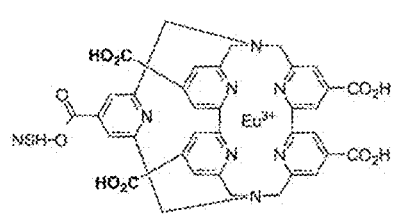
K-Py-BiPy-tetraacid-Eu
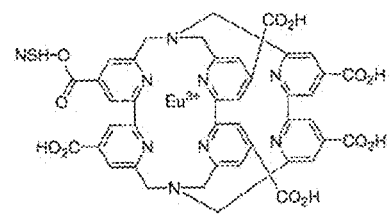
K-TrisBiPy-pentaacid-Eu
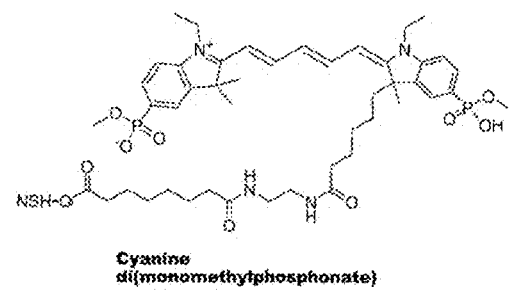
Cyanine di(monomethylphosphonate)
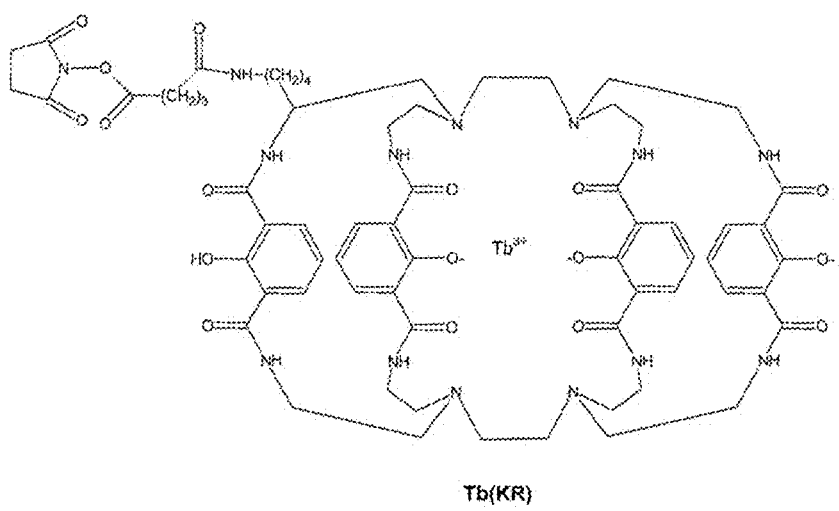
Tb(KR)

SUBSTRATES OF O6-ALKYLGUANINE-DNA ALKYLTRANSFERASE AND MUTANTS THEREOF

PRIOR ART

The mutagenic and carcinogenic effects of electrophilic compounds such as N-methyl-N-nitrosourea are for the main part due to the $O^6$-alkylation of the guanine residues of DNA. Mechanisms for protection against this alkylation of DNA exist in mammals and bacteria, and $O^6$-alkylguanine-DNA alkyltransferase (AGT) in particular is capable of repairing these lesions. AGT transfers the alkyl group at position $O^6$ of the alkylated guanine to a thiol group of one of its own cysteines, which leads to an irreversible alkylation of AGT. This group transfer takes place via a nucleophilic substitution of type 2, which explains why the transfer of benzyl groups is also possible, in addition to the transfer of alkyl groups.

Insofar as the overexpression of AGT in the tumor cells is the main reason for the resistance to medicaments whose action is based on the alkylation of DNA, such as procarbazine, dacarbazine, temozolomide and bis(2-chloroethyl)-N-nitrosourea, the use of inhibitors of AGT was proposed as a sensitizing agent within the context of chemotherapeutic treatments (Pegg et al., Prog Nucleic Acid Res Mol Biol 51:167-223, 1995). U.S. Pat. No. 5,691,307 describes derivatives of $O^6$-benzylguanine bearing various substituents on the benzyl group, and also the use thereof for reducing the levels of AGT in tumor cells and for thus increasing their sensitivity to treatments based on the use of alkylating agents. Similarly, patent application WO 97/20843 discloses other compounds for this use, in the form of derivatives of $O^6$-benzyl and $O^6$-heteroarylmethylpyrimidine.

Pat. DE 199 03 895 discloses an assay for AGT based on the reaction between biotinylated derivatives of $O^6$-alkylguanine and AGT, resulting in the biotinylation of AGT, which enables its separation on plates covered with streptavidin and its detection, for example by an ELISA assay. This technique is proposed in order to monitor the levels of AGT in cancerous tissues, and also in order to highlight inhibitors of AGT.

WO 01/85221 proposes to use fluoro or iodo radioactive derivatives of $O^6$-benzylguanine in order to detect AGT.

Damoiseaux et al., ChemBiochem. 4:285-287, 2001 disclose derivatives of $O^6$-alkylguanine incorporated into oligodeoxyribonucleotides and their use as probes intended to label AGT, once again for the purpose of measuring the expression levels of this enzyme in cancerous cells in order to improve the effectiveness of chemotherapy treatments.

Application WO 02/083937 describes a method for detecting and manipulating a protein of interest fused to the AGT, which consists in bringing this fusion protein into contact with an AGT substrate bearing a label, which makes it possible, after transfer of the molecule of interest to the AGT, to detect or manipulate this protein of interest. This application also discloses various fusion proteins comprising AGT, the general principles relating to the structure of the AGT substrates, and also a variety of labels and methods for detecting said label.

Application WO 2004/031404 describes particular fusion proteins comprising AGT and a protein of interest that are capable of being used in the method described previously, labeled fusion proteins obtained by this method and a method using said fusion proteins.

Applications WO 2004/031405 and WO 2005/085470 describe particular AGT substrates bearing one or more labels and also their manufacturing processes, these substrates being capable of being used in the method described in WO 02/083937.

Examples of AGT substrates are the derivatives of benzylguanine and benzylcytosine below:

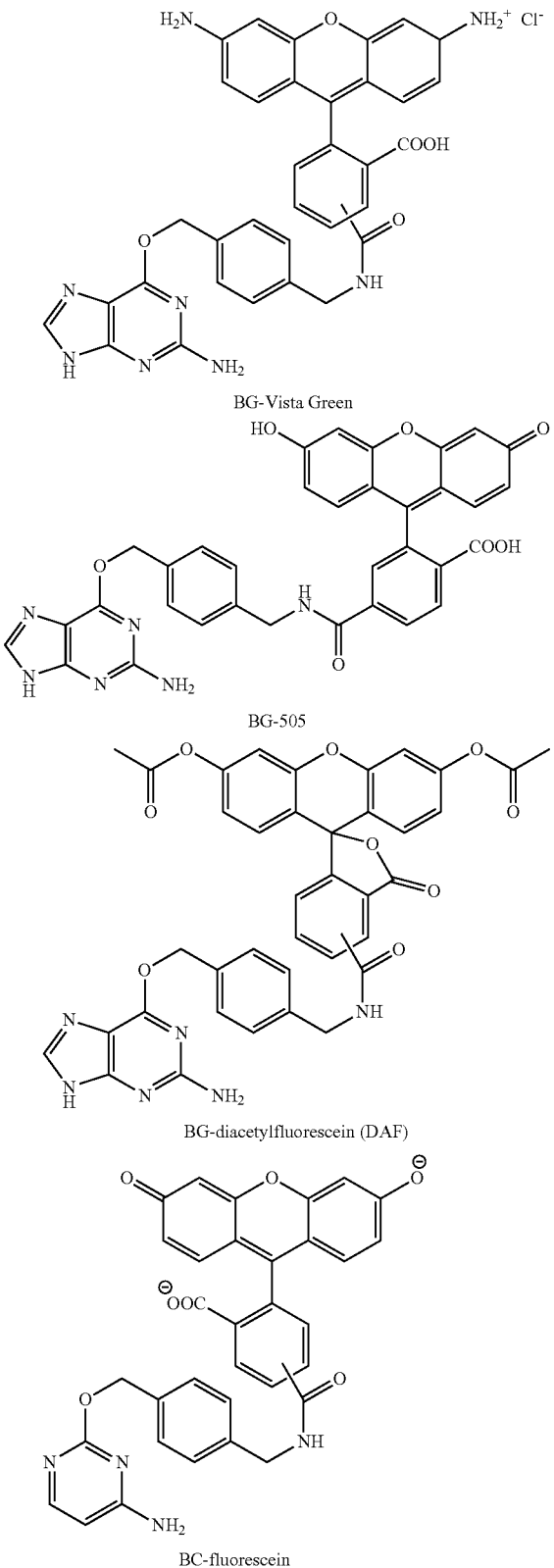

BG-Vista Green

BG-505

BG-diacetylfluorescein (DAF)

BC-fluorescein

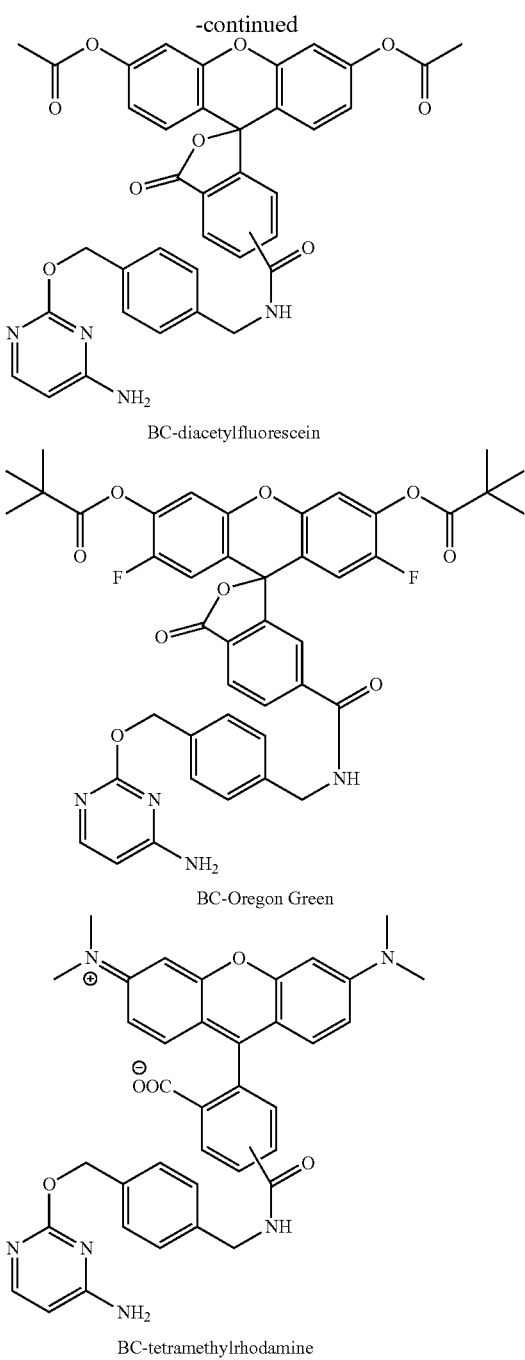

BC-diacetylfluorescein

BC-Oregon Green

BC-tetramethylrhodamine

DESCRIPTION

The invention relates to novel substrates of the AGT enzyme or of its mutants, constituted of a benzylnucleotide covalently bonded to a molecule of interest via a linker comprising a ring having 5 or 6 atoms. These substrates are particularly suitable for the implementation of the technique for detecting and manipulating proteins of interest fused to AGT, as described in patent application WO 02/083937. This technique is currently exploited by Covalys using enzymes known under the tradenames "SNAP-tag" and "CLIP-tag".

AGT ($O^6$-alkylguanine-DNA alkyltransferase) is understood here to mean wild AGT regardless of its origin (human, mouse, rat, etc.) and its functional mutants capable of transferring a molecule of interest conjugated to a benzylnucleotide substrate to a thiol function of the enzyme. SNAP-tag enzymes (Juillerat et al., Chemistry & biology, Vol. 10, 313-317, April 2003) and CLIP-tag enzymes (Gautier et al., Chemistry & Biology, 15, 128-136, February 2008) sold by Covalys are mutants of human AGT, the substrates of which are respectively $O^6$-benzylguanine (denoted hereinbelow by BG) and $O^2$-benzylcytosine (denoted hereinbelow by BC). The N-AGT enzyme (Gronemeyer et al., Protein Engineering, Design and Selection, Vol. 19, No. 7, pp. 309-316, 2006) is another mutant of this enzyme, the reactivity of which with $O^6$-benzylguanine is better than that of the SNAP-tag enzyme.

Quite unexpectedly, the reactivity of substrates of AGT according to the invention with this AGT enzyme, and in particular with its SNAP-tag, CLIP-tag and N-AGT mutants is much better than that of the conventional substrates of these enzymes, which is expressed by much faster AGT labeling kinetics. The AGT substrates according to the invention thus make it possible to extend the application of AGT and its mutants to fields where the concentrations of substrates and the labeling times were to date limiting (high throughput screening, diagnosis, medical imaging, etc.).

The AGT substrates according to the invention are the compounds of formula (I):

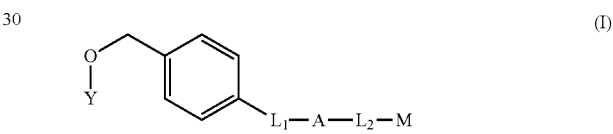

(I)

in which:
Y—O together form a nucleotide chosen from: guanine, cytosine, uracil, thymine, xanthine, hypoxanthine;
$L_1$ and $L_2$ are linkers;
M is a molecule of interest or a reactive group;
A represents a carbon-based ring or a heterocycle containing a single nitrogen atom, which ring or heterocycle is aromatic or saturated, unsubstituted or substituted by a carboxyl group, and which comprises 5 or 6 atoms.

The substrates of formula (I) for which the nucleotide is guanine, xanthine or hypoxanthine correspond to the formula (II):

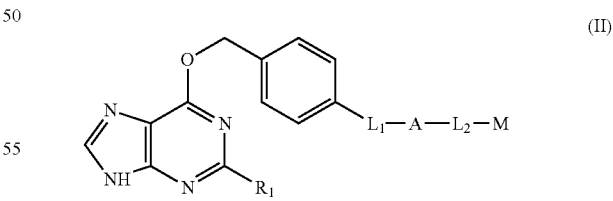

(II)

in which $L_1$, A, $L_2$ and M have the same meanings as above and $R_1$ is chosen from hydrogen, the $NH_2$ group, or the OH group and the oxo group. It will be noted that when $R_1$ is the $NH_2$ or OH group, the Y—O group is respectively guanine or xanthine.

In the case where $R_1$ is an OH group, the predominant form is the tautomer in which $R_1$ is an oxo group and the bond between the carbon at position 2 and the nitrogen at position 3 of the purine is a single bond.

The substrates of formula (II) in which $R_1$ is an $NH_2$ group are preferred. These preferred substrates are derivatives of benzylguanine.

The substrates of formula (I) for which the nucleotide is cytosine, thymine or uracil correspond to the formula (III):

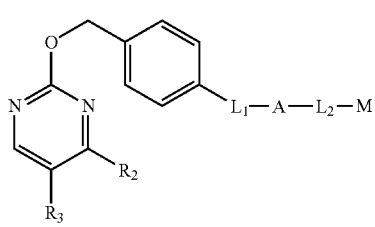

(III)

in which:
$L_1$, A, $L_2$ and M have the same meanings as above;
$R_2$ is chosen from the $NH_2$, OH and oxo groups; and
$R_3$ is chosen from hydrogen and the $CH_3$ group.

In the case where $R_2$ is an OH group, the predominant form is the tautomer in which $R_2$ is an oxo group and the bond between the carbon at position 4 and the nitrogen at position 3 of the pyrimidine is a single bond.

The substrates of formula (III) in which $R_2$ is an $NH_2$ group and $R_3$ is a hydrogen atom are preferred. These preferred substrates are derivatives of cytosine.

Group A

Group A is a carbon-based ring or a heterocycle containing a single nitrogen atom, which ring or heterocycle is aromatic or saturated, unsubstituted or substituted by a carboxyl group comprising 5 or 6 atoms.

Preferably, the A group is a divalent radical chosen from the following groups:

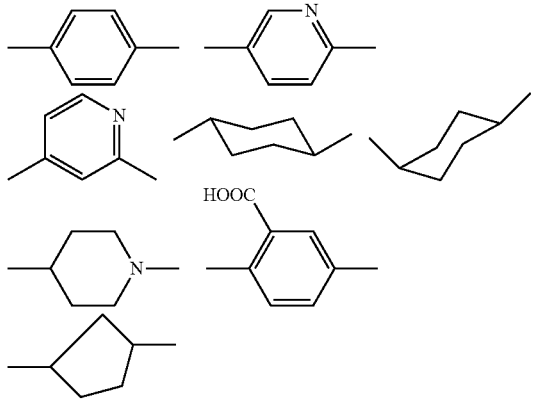

Linkers

The linkers $L_1$ and $L_2$ respectively connect the benzyl nucleotide and the molecule of interest to the A group. The structure of these linkers is determined by the chemical synthesis route chosen in order to conjugate the A group with the benzyl nucleotide on the one hand and the molecule of interest on the other hand.

Generally, the linkers are constituted by a single covalent bond or by a divalent organic radical, chosen from: linear or branched $C_1$-$C_{20}$ alkylene groups optionally containing one or more double or triple bonds; $C_5$-$C_8$ cycloalkylene groups and $C_6$-$C_{14}$ arylene groups, said alkylene, cycloalkylene or arylene groups optionally containing one or more heteroatoms, such as oxygen, nitrogen, sulfur, phosphorus or one or more carbamoyl or carboxamido group(s), and said alkylene, cycloalkylene or arylene groups optionally being substituted by $C_1$-$C_8$ alkyl, $C_6$-$C_{14}$ aryl, sulfonate or oxo groups.

In particular, the linkers may be chosen from the following divalent groups:

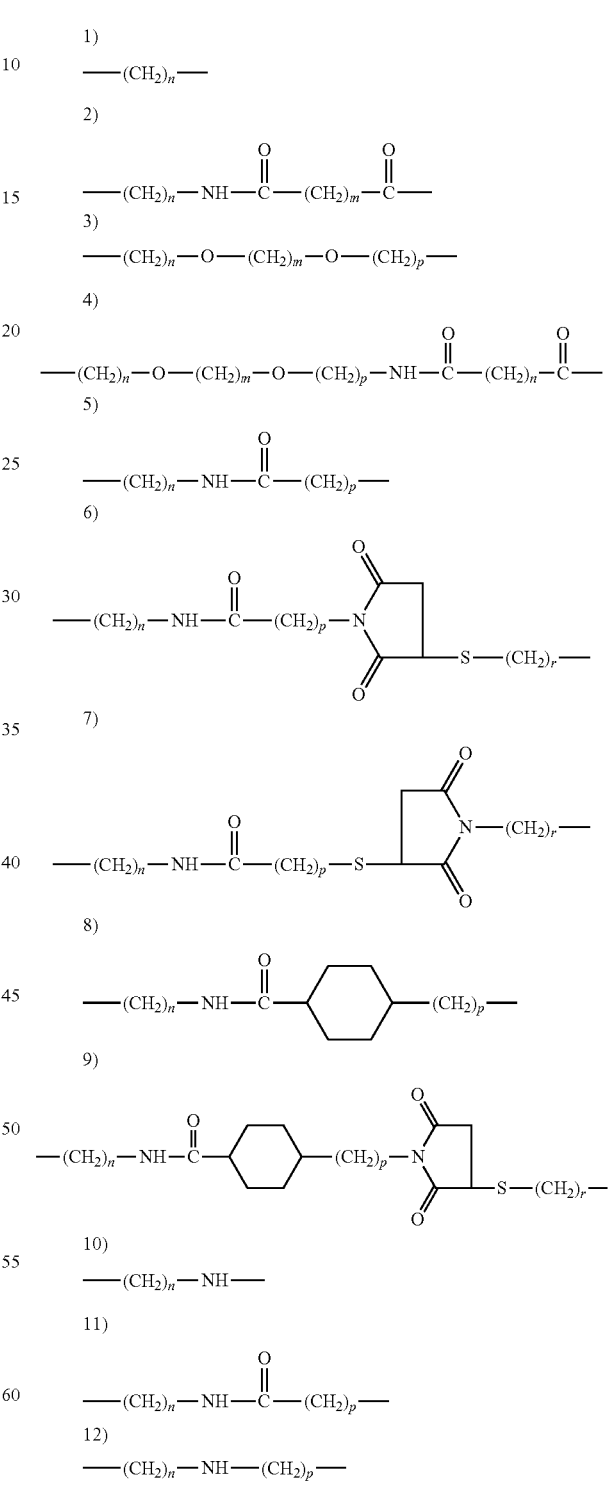

in which n, m, p, r are integers from 1 to 16, preferably from 1 to 5.

As regards $L_1$, the divalent group of formula below is preferred:

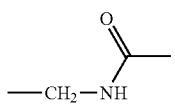

As regards $L_2$, the following divalent groups are preferred:

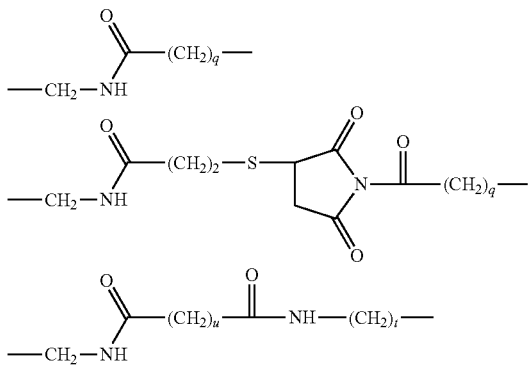

in which q, u, t are integers between 1 and 10.

Molecule of Interest

As mentioned above, the AGT substrates according to the invention are particularly intended to be used to label an AGT enzyme with a molecule of interest. When this enzyme is expressed in the form of a fusion protein with a protein of interest, it will then be possible to label said protein with the molecule of interest borne by the AGT substrate.

The molecule of interest may be of very diverse nature and function as shown by the literature on SNAP-tag technology, and depends on the envisaged application. In particular, the molecule of interest may be chosen from: a luminescent compound or a fluorophore, a radioactive molecule, a member of a pair of binding partners, a molecule capable of interacting with other biological molecules, a molecule capable of bonding covalently or non-covalently with other molecules, a molecule capable of generating hydroxyl radicals when it is exposed to $H_2O_2$ and ascorbic acid, a molecule capable of generating reactive radicals after exposure to light, a molecule covalently bound to a solid support, a lipid or any other molecule capable of inserting itself into the plasma membrane, and a biomolecule having enzymatic, chemical or physical properties of interest.

In one particular embodiment, the molecule of interest is chosen from: avidin, streptavidin, biotin.

In another embodiment, the molecule of interest is a label capable of generating or modulating a measurable signal, in particular a luminescent compound or a fluorophore. In this case, and by way of non-limiting example, the molecule of interest may be chosen from the following luminescent compounds or fluorophores:

organic fluorophores such as cyanines and derivatives thereof, (in particular those known under the tradenames DY647, Cy5, DY490), fluorescein and derivatives thereof, coumarin and derivatives thereof, rhodamine and derivatives thereof, carbopyronine and derivatives thereof, oxazine and derivatives thereof, AlexaFluors, Crystal Violet and derivatives thereof, perylene bisimides and derivatives thereof, squaraines, BODIPYs, NBD (nitrobenzoxadiazole) and derivatives thereof, DABCYL (4-((4-(dimethylamino)phenyl)azo)benzoic acid) and derivatives thereof;

protein fluorophores such as GFP and variants thereof, fluorescent proteins extracted from corals, phycobiliproteins, such as B-phycoerythrin, R-phycoerythrin, C-phycocyanin, allophycocyanins, in particular those known under the name XL665;

fluorescent lanthanide complexes such as lanthanide cryptates, lanthanide chelates (in particular the chelates and cryptates of europium, terbium, samarium, dysprosium, neodymium).

The molecule of interest may also be a non-fluorescent energy acceptor and for example may be chosen from the products known under the following tradenames: the products QXL from Anaspec and in particular the products QXL 570, QXL 610, QXL 670 and QXL 680; the products DYQ660 and DYQ661 from Dyomics; the products QSY7, QSY9 and QSY21 from Invitrogen; the products ATTO540Q, ATTO580Q, ATTO621Q from ATTO-TEC.

Preferably, the molecule of interest is chosen from the products known under the tradenames: DY647; d2; ATTO647N; ATTO465; fluorescein-5-EX; 5,6-carboxyfluorescein; europium Py-bipy cryptate; terbium DOTA-TATP complex; europium py-bipy-tetraacid cryptate, europium tris-bipy cryptate, terbium cryptate Tb(KR), europium trisbipy-pentaacid cryptate, europium Py-biTATP cryptate.

More preferably still, the fluorophore is chosen from the following fluorophores: DY647, ATTO647N, fluorescein-5-ex, Tb(KR) and ATTO465.

FIGS. 1A and 1B give the formulae of some functionalized fluorophores (bearing a reactive group such as an NHS group), the synthesis of which is known or else which are commercially available, and which can be used as intermediates for manufacturing the compounds according to the invention.

Numerous fluorophores bearing a reactive group that facilitates their coupling to other molecules are commercially available. For example, the following fluorophores are commercial fluorophores: DY647-NHS, DY490-NHS (Dyomics), 5,6-carboxyfluorescein, fluorescein-5-EX (Invitrogen), ATTO647N-NHS and ATTO465-NHS (ATTO TEC), europium trisbipyridine cryptate (Cisbio)

The synthesis of cyanines bearing various substituents is widely described in the literature. Mention may be made, in particular, of the cyanines and their methods of synthesis described in U.S. Pat. No. 5,268,486 and U.S. Pat. No. 5,627,027 and European patent EP 1,322,770.

The rare-earth complexes are known compounds that are described, for example, in U.S. Pat. No. 4,761,481, U.S. Pat. No. 5,032,677, U.S. Pat. No. 5,055,578, U.S. Pat. No. 5,106,957, U.S. Pat. No. 5,116,989, U.S. Pat. No. 4,761,481, U.S. Pat. No. 4,801,722, U.S. Pat. No. 4,794,191, U.S. Pat. No. 4,637,988, U.S. Pat. No. 4,670,572, U.S. Pat. No. 4,837,169, U.S. Pat. No. 4,859,777. Other chelates are composed of a nonadentate ligand such as terpyridine (EP 403 593, U.S. Pat. No. 5,324,825, U.S. Pat. No. 5,202,423, U.S. Pat. No. 5,316,909). The rare-earth is preferably europium or terbium.

The rare-earth cryptates and the preparation thereof are themselves described, in particular, in EP 0 180 492, EP 0 601 113 and application WO 01/96 877.

The synthesis of the Tb(KR)-NHS fluorophore is described in patent application WO 2008/063721.

The DOTA-TATP-Tb and the preparation thereof are described in the article by R. A. Poole et al., in Org. BiomolChem., 2005, 3, 1013-1024.

Reactive Group

Typically, the reactive group is a respectively electrophilic or nucleophilic group which can form a covalent bond when it is brought into the presence of a suitable nucleophilic or electrophilic group. The conjugation reaction between a compound according to the invention comprising a reactive group and a molecule of interest bearing a functional group leads to the formation of a covalent bond comprising one or more atoms from the reactive group.

Preferably, the reactive group is a group derived from one of the following compounds: an acrylamide, an activated amine (for example a cadaverine or an ethylenediamine), an activated ester, an aldehyde, an alkyl halide, an anhydride, an aniline, an azide, an aziridine, a carboxylic acid, a diazoalkane, a haloacetamide, a halotriazine, such as monochlorotriazine, dichlorotriazine, a hydrazine (including hydrazides), an imido ester, an isocyanate, an isothiocyanate, a maleimide, a sulfonyl halide, or a thiol, a ketone, an amine, an acid halide, a hydroxysuccinimidyl ester, a hydroxysulfosuccinimidyl ester, an azidonitrophenyl, an azidophenyl, a 3-(2-pyridyldithio)propionamide, glyoxal and in particular the groups of formula:

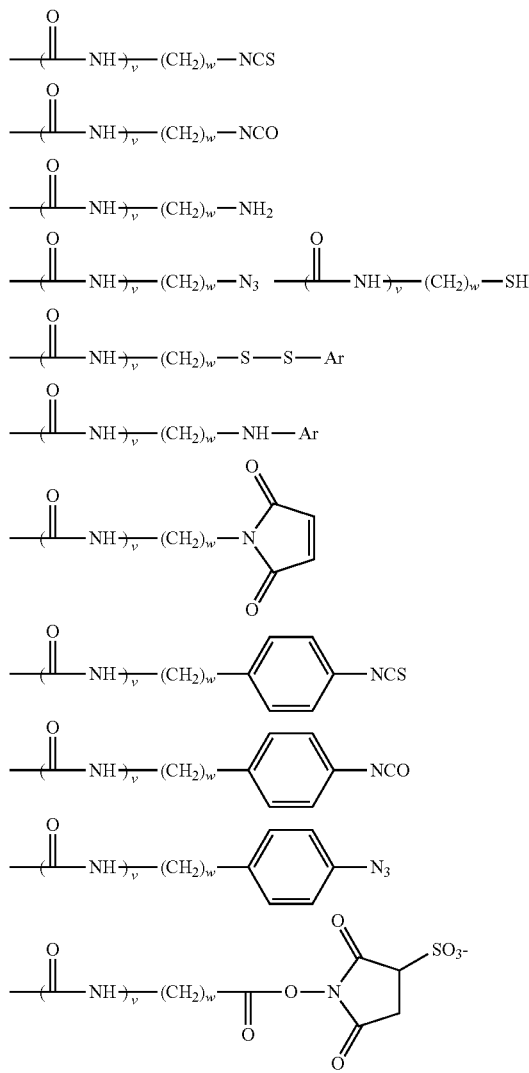

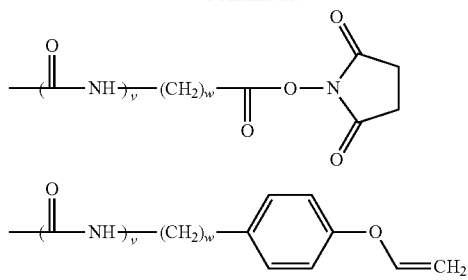

in which w varies from 0 to 8 and v is equal to 0 or 1, and Ar is a saturated or unsaturated heterocycle having 5 or 6 ring members, comprising 1 to 3 heteroatoms, optionally substituted by a halogen atom.

Preferably, the reactive group is a carboxylic acid, an amine, a succinimidyl ester of carboxylic acid, a haloacetamide, a hydrazine, an isothiocyanate, a maleimide group, an aliphatic amine.

The compounds of formula (I) according to the invention in which the M group is a reactive group are synthesis intermediates useful for obtaining compounds of formula (I) in which M is a molecule of interest.

Preferred Compounds

The compounds of formula (I') are preferred:

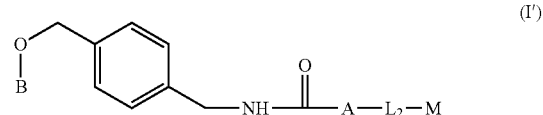 (I')

in which:

B represents a group of formula (II') or (III') below:

 (II')

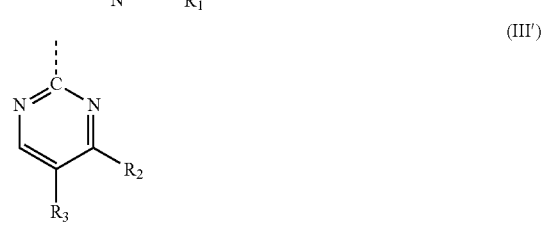 (III')

in which the dotted lines represent the bonds with the oxygen of the formula (I'), $R_1$ is chosen from: H, $NH_2$, an OH group or an oxo group, $R_2$ is chosen from: $NH_2$, OH or oxo, $R_3$ is chosen from: H or a $CH_3$ group;

$L_2$ is a linker;

M is a molecule of interest or a reactive group;

A is chosen from the following divalent groups:

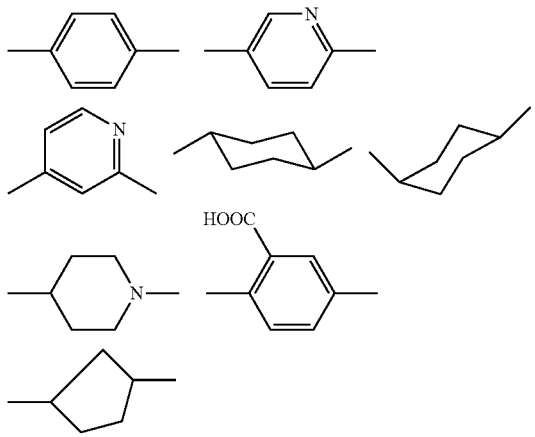

The compounds of formula (I') comprising a group of formula (III') and in which $R_2$ is an $NH_2$ group and $R_3$ is H, and also those of formula (I') comprising a group of formula (II') and in which $R_2$ is an $NH_2$ group constitute preferred subfamilies.

The formula (I') encompasses the compounds of the following formulae, in which M and $L_2$ are as defined previously. For each formula, the meaning of the $L_1$-A group is indicated below.

$L_1$-A forms a benzamide group:

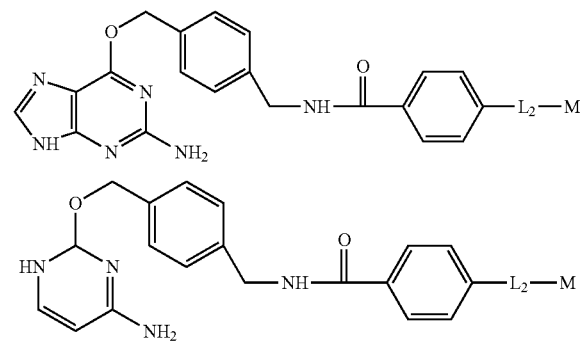

$L_1$-A forms a nicotinamide group:

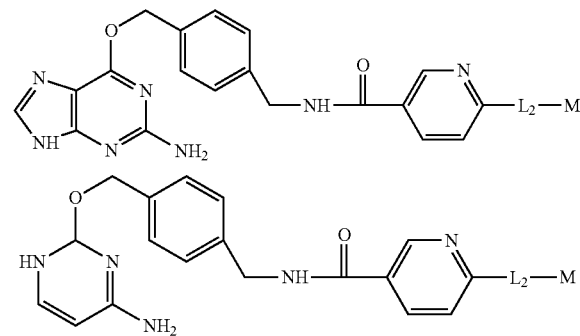

$L_1$-A forms an isonicotinamide group:

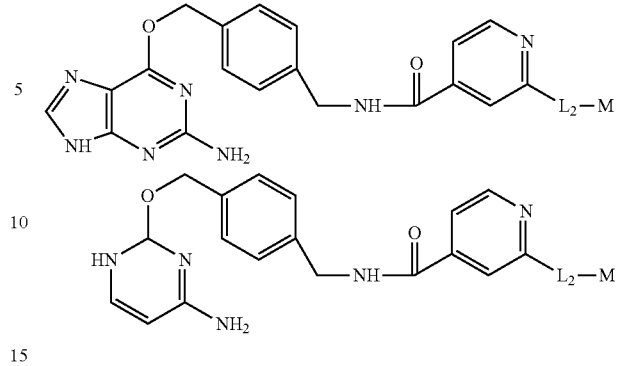

$L_1$-A forms a trans-cyclohexylamide group:

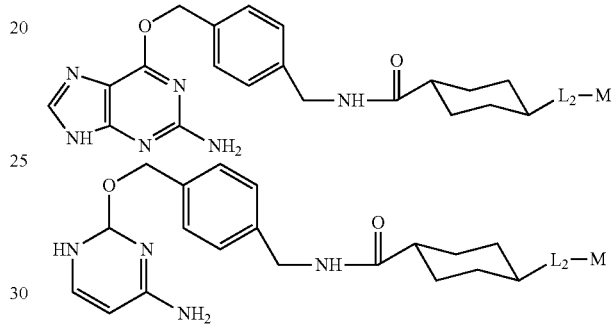

$L_1$-A forms a cis-cyclohexylamide group:

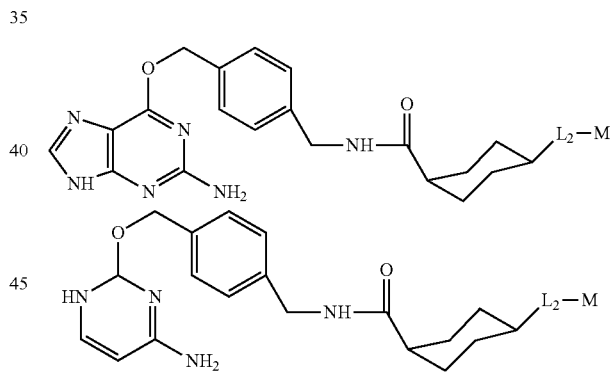

$L_1$-A forms a piperidinylamide group:

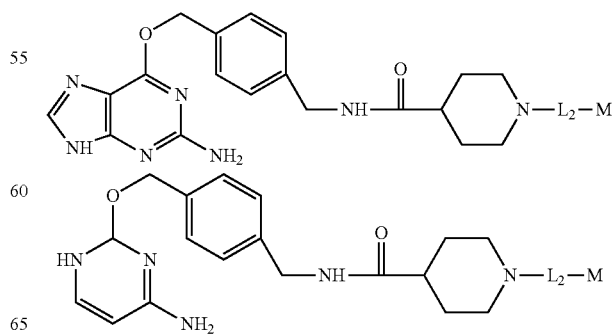

L₁-A forms a carboxybenzamide group:

In the remainder of the present description, the abbreviations below will be used:
DCC: Dicyclohexylcarbodiimide
DTT: Dithiothreitol
THF: Tetrahydrofuran
DMF: Anhydrous dimethylformamide
TBTU: O-(benzotriazol-1-yl)-1,1,3,3-tetramethyluronium tetrafluoroborate
TEAB: Triethylammonium bicarbonate
SPDP: N-Succinimidyl 3-[2-pyridyldithio]propionate
TCEP: tris[2-carboxyethyl]phosphine hydrochloride
DMSO: Anhydrous dimethylsulfoxide
DIPEA: Diisopropylethylamine
TFA: Trifluoroacetic acid
BG: $O^6$-benzylguanine
BC: $O^2$-benzylcytosine
DMEM medium: "Dulbecco's Modified Eagle's Medium" cell culture medium, available commercially and used in numerous applications.
FCS: fetal calf serum
Ester of NHS: Ester of N-hydroxysuccinimide
FRB: binding domain of the FRAP protein with the FKBP-rapamycin complex ("FKBP-rapamycin binding domain of FRAP")
FRAP: protein that binds to the FKBP-rapamycin complex ("FKBP-rapamycin binding protein")
FKBP: protein that binds to the FK506 protein ("FK506 binding protein")
GST: Gluthatione-5-transferase
TBP: trisbipyridine. The expression "europium TBP cryptate" or the acronym KTBP denotes a compound sold by Cisbio, the formula of which is indicated in FIG. 1A The following fluorophores are commercially available: DY-647-NHS (Dyomics), 5,6-carboxyfluorescein, fluorescein-5-EX (Invitrogen), ATTO647N-NHS (ATTO TEC) and europium trisbipyridine cryptate (Cisbio)

The synthesis of the Tb(KR)—NHS fluorophore is described in patent application WO 2008/063721.
Syntheses:
I) Syntheses of Compounds of Benzylguanine-Fluorophore Type These compounds are the compounds presented in the experimental section as the reference compounds: they do not comprise an $L_1$-A-$L_2$ group between the benzylguanine and the fluorophore.

The preparation of these compounds is described in the literature and consists in bringing into contact a BG derivative bearing a reactive group capable of reacting with a fluorophore bearing another reactive group. The synthesis schemes below are based on the use of BG-NH₂ or BG-SH derivatives, which will be brought into contact, for example, with a fluorophore bearing an ester of N-hydroxysuccinimide or a maleimide group. Such fluorophores are commercially available.

Synthesis of BG-NH₂:
BG-NH₂ was synthesized according to the protocol described in the article by Antje Keppler et al., in Nature Biotechnology, 2003, 21, 86-89.

Synthesis of BG-SH
BG-SH was synthesized according to the sequence described in Scheme 1.

The reaction of BG-NH₂ with SPDP(N-succinimidyl 3-[2-pyridyldithio]propionate) followed by a reduction of the disulfide bridge with TCEP (tris[2-carboxyethyl]phosphine) hydrochloride or DTT leads, with a good yield, to the desired BG-SH under operating conditions that are well known to a person skilled in the art.

Scheme 1

Synthesis of BG-Fluorophore and of BG-S-Fluorophore

The BG-fluorophores and BG-S-fluorophores were prepared according to the methods generally used for this type of coupling. BG-NH$_2$ reacts readily with a fluorophore comprising an NHS ester function thus resulting, after purification, by preparative HPLC, in the corresponding BG fluorophore. In the case where the fluorophore bears a maleimide function, BG-SH is used, thus resulting in the BG-S-fluorophore (Scheme 2).

Scheme 2

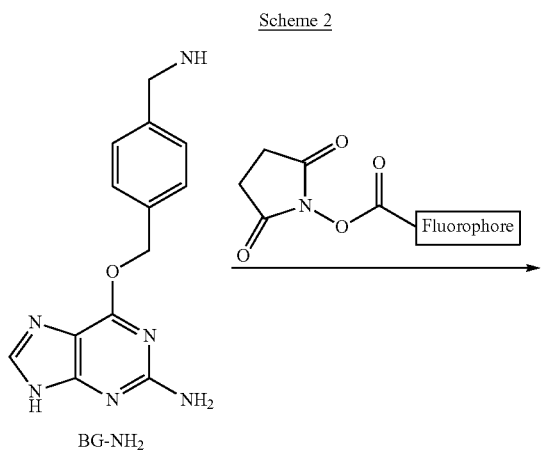

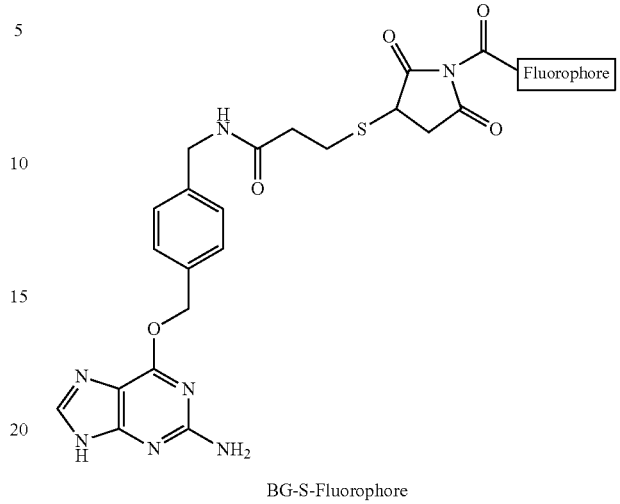

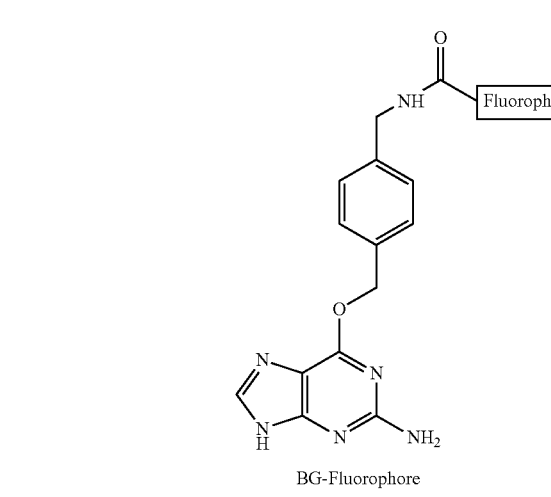

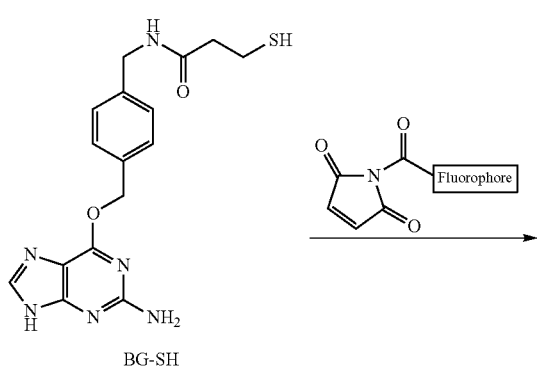

II) Synthesis of Compounds According to the Invention of Benzylguanine-L$_1$-A-L$_2$-Fluorophore Type:

The synthesis schemes below relate to compounds in which the B group is a guanine and the molecule of interest is a fluorophore; the synthesis of compounds comprising a group other than guanine or a molecule of interest other than a fluorophore use the same steps or essentially similar steps.

The preparation of these compounds is also based on the use of conventional conjugation techniques, using various reactive groups. These conventional techniques are described, for example, in Bioconjugate Techniques, G. T. Hermanson, Academic Press, 1996, p. 137-166.

In particular, the synthesis of these compounds comprises the following essential steps:

(a) preparation of an A group bearing two reactive groups, one of which is protected by a conventional protecting group;

(b) activation of the unprotected reactive group in order to obtain an A group bearing a protected reactive group and an activated reactive group;

(c) bringing into contact the product obtained in the preceding step with a derivative of BG bearing a reactive group capable of reacting with the activated reactive group borne by the A group, resulting in the formation of BG-L$_1$-A-[protected reactive group]:

(d) deprotection of the protected reactive group borne by the A group; and (e) bringing into contact the product obtained in the preceding step with a fluorophore bearing a reactive group capable of reacting with that borne by the product obtained in the preceding step, resulting in the product BG-L$_1$-A-L$_2$-fluorophore.

The use of this very general process is described in greater detail in the schemes and protocols below, and also in the experimental section.

Synthesis of the Preferred a Groups Bearing a Protected Amine and a Carboxyl Function.

1) Precursors of Methylbenzamide

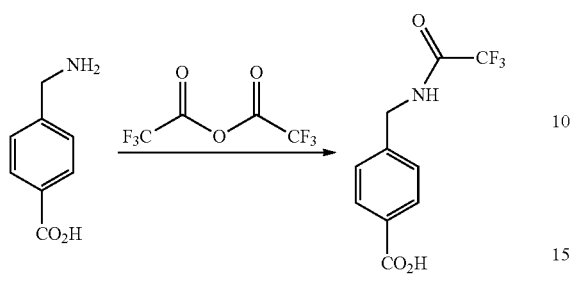

The 4-aminomethylbenzoic acid is protected in trifluoroacetate form thus enabling, later in the synthesis, a mild deprotection in a slightly basic medium.

2) Precursors of Methylnicotinamide and Methylisonicotinamide

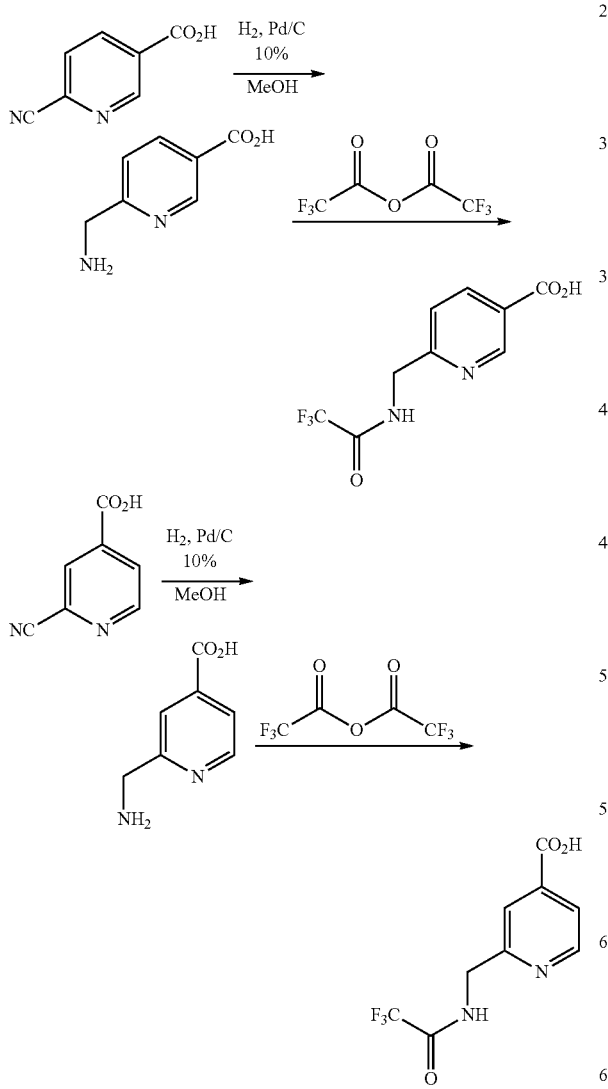

From commercial cyanonicotinyl derivatives, the corresponding aminomethylnicotinyl compounds are obtained by hydrogenolysis. The amino groups are then protected by a trifluoroacetate group.

3) Precursors of Trans-Cyclohexylamide, Cis-Cyclohexylamide and Piperidinylamide

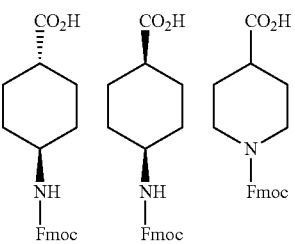

The above compounds are commercially available or can be prepared by processes well known to a person skilled in the art.

4) Precursor of Carboxymethylazidobenzamide

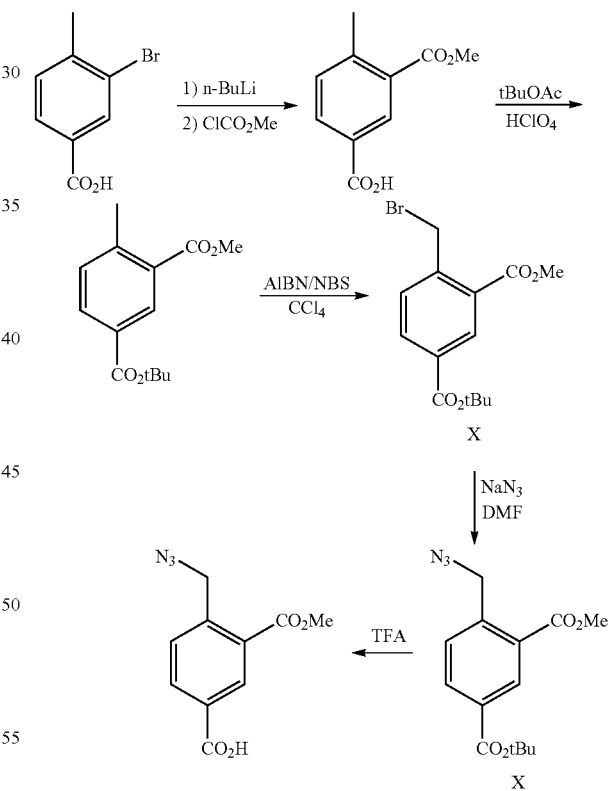

The 3-bromo-4-methylbenzoic acid is converted to the corresponding 3-carboxymethyl-4-methylbenzoic acid using the standard conditions that are generally used: halogen-lithium exchange forming a lithiated species that reacts with an electrophile (dimethyl carbonate or $ClCO_2Me$). The free carboxylic acid function is then protected in the form of a tert-butyl ester that makes it possible to obtain an orthogonal deprotection system. The introduction of the azido group is carried out in two steps: radical bromination of the aromatic methyl followed by the substitution of the bromine atom by sodium azide. Finally, the tert-butyl ester is deprotected in the presence of TFA thus resulting in the desired precursor.

Coupling of the a Groups Bearing Reactive Groups with a Benzylguanine and a Fluorophore

1) NHS Fluorophores

The general strategy for the synthesis of the products according to the invention comprising a benzylguanine and a fluorophore is presented in Scheme 3 when the fluorophore is used in the form of an ester of NHS. The N-protected A groups (the synthesis or the source of which were presented previously) are activated either in the form of anhydrides (use of DCC) or in the form of N-hydroxysuccinimidyl esters (use of TBTU). These intermediates react rapidly with the BG-$NH_2$ thus resulting in the product of formula BG-$L_1$-A N-protected.

As a function of the protective group borne by the nitrogen atom of the A group, the deprotection conditions used make it possible to obtain the compounds BG-$L_1$-A-$NH_2$. In the presence of a fluorophore comprising an N-hydroxysuccinimidyl ester function, this compound reacts under mild conditions thus resulting in the compounds BG-$L_1$-A-$L_2$-fluorophore.

2) Maleimide Fluorophores

It is also possible to use fluorophores bearing a maleimide functional group. BG derivatives bearing the $L_1$-A group may be prepared according to the same strategy as that described for the preparation of BG-SH from BG-$L_1$-A-$NH_2$. Thus the reaction of BG-$L_1$-A-$NH_2$ with SPDP, followed by the reduction with TCEP makes it possible to attain the compounds BG-$L_1$-A-NH—CO—$(CH_2)_2$—SH (Scheme 4). The latter result in BG-$L_1$-A-$L_2$-fluorophore in the presence of a fluorophore bearing a maleimide group.

The compounds according to the invention are of course particularly suitable for labeling fusion proteins comprising a molecule of interest and an AGT enzyme. Thus the invention also relates to a method of labeling a protein of interest with a group M, said protein of interest being expressed in the form of a fusion protein with an AGT enzyme, this method comprising a step of bringing said fusion protein into contact with a compound according to the invention. This method is carried out here in the following examples in order to study the enzymatic reactivity of the compounds according to the invention with various variants of AGT, in an in vitro model and in a cell model.

Scheme 3

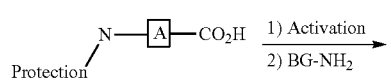
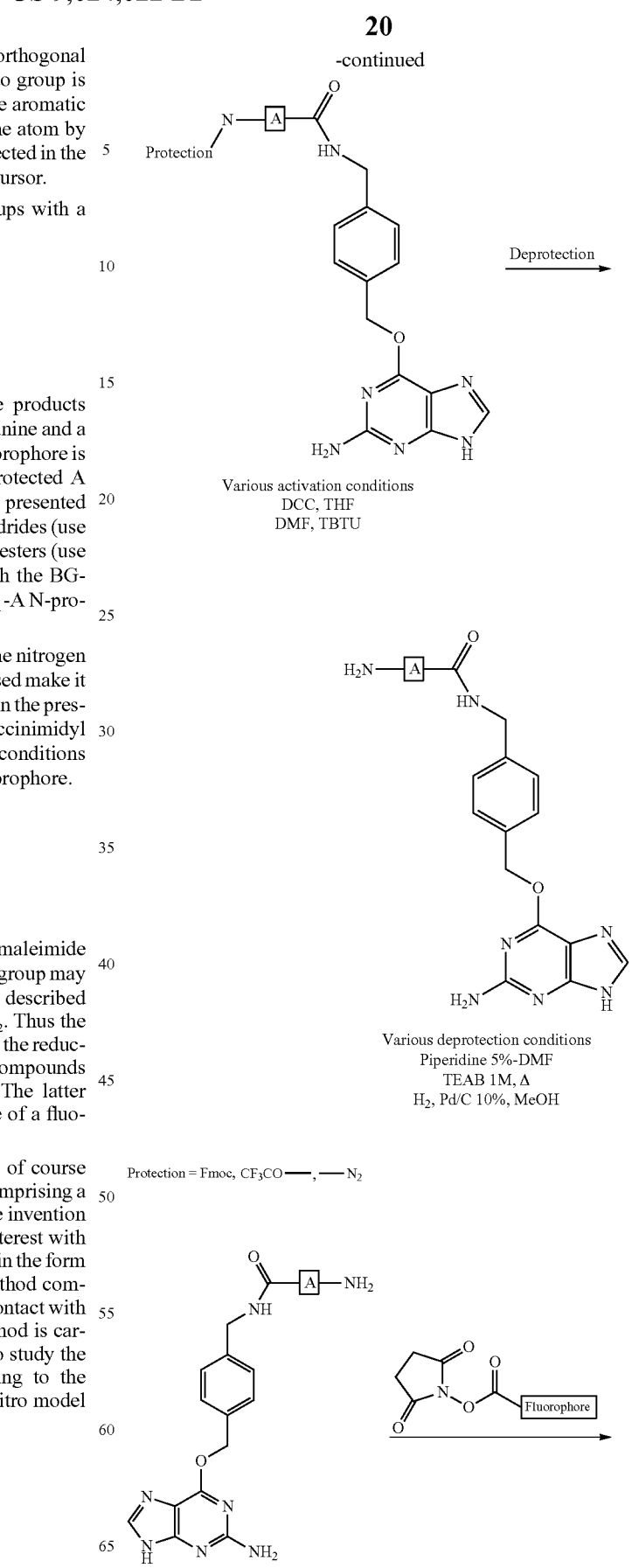
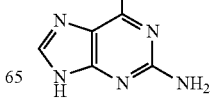

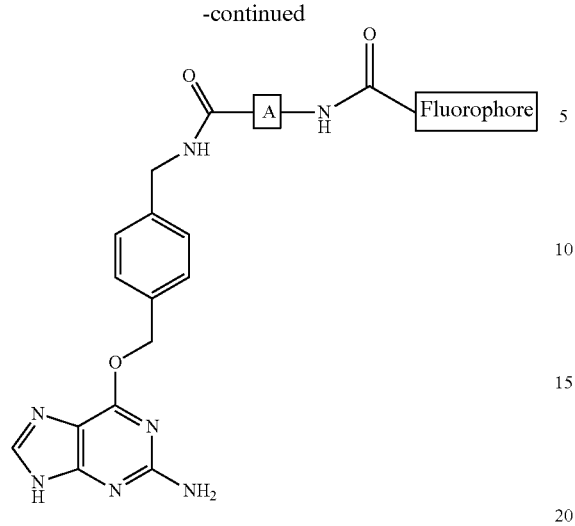
Scheme 4
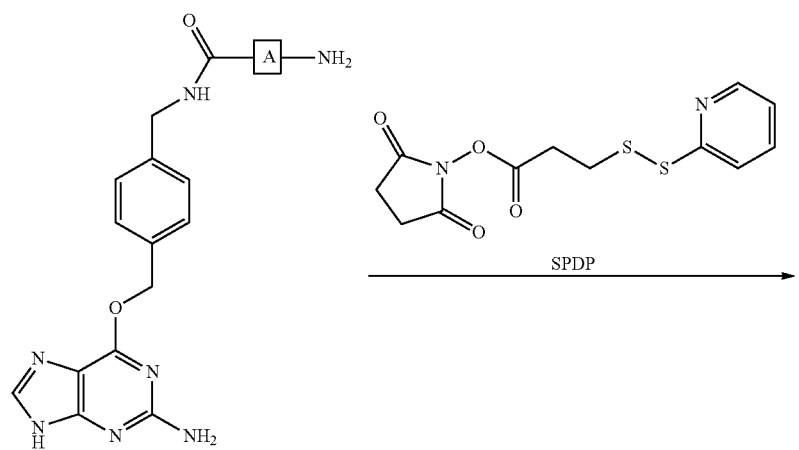
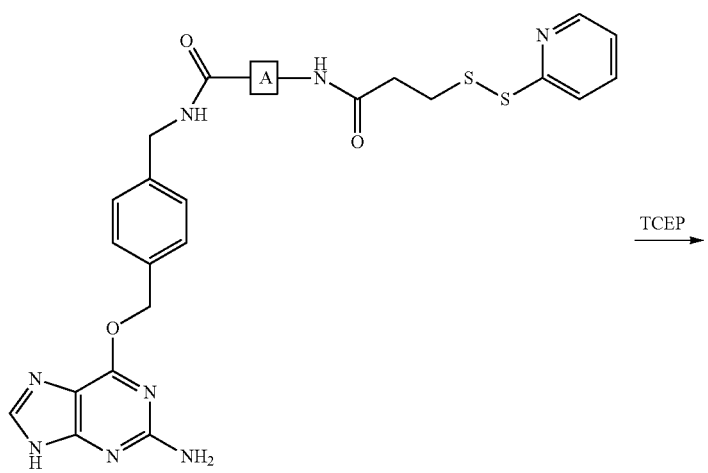

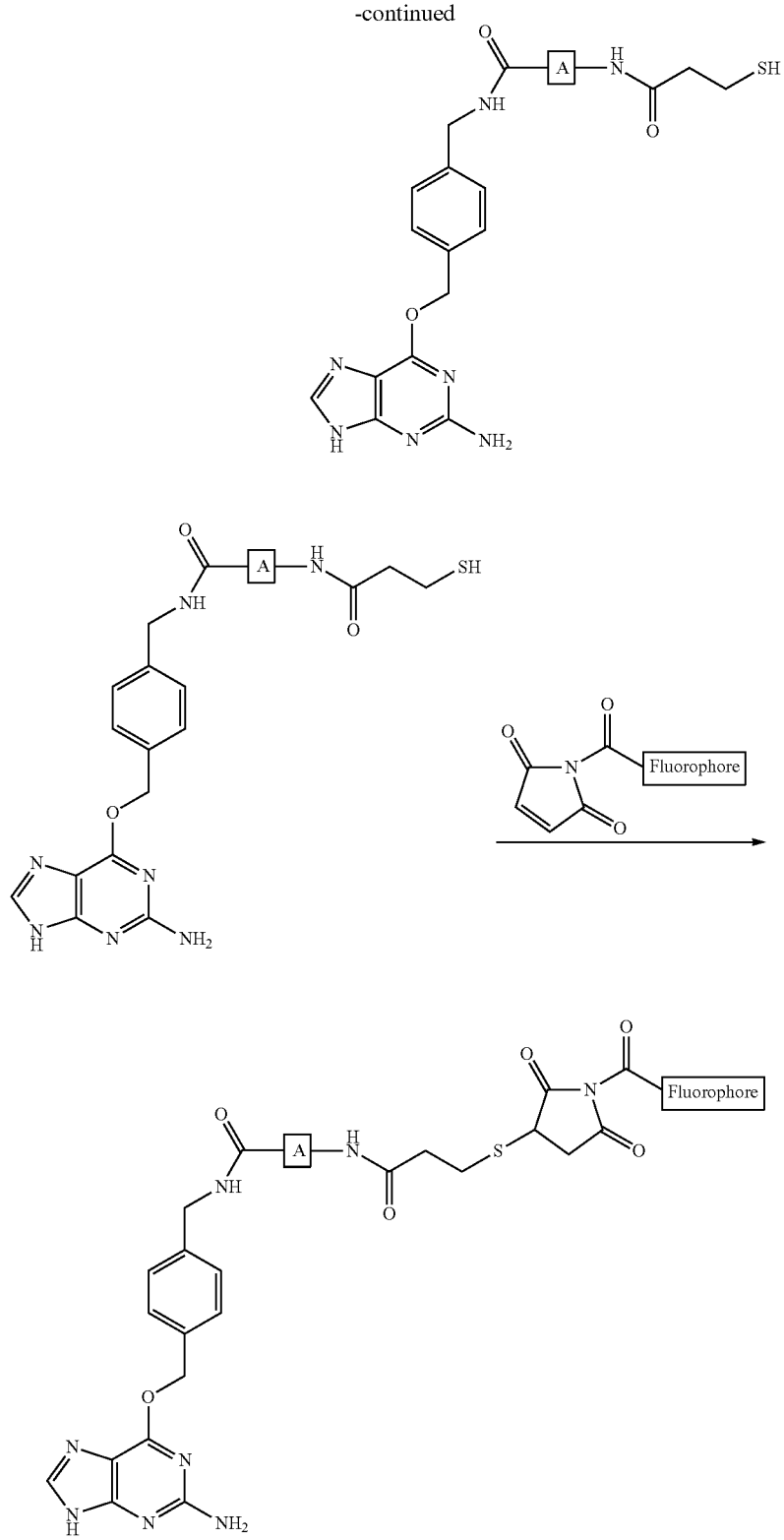

Enzymatic Reactivity Test

The objective of the following examples is to measure the transfer kinetics of a fluorophore to a fusion protein comprising an AGT enzyme (SNAP-tag, N-AGT or CLIP-tag) starting from a reference substrate (of benzyl nucleotide-fluorophore type) or else starting from compounds according to the invention (benzyl nucleotide-$L_1$-A-$L_2$-fluorophore).

These examples make it possible to demonstrate the much higher reactivity of the substrates according to the invention with the SNAP-tag enzyme and one of these variants, compared with the substrates of the prior art.

The measure of the reactivity of the substrates with the SNAP-tag enzyme is carried out either in an in vitro model, or in a living cell model.

Procedure of the Enzymatic Reactivity Test in an In Vitro Model:

The test of reactivity of the substrates according to the invention with the SNAP-tag enzyme is based on an in vitro test of labeling a recombinant protein. This labeling is demonstrated by the detection of a FRET signal between two proteins, each labeled by a fluorophore member of a pair of FRET partners.

In this case, use is made of the FRB and FKBP proteins that interact in the presence of rapamycin.

The FKBP protein is labeled by a first fluorophore via SNAP-tag technology: for this, a GST-SNAPtag-FKBP fusion protein is produced from the pSET7-26b plasmid according to the protocol of the commercial kit (SNAP express pSET7-26b kit, Covalys Biosciences AG, Witterswil/Switzerland). This fusion protein is then brought into contact with the first fluorophore conjugated to a reference BG derivative or to a BG derivative according to the invention.

The FRB protein is itself coupled via conventional conjugation techniques with a donor fluorescent compound (europium TBP cryptate (KTBP), Cisbio Bioassay) or acceptor fluorescent compound (DY647, Dyomics) depending on the case, following the protocols provided with these products.

The table below explains the nature of the pairs of fluorophores in each of the following examples 1 to 4:

| Example | BG conjugated with: | FRB fused with: |
|---|---|---|
| 1 | DY647 | KTBP |
| 2 | ATTO647 | KTBP |
| 3 | fluorescein-5-EX | KTBP |
| 4 | Tb(KR) | DY647 |
| 5 | DY647 | KTBP |
| 6 | Tb(KR) | DY647 |

In each example, 2 nmol of FRB recombinant protein labeled with a europium cryptate or DY647 (2nd fluorophore) are co-incubated at ambient temperature with 2 nmol of GST-SNAP-tag-FKBP recombinant protein and increasing concentrations of BG labeled by the first fluorophore (BG-fluorophore of the prior art or BG-$L_1$-A-$L_2$-fluorophore according to the invention).

The fluorescence readings are taken at 620 nm and at 665 nm on a RubyStar machine (BMG laboratory) after an excitation at 337 nm. The readings are carried out before and after induction of the FRB/FKBP protein interaction by 100 nM of rapamycin. This interaction is expressed by the emission of a TR-FRET signal. Since the SNAP-tag enzyme can only attach to a single fluorescent group, the increase in the TR-FRET signal is directly proportional to the percentage of labeled proteins in the reaction medium. This in vitro model makes it possible to establish enzymatic labeling kinetics as a function of the excess of substrate involved in the reaction.

The results are indicated either as d665 or as % labeling according to the following formulae:

d 665=(signal at 665 nm with the GST-ST-FKBP protein)−(signal at 665 nm without the GST-ST-FKBP protein).

The percentage of labeling is obtained by comparison with the signal corresponding to the maximum labeling that is obtained after 18 hours of incubation.

% labeling=(d665 at $t$ measured/d665 18 h of incubation)×100.

Procedure of the Enzymatic Reactivity Test in a Cell Model

This procedure makes it possible to test the reactivity of substrates according to the invention with an AGT expressed by COS 7 cells in the form of a fusion protein with the type 2 glutamate transmembrane receptor (mGluR2).

Various mutants of AGT were analyzed in this study: SNAP-tag-ST26 or CLIP-tag from Covalys or the N-AGT mutant described by Gronemeyer et al. (Protein Engineering, Design & Selection, Vol. 19, No. 7, pp. 309-316, 2006).

Plasmids:

SNAP-tag-mGluR2 plasmid, prepared from the pSET-26b plasmid according to the protocol of the commercial kit (SNAP express pSTE7-26b kit, Covalys Biosciences)

Invitrogen pcdna3.1 plasmid. This plasmid is used as a negative control; the cells transfected with this plasmid are denoted "mock" and make it possible to determine the level of non-specific labeling.

Protocol:

The transient transfection of the cells is carried out by electroporation using a Biorad electroporator: 10 million cells are transfected by 1 µg SNAP-tag-mGluR2+3 µg pcdna3.1 in a final volume of 300 µl. The electroporation parameters are: 280 V & 1000 µF.

The cells are then seeded at 150 000 cells per well in Greiner plates (opaque black bottom) previously incubated with polyornithine for 30 minutes at 37° C.

The cells are cultured in the DMEM+Phenol Red+10% FCS+penicillin/streptomycin+non-essential amino acids medium at 37° C. and 5% $CO_2$. After 24 h of expression, a first washing operation is carried out with 100 µl of this same medium.

The labeling of the AGT-mGluR2 fusion protein takes place in 100 µl of complete medium with increasing concentrations of BG-fluorophore or BG-$L_1$-A-$L_2$-fluorophore according to the invention for 1 h at 37° C. Before the reading, 4 washing operations are carried out with 100 µl of Tris-Krebs.

For the substrates bearing fluorophores ATTO647 (example 2), DY647 (examples 1 and 5) and fluorescein-5-EX (example 3), the reading is carried out in 100 µl of Tris-Krebs in direct fluorescence at 682 nm on a Rubystar machine, and at 520 nm for those bearing fluorescein-5-EX (example 3).

For the substrates bearing the terbium KR complex (examples 4 and 6), the reading is taken in 100 µl of Tris-Krebs in time-resolved fluorescence at 620 nm on a Rubystar machine.

Example 1

BG-methylbenzamide-DY647

Comparison of the reactivities between BG-DY647 and BG-methylbenzamide-DY647 and the SNAP-tag enzyme.

Structure of the Reference Substrate BG-DY647:

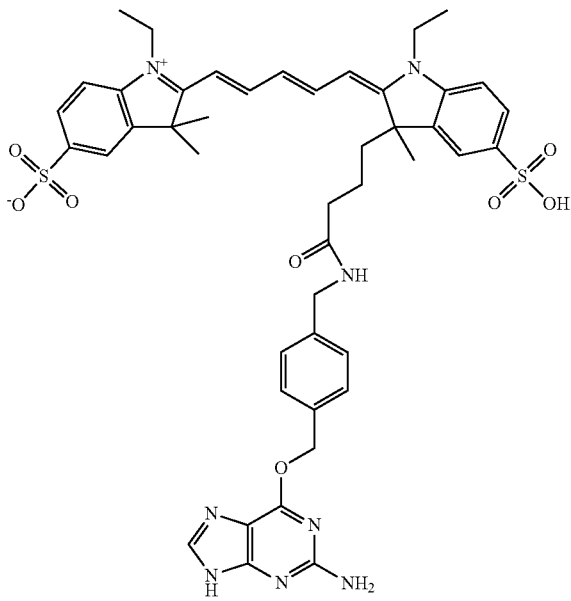

Structure of the Substrate BG-methylbenzamide-DY647:

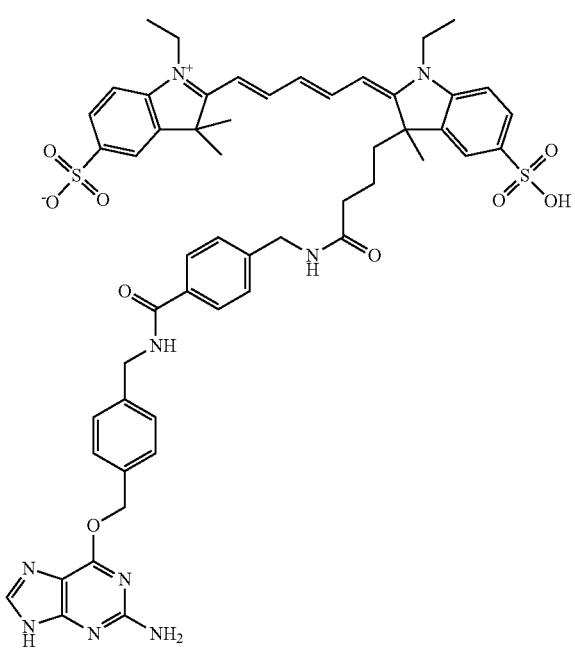

Results of enzymatic reactivity and of protein labeling in vitro

FIG. 2 represents the change in the percentage of labeling of the SNAP-tag enzyme as a function of the concentration of substrate. These results show that the labeling is greatly improved after 30 min of incubation with the substrate according to the invention comprising a methylbenzamide unit, this being regardless of the concentration of substrate tested.

Results obtained on cell model

Effect with the SNAP-tag ST26 Enzyme

Figure 3:
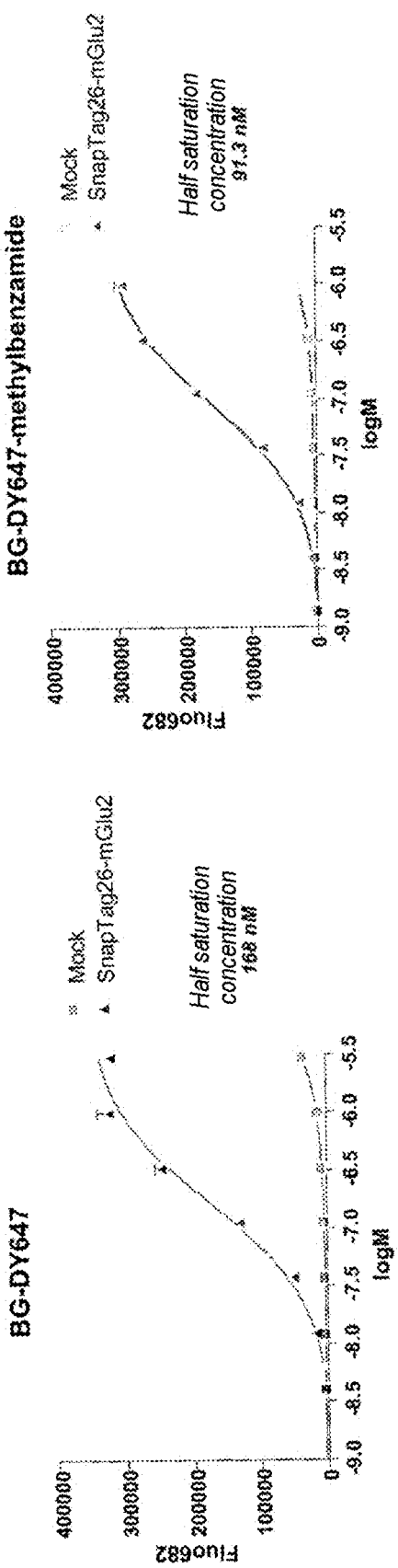

The concentration allowing half saturation of the enzyme is 168 nM with the reference compound whereas it is only 91.3 nM with the substrate according to the invention (FIG. 3). These results obtained on living cells confirm those obtained in the in vitro model. This low half saturation concentration with the compounds according to the invention makes it possible to work at low substrate concentration, here less than 100 nM.

In order to validate the effect of the substrate according to the invention on another mutant of AGT, a characterization of extracellular labeling with the NAGT mutant was carried out.

Effect with the N-AGT Enzyme

Figure 4:
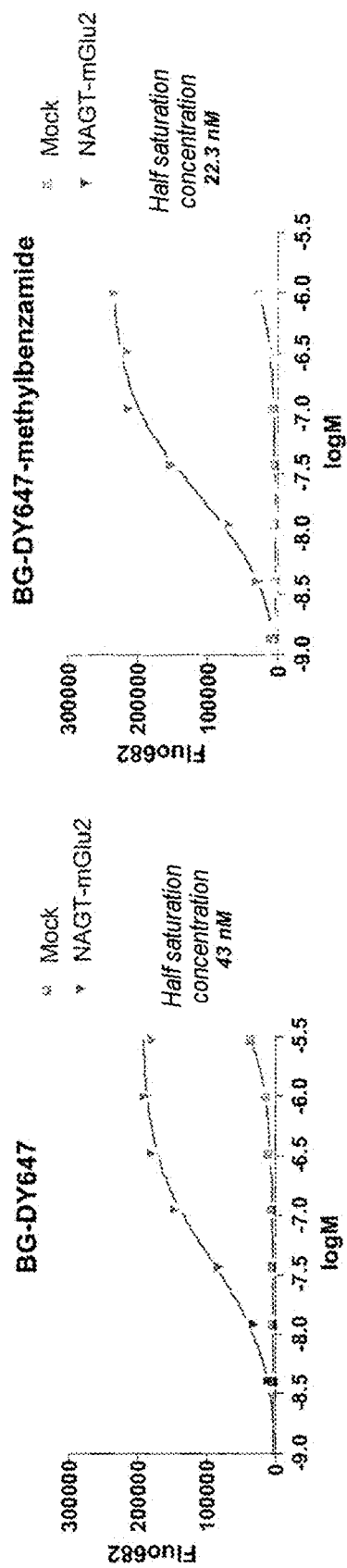

FIG. 4 shows the results obtained with the N-AGT enzyme, a more reactive mutant than SNAP-tag, and here too the half saturation concentration is around 2 times lower with the compound according to the invention (22.3 nM) relative to the reference substrate (43 nM). This example shows that the greater reactivity of the substrates according to the invention is not specific to the SNAP-tag ST-26 enzyme but is also observed when variants of this enzyme are used.

Example 2

BG-Methylbenzamide-ATTO647

Comparison of the reactivity of BG-ATTO647N/BG-methylbenzamide-ATTO647 N with the SNAP-tag enzyme.

Structure of the Reference Substrate: BG-ATTO647N:

Structure of the Substrate BG-methylbenzamide-ATTO647N:

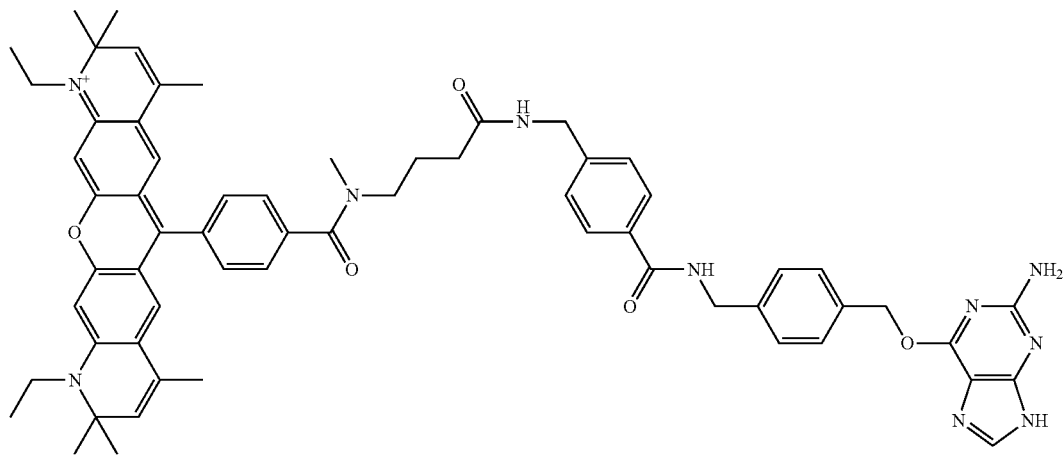 [SMILES: CCN1c2cc3c(cc2C(C)=CC1(C)C)C(c1ccc(C(=O)N(C)CCCC(=O)NCc2ccc(C(=O)NCc4ccc(COc5nc(N)nc6[nH]cnc56)cc4)cc2)cc1)=c1cc2c(cc1O3)=[N+](CC)C(C)(C)C=C2C]

Results of enzymatic reactivity and of protein labeling in vitro

Figure 5:
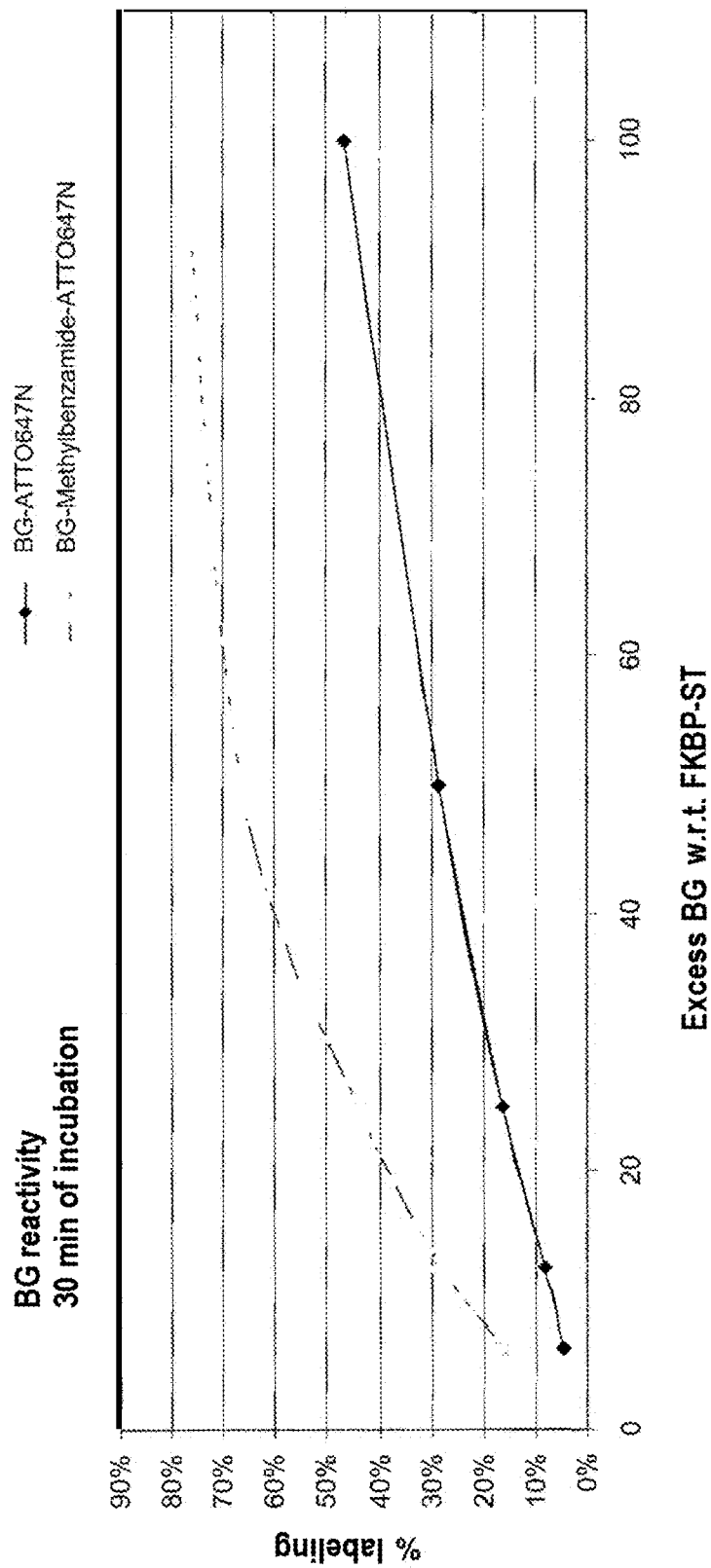

FIG. 5 represents the change in the percentage of labeling of the SNAP-tag enzyme as a function of the concentration of substrate after 30 min of incubation: here too, it is observed that the percentage of enzyme labeled by ATTO647 is much better when the substrates according to the invention are used, this being regardless of the concentration of substrate.

This example shows that the effect of the substrates according to the invention does not depend on the nature of the molecule of interest since similar results are obtained with 2 different fluorophores, DY647 (example 1) and ATTO647.

Example 3

BG-methylbenzamide-fluorescein-5-EX

Comparison of the reactivity of BG-fluorescein-5-EX/BG-methylbenzamide-fluorescein-5-EX with the SNAP-tag enzyme.

Structure of the Reference Substrate BG-fluorescein-5-EX:

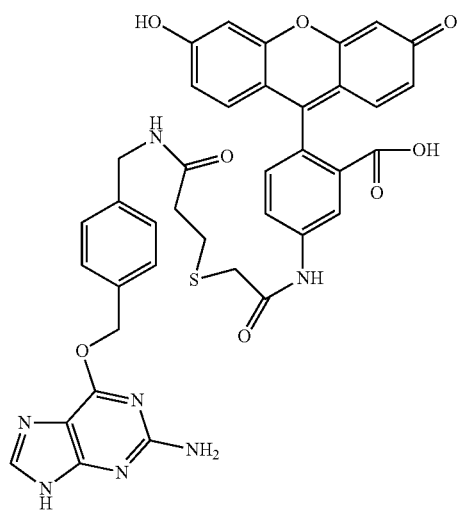 [SMILES: Nc1nc(OCc2ccc(CNC(=O)CCSCC(=O)Nc3ccc(-c4c5ccc(=O)cc-5oc5cc(O)ccc45)c(C(=O)O)c3)cc2)c2nc[nH]c2n1]

Structure of the Substrate BG-methylbenzamide-fluorescein-5-EX:

Results of enzymatic reactivity and of protein labeling in vitro

Figure 6:
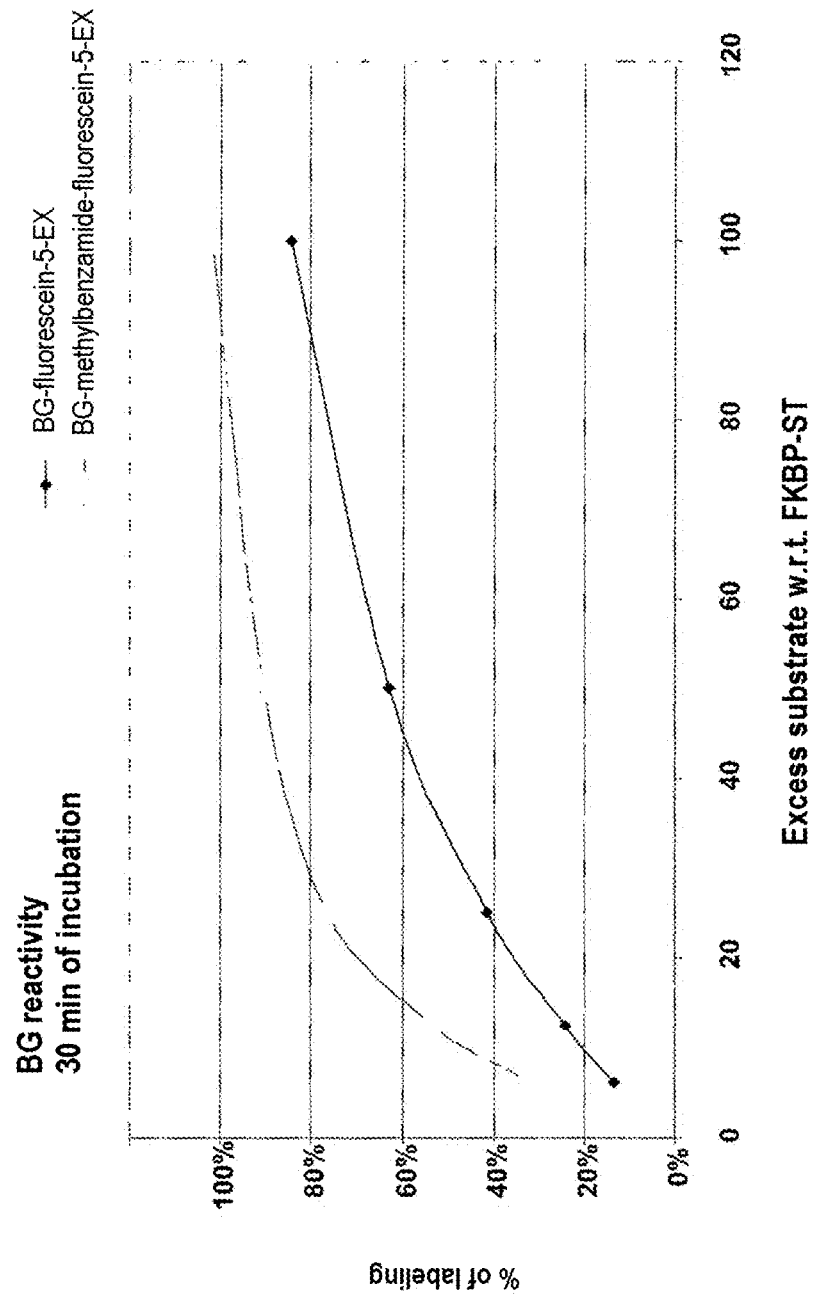

The results presented in FIG. 6 show here too that the reactivity of the substrate according to the invention with the SNAP-tag ST-26 enzyme is better than that of the reference substrate, and this being even though the reactivity of the reference BG-fluorescein-5-EX substrate may be considered to be adequate. These results also confirm that the effect of the substrates according to the invention does not depend on the nature of the molecule of interest which is conjugated thereto.

Example 4

BG-methylbenzamide-Tb(KR)

Comparison of the reactivity of BG-Tb(KR)/BG-methylbenzamide-Tb(KR) with the SNAP-tag enzyme.

Structure of the Reference Substrate: BG-Tb(KR):

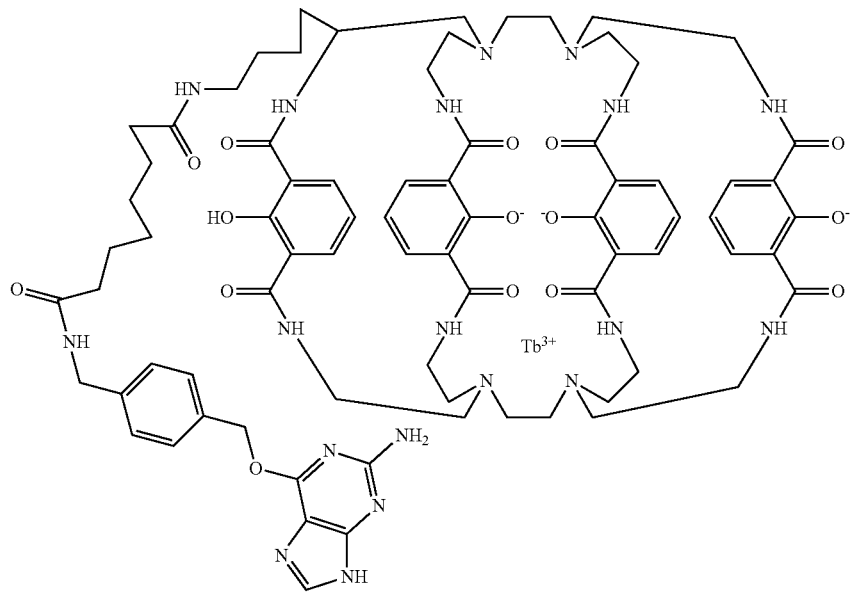

Structure of the Substrate BG-methylbenzamide-Tb(KR):

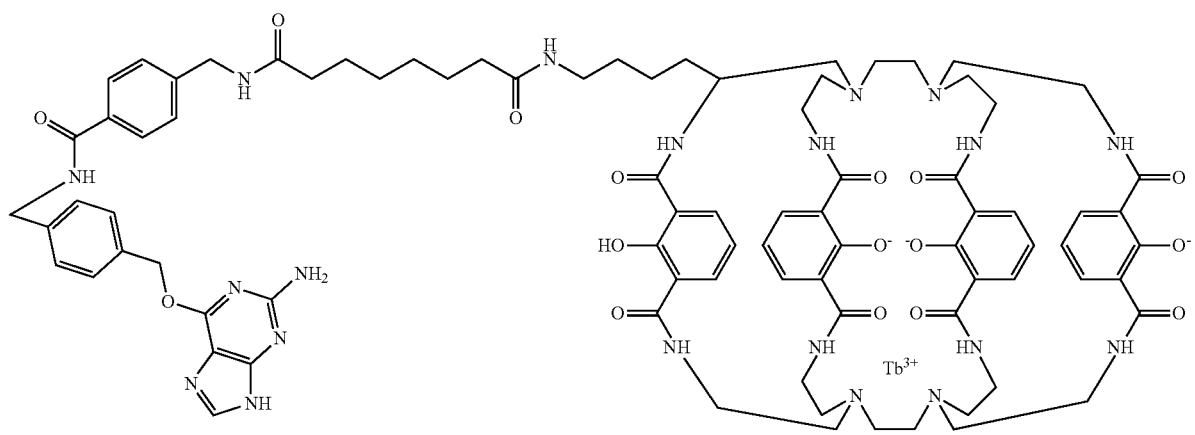

Results of enzymatic reactivity and of protein labeling in vitro

Figure 7:
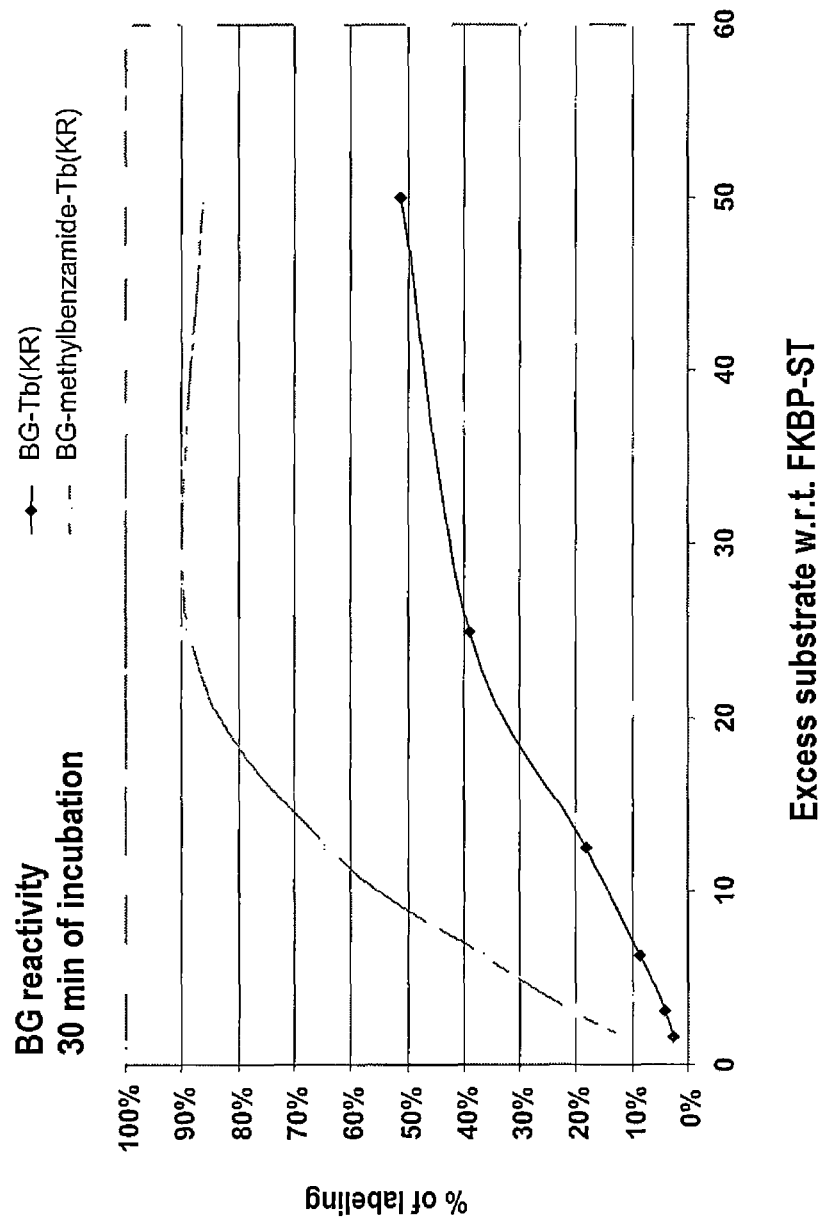

The results presented in FIG. 7 here too show a much better reactivity of the substrates according to the invention with the SNAP-tag enzyme relative to the reference substrate. It is noted here that the conjugated molecule is not an organic fluorophore as in the preceding examples but a complex composed of a polymacrocycle and a rare earth, which is much more bulky that the fluorophores tested in the preceding examples.

This example again illustrates the universal character of the substrates according to the invention which may be conjugated to a variety of molecules.

Results obtained on cell model

Figure 8:
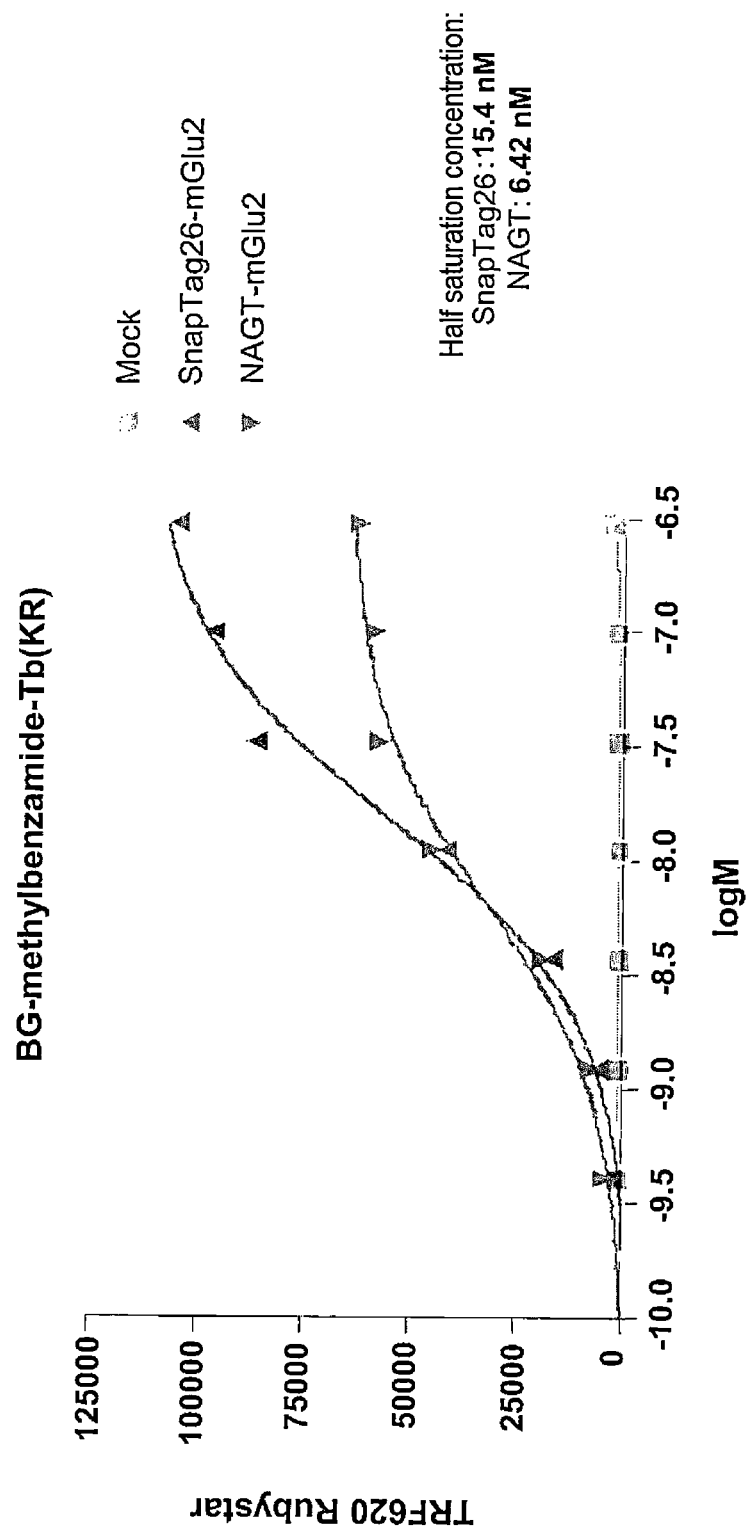

The results obtained on the in vitro model are confirmed when the BG-methylbenzamide-Tb(KR) substrate is used to label a transmembrane protein expressed at the surface of living cells. The half saturation concentrations measured with the substrate according to the invention are 15.4 nM with the SNAP-tag-ST26 enzyme and 6.4 nM with the N-AGT mutant (FIG. 8) whereas it is 60 nM with a BG-Tb(KR) (SNAP-tag) reference substrate.

Example 5

BG-aminonicotinamide-DY647

Comparison of the reactivity of BG-DY647/BG-aminomethylnicotinamide-DY647 with the SNAP-tag enzyme.

Structure of the Reference Substrate BG-DY647:

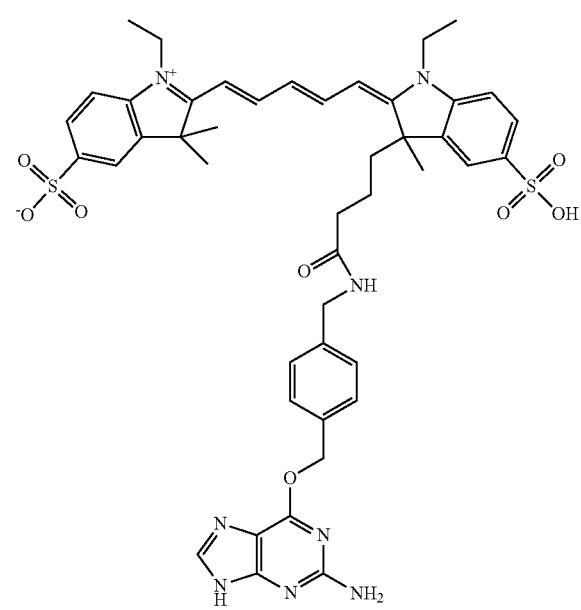

Structure of the Substrate BG-aminomethylnicotinamide-DY647:

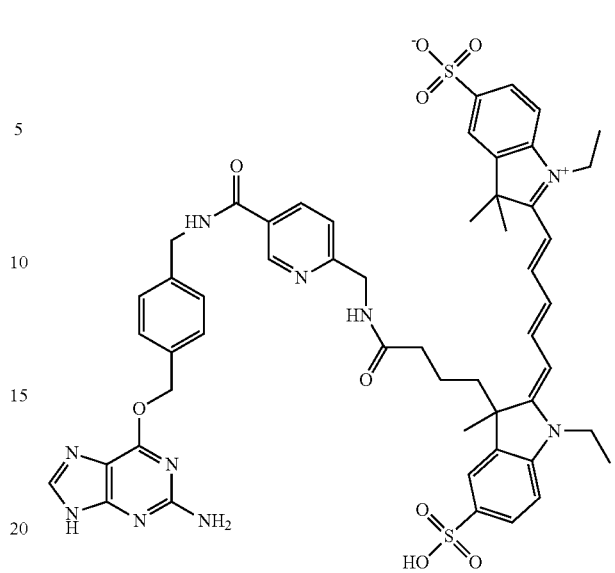

Results of enzymatic reactivity and of protein labeling in vitro

Figure 9:
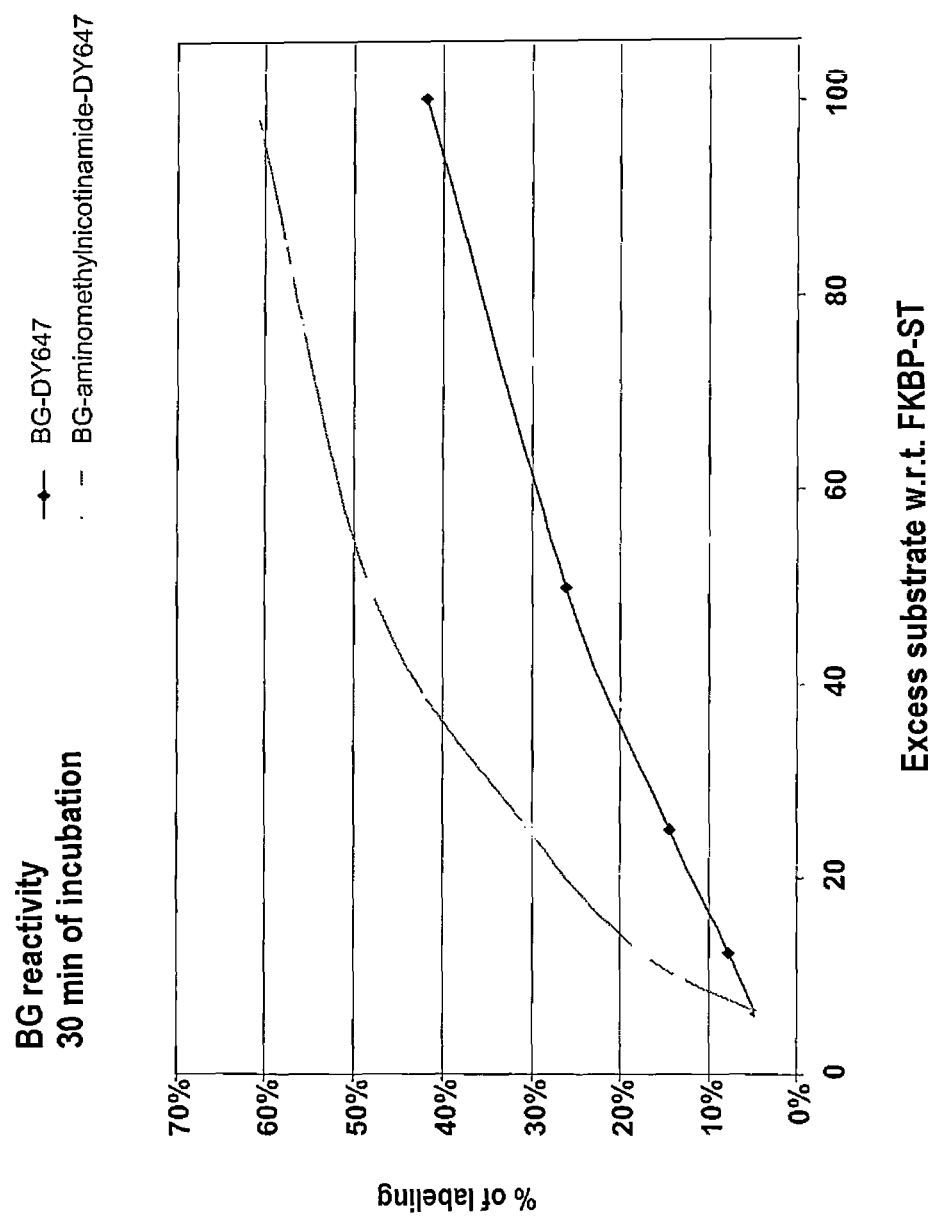

The curves from FIG. 9 show that the percentage of enzyme labeled after 30 minutes of incubation with substrates comprising an aminomethylnicotinamide unit is also much better than that observed with the reference substrate, and this being regardless of the concentration of substrate.

Furthermore, the increase in reactivity observed with the substrate comprising an aminomethylnicotinamide unit is of the same order of magnitude as that observed with the substrates comprising a methylbenzamide unit.

These results suggest that a certain variability is possible at the aromatic unit of the substrates according to the invention (unit A of formula I)

Example 6

BG-aminonicotinamide-Tb(KR)

Comparison of the reactivity of BG-Tb(KR)/BG-aminonicotinamide-Tb(KR) with the SNAP-tag enzyme.

Structure of the Reference Substrate: BG-Tb(KR)
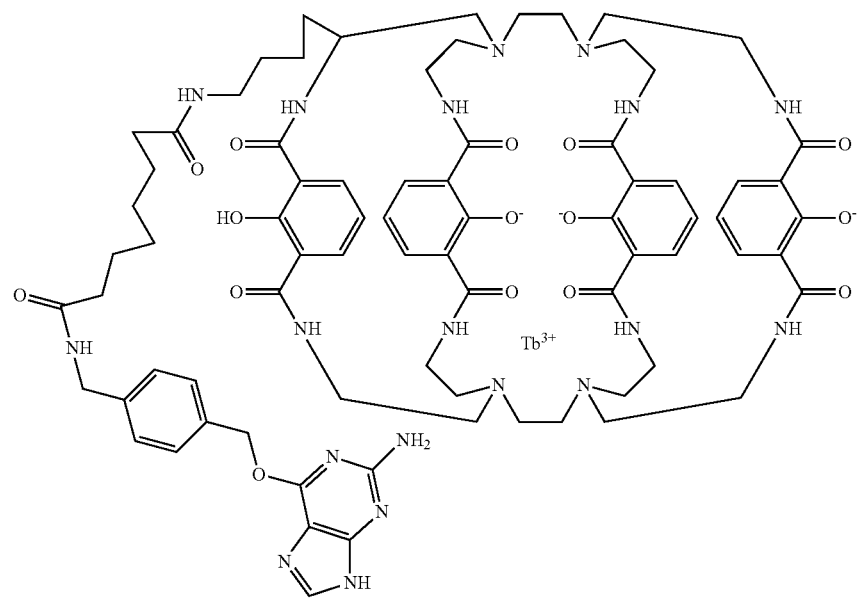
Structure of the Substrate BG-aminomethylnicotinamide-Tb (KR):
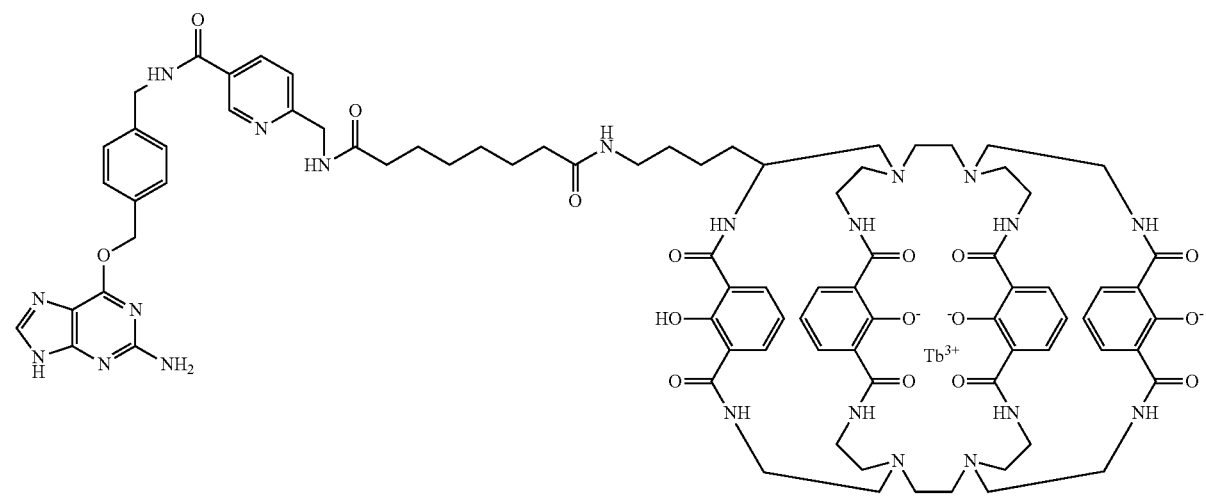

Results similar to those obtained with the compounds of the preceding examples were obtained.

Example 7

BC-methylbenzamide-Tb(KR)

Comparison of the reactivity of BC-Tb(KR)/BC-methylbenzamide-Tb(KR) with the CLIP-tag enzyme.

As mentioned previously, the CLIP-tag enzyme is a mutant of AGT that reacts with the derivatives of benzylcytosine, and is sold by Covalys, like the SNAP-tag enzyme.

Structure of the Reference Substrate: BC-Tb(KR)

fected with a single plasmid coding for the fusion protein SNAPtag-mGluR2.

Each cell population is incubated in the presence of 300 nM of BG-methylbenzamide-DY647 and increasing concentrations of reference substrates (BC-Tb(KR)) or of a substrate according to the invention (BC-methylbenzamide-Tb(KR)). The fluorescence is measured at 665 nm in TR-FRET mode on a Rubystar machine and the signal measured is representative of a transfer of energy following the dimerization of two monomers of mGluR2 labeled respectively by DY647 and Tb(KR).

Figure 10:
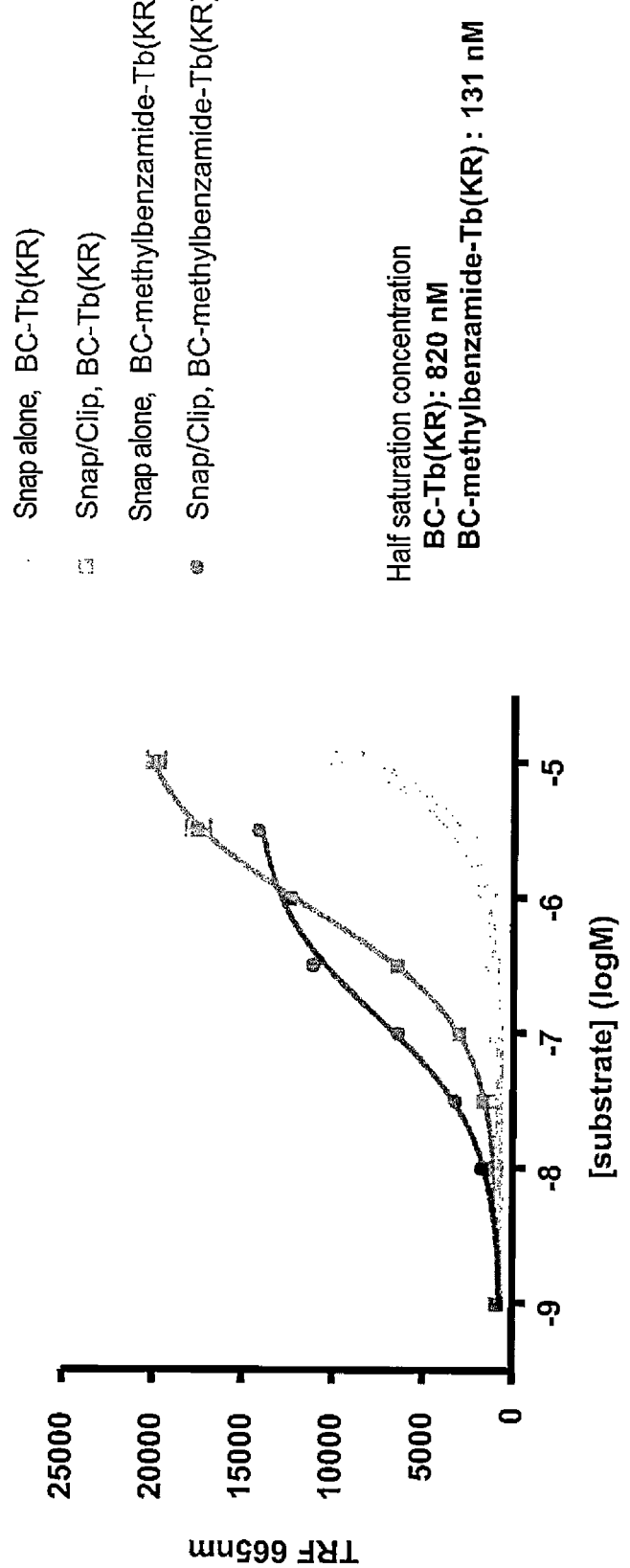

It can be observed in FIG. 10 that the half saturation concentration of CLIPtag by the benzylcytosine derivative according to the invention is 131 nM, whereas it is 820 nM with the reference compound. (The signal observed in the

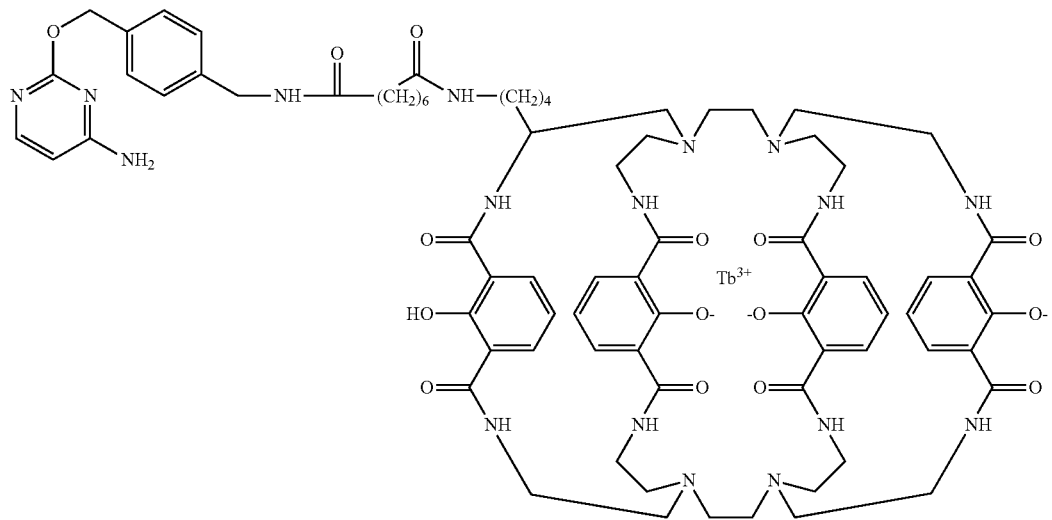

Structure of the Substrate BC-methylbenzamide-Tb(KR):

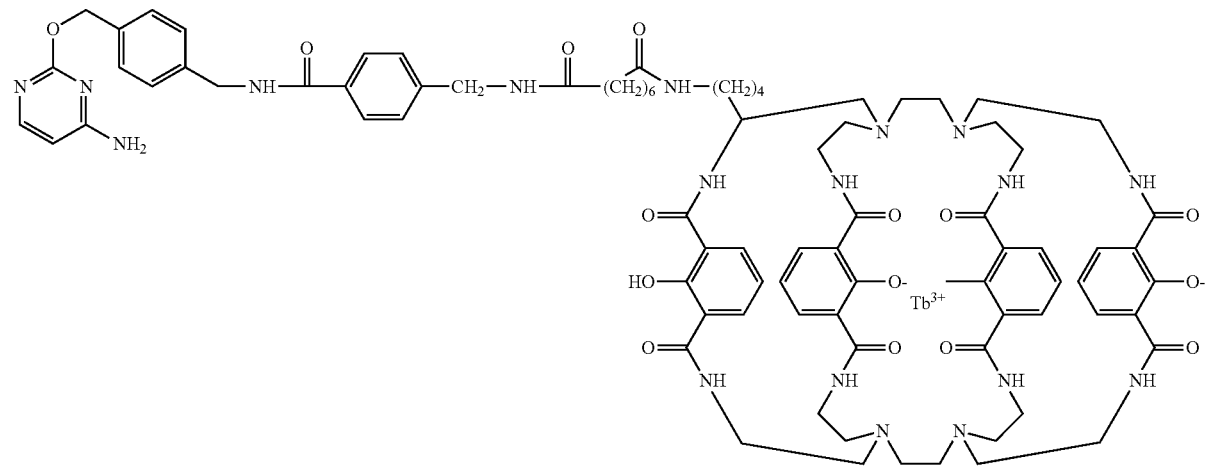

Results obtained on cell model

The cell model used in this example is different from that used in the preceding examples:

The cells are either cotransfected with a plasmid coding for the fusion protein CLIPtag-mGluR2 and another plasmid coding for the fusion protein SNAPtag-mGluR2, or transcells expressing SNAPtag-mGluR2 only corresponds to the signal of non-specific fixation of BG-DY647 by CLIPtag)

This example confirms that the unexpected effect of the substrates according to the invention is not limited to SNAPtag/benzylguanine but is also observed with CLIPtag/benzylcytosine.

Example 8

BC-methylbenzamide-DY647

Comparison of the reactivity of BC-DY647/BC-methylbenzamide-DY647 with the CLIP-tag enzyme.

This example is carried out in the same way as example 7 but the cells are incubated in the presence of 300 nM of BG-methylbenzamide-Tb(KR) and increasing concentrations of reference substrate (BC-DY647) or of substrate according to the invention (BC-methylbenzamide-DY647), the formulae of which are below:

Reference Substrate (BC-DY647)

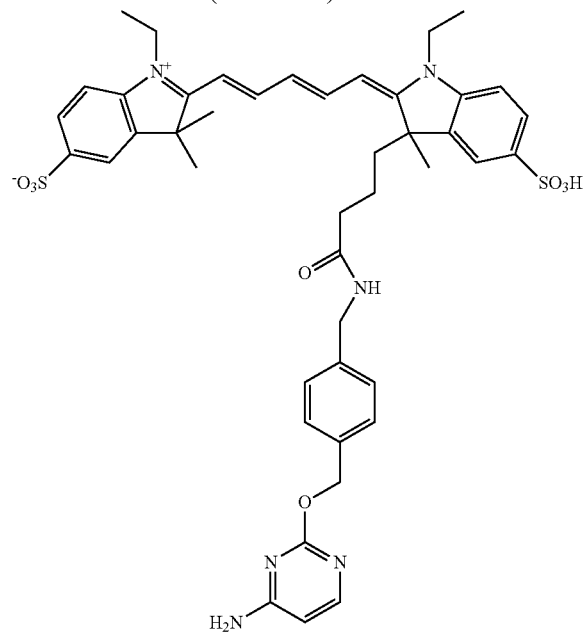

Substrate BC-methybenzamide-DY647:

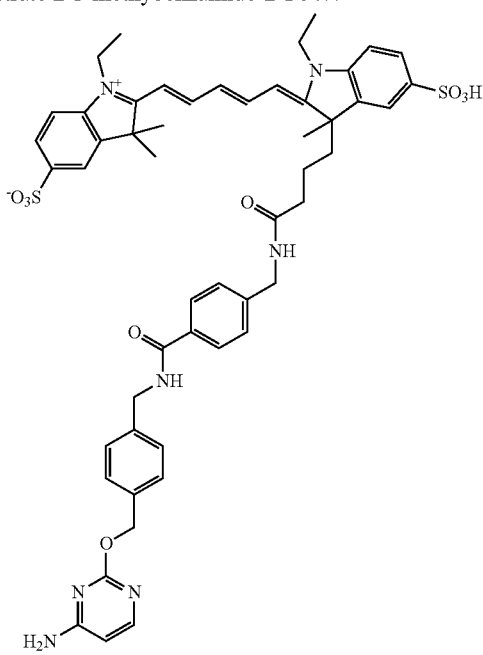

Figure 11:
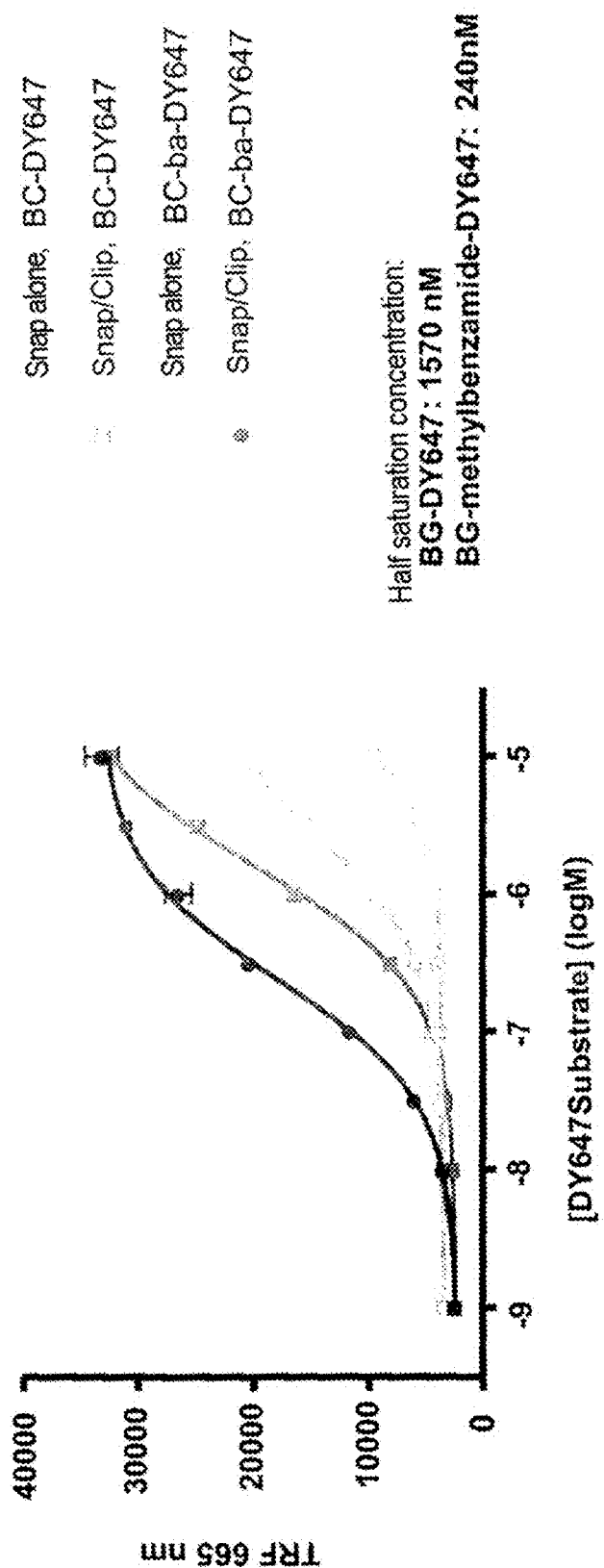

The results presented in FIG. 11 confirm the better reactivity of the substrate according to the invention (half saturation: 240 nM) with respect to the reference substrate (half saturation: 1570 nM).

Example 9

BG-cis-cyclohexane-DY647

Comparison of the reactivity of BG-DY647/BG-cis-cyclohexane-DY647 with the SNAP-tag enzyme.

Structure of the Reference Substrate BG-DY647 (Compound 1):

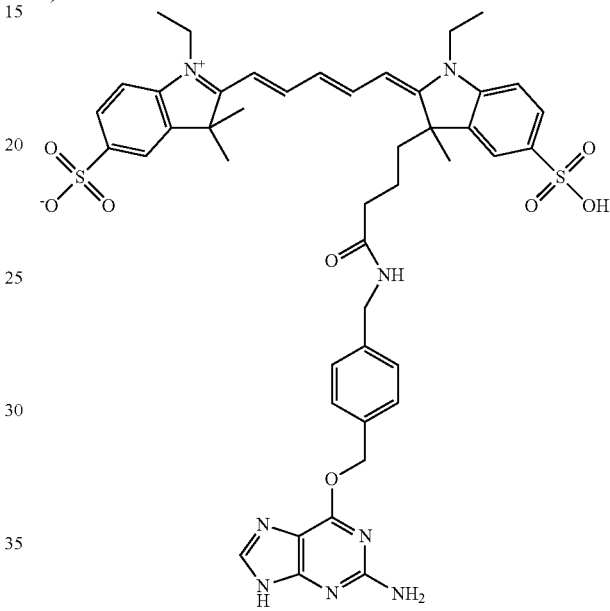

Structure of the Substrate BG-cis-cyclohexane-DY647 (compound 29):

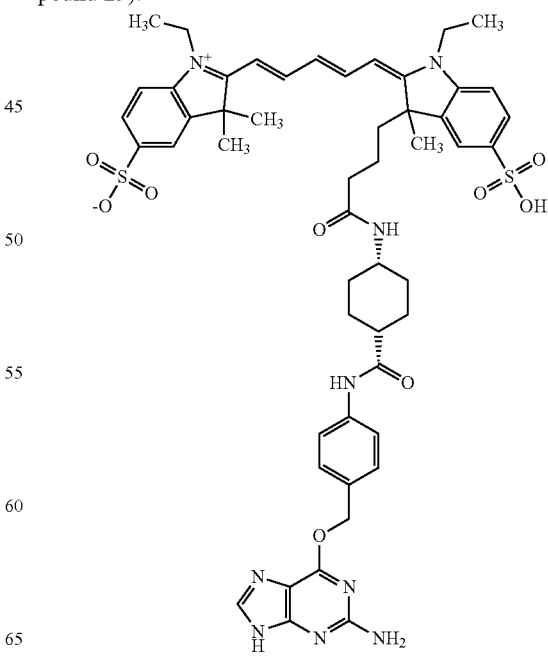

Results of enzymatic reactivity and of protein labeling in vitro

Figure 12:
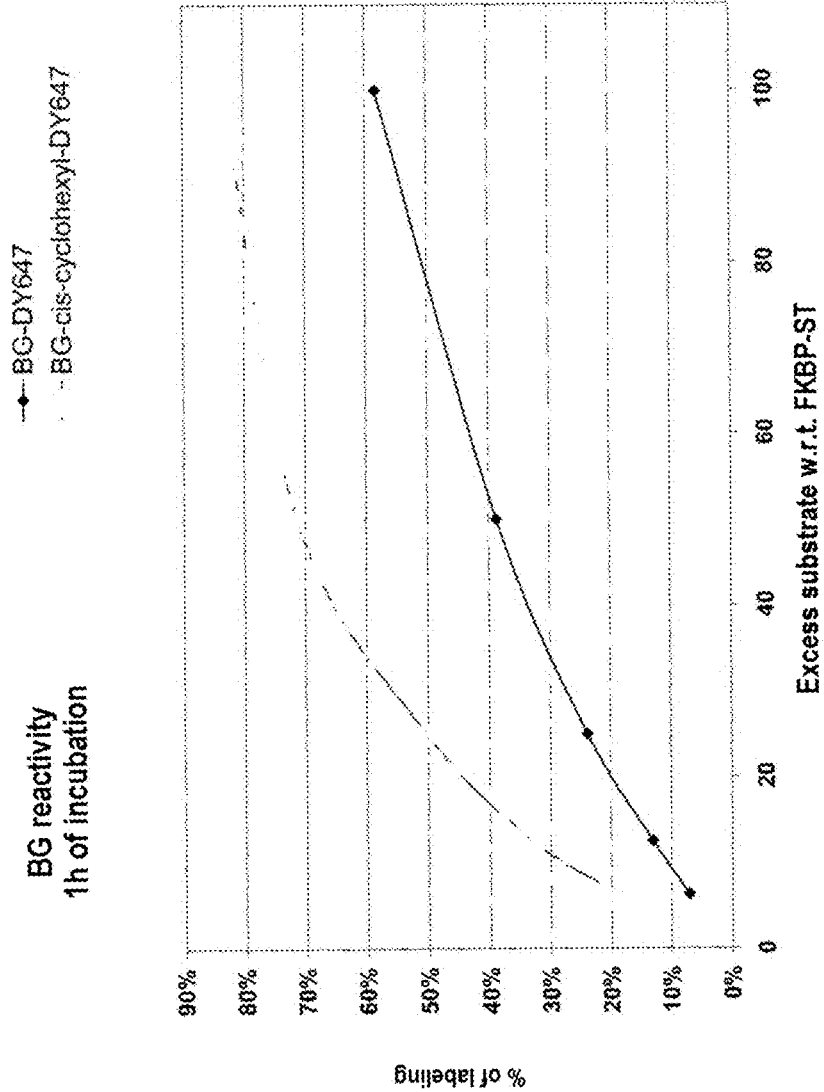

The curves from FIG. 12 show that the percentage of enzyme labeled after 1 h of incubation with substrates comprising a cis-cyclohexane unit is much better than that observed with the reference substrate, and this being regardless of the substrate concentration.

Example 10

BG-methylbenzamide-Atto465

Comparison of the reactivity of BG-Atto465/Bg-methylbenzamide-Atto465 with the SNAP-tag enzyme.
Structure of the Reference Substrate BG-Atto465 (Compound 35):

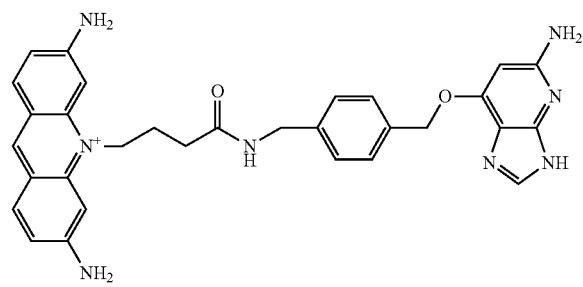 [SMILES: Nc1ccc2cc3ccc(N)cc3[n+](CCCC(=O)NCc3ccc(COc4cc(N)nc5[nH]cnc45)cc3)c2c1]

Structure of the Substrate BG-methylbenzamide-Atto465 (compound 36)

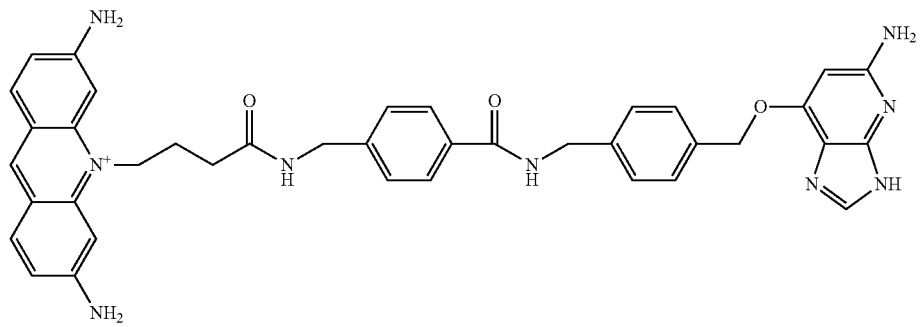

Results obtained on cell model

The labeling of a transmembrane protein expressed at the surface of living cells shows that the BG-methylbenzamide-Atto465 substrate has a much better reactivity with the SNAP-tag enzyme than the reference substrate. The half saturation concentration measured with BG-methylbenzamide-Atto465 is 213 nM whereas it is 1983 nM with the BG-Atto465 substrate.

The Syntheses of the Following Compounds are Described Below:
Compound 1: benzylguanine-Dy647
Compound 2: benzylguanine-5,6-carboxyfluorescein
Compound 3: benzylguanine-fluorescein-5-EX
Compound 4: benzylguanine-ATTO647N
Compound 5: benzylguanine-Tb(KR)
Compound 6: 4-((2,2,2-trifluoroacetamido)methyl)benzoic acid
Compound 7: trifluoroacetamidomethylbenzamide-BG
Compound 8: aminomethylbenzamide-BG
Compound 9: Dy647-methylbenzamide-BG
Compound 10: ATTO647N-methylbenzamide-BG
Compound 11: 56-carboxyfluorescein-methylbenzamide-BG
Compound 12: fluorescein-5-EX-benzylamide-BG
Compound 13: Tb(KR)-methylbenzamide-BG
Compound 14: BG-SH
Compound 15: BG-methylbenzamide-SH
Compound 16: 2-(trifluoroacetamidomethyl)nicotinic acid
Compound 17: 2-(trifluoroacetamidomethyl)isonicotinic acid
Compound 18: DY647-aminomethylisonicotinamide-benzylguanine
Compound 19: DY647-aminomethylnicotinamide-benzylguanine
Compound 20: Tb(KR)-aminomethylnicotinamide-benzylguanine
Compound 21: benzylguanine-N-Fmoc-piperidine
Compound 22: benzylguanine-piperidine
Compound 23: DY647-piperidine-benzylguanine
Compound 24: benzylguanine-trans-4-(Fmoc-amino)cyclohexane
Compound 25: benzylguanine-trans-4-aminocyclohexane
Compound 26: DY647-trans-cyclohexane-benzylguanine
Compound 27: benzylguanine-cis-4-(Fmoc-amino)cyclohexane
Compound 28: benzylguanine-cis-4-aminocyclohexane
Compound 29: DY647-cis-cyclohexane-benzylguanine
Compound 30: benzylcytosine-DY647
Compound 31: benzylcytosine-Tb(KR)
Compound 32: aminomethylbenzamide-BC
Compound 33: DY647-methylbenzamide-BC:
Compound 34: Tb(KR)-methylbenzamide-BC:
Compound 35: Atto465-BG:

Compound 36: Atto465-methylbenzamine-BG:

Compound 1: benzylguanine-DY647

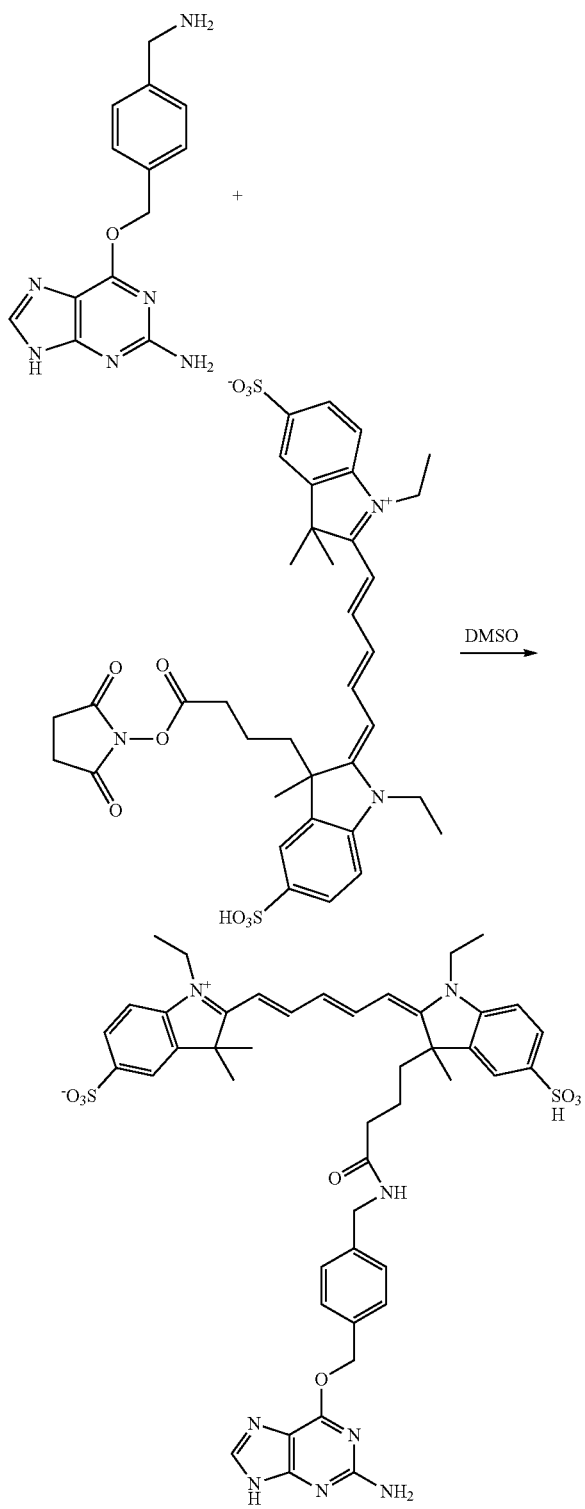

Introduced into a 10 ml round-bottomed flask were 4.2 mg (15.5 μmol) of 6-aminomethylbenzylguanine and 11.8 mg (15.5 μmol) of DY647-NHS. The products were partially solubilized in 4 ml of anhydrous dimethylsulfoxide.

The mixture was stirred for one hour. The reaction was monitored by HPLC on a Merck Lichrospher RP °18, 5 μm, 125×4.6 column with a gradient of acetonitrile in water containing 0.2% of trifluoroacetic acid.

A purification by preparative HPLC was carried out on a Vydac C18, 10 μm, 250×22 column with a gradient of acetonitrile in water containing 0.2% of trifluoroacetic acid.

The fractions were collected and concentrated under reduced pressure. A blue solid was obtained (8.5 mmol by optical density measurement, 55%) corresponding to the desired product.

MS (ES$^+$) m/z: [M+H$^+$] 895.3.

Compound 2: benzylguanine-5,6-carboxyfluorescein

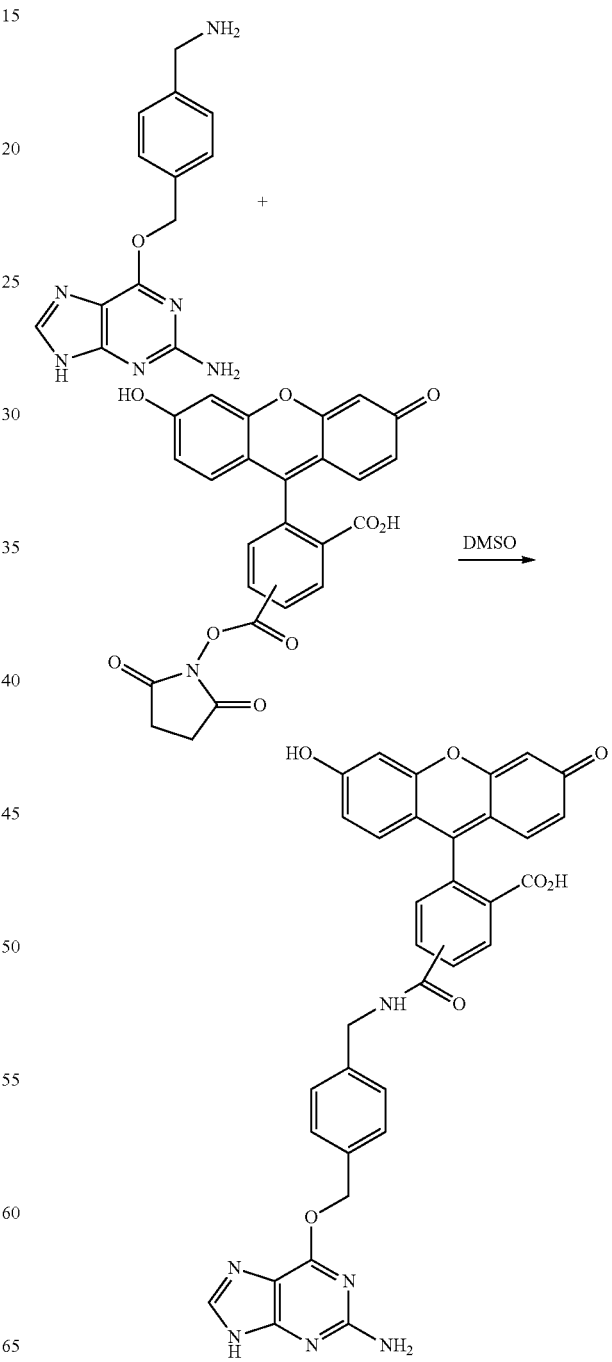

Introduced into a 1.5 ml Eppendorf tube were 100 µl of a solution containing 10 mmol·l⁻¹ of 6-aminomethylbenzylguanine in anhydrous dimethylsulfoxide (1 µmol) and 100 µl of a solution containing 10 mmol·l⁻¹ of 5,6-carboxyfluorescein-NHS in anhydrous dimethylsulfoxide (1 µmol).

The mixture was stirred for one hour. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A yellow solid was obtained (900 nmol by optical density measurement, 90%) corresponding to the desired product.

MS (ES⁺) m/z: [M+H⁺] 629.1.

Compound 3: benzylguanine-fluorescein 5-Ex

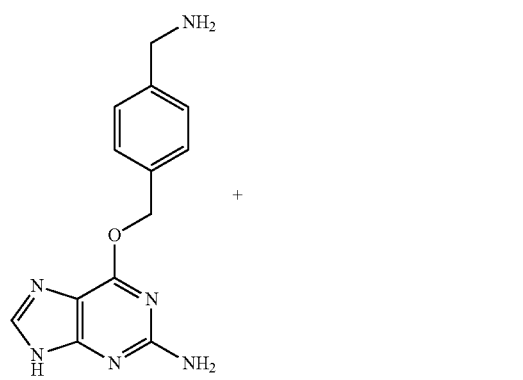

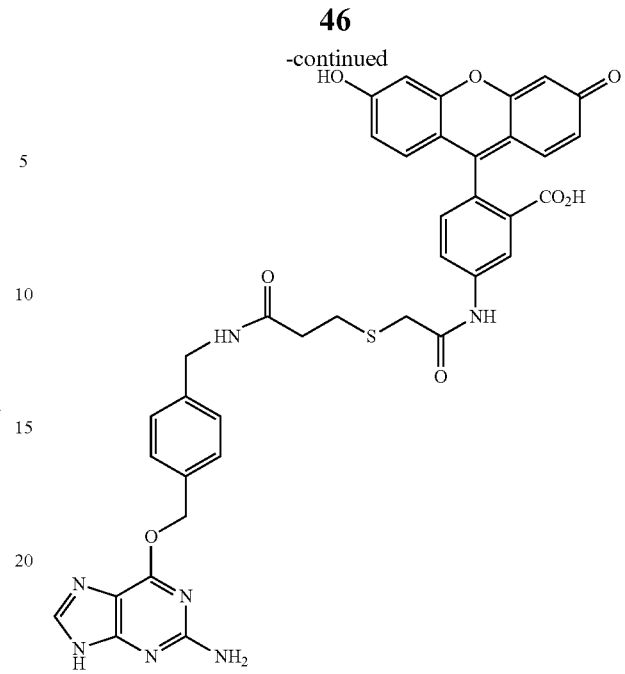

Introduced into a 1.5 ml Eppendorf tube were 100 µl of a solution containing 10 mmol·l⁻¹ of 6-aminomethylbenzylguanine in anhydrous dimethylsulfoxide (1 µmol) and 100 µl of a solution containing 10 mmol·l⁻¹ of fluorescein-5-EX-NHS in anhydrous dimethylsulfoxide (1 µmol). The mixture was stirred for one hour. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A yellow solid was obtained (650 nmol by optical density measurement, 65%) corresponding to the desired product.

MS (ES⁺) m/z: [M+H⁺] 746.1.

Compound 4: benzylguanine-ATTO647N

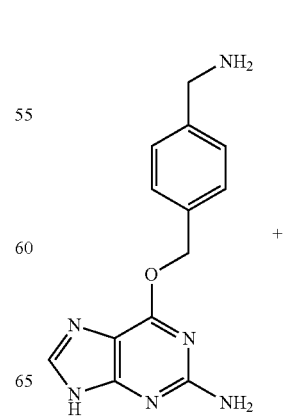

-continued

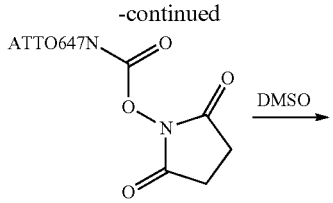

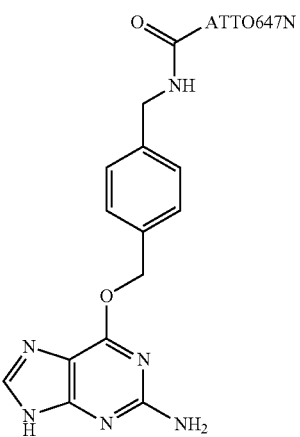

Introduced into a 10 ml round-bottomed flask were 1.8 mg (6.7 µmol) of 6-aminomethylbenzylguanine and 5 mg (6.6 µmol) of ATTO647-NHS. The products were partially solubilized in 5 ml of anhydrous dimethylsulfoxide.

The mixture was stirred for one hour. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A blue solid was obtained (3.6 µmol by optical density measurement, 54.5%) corresponding to the desired product.

MS (ES$^+$) m/z: [M$^+$] 898.

Compound 5: benzylguanine-Tb(KR)

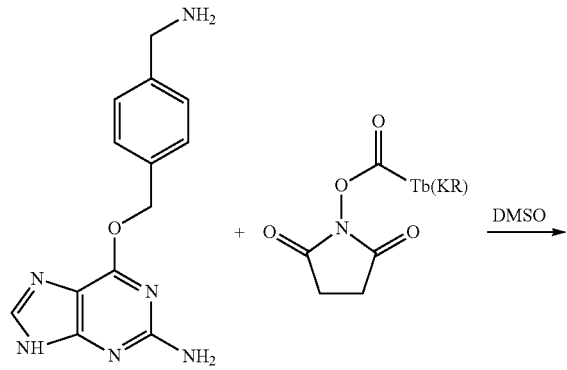

-continued

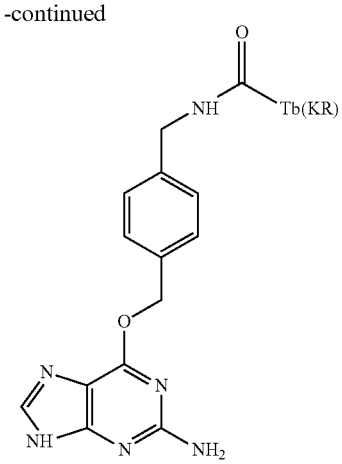

Introduced into a 1.5 ml Eppendorf tube were 100 µl of a solution containing 10 mmol·l$^{-1}$ of 6-aminomethylbenzylguanine in anhydrous dimethylsulfoxide (1 µmol) and 100 µl of a solution containing 10 mmol·l$^{-1}$ of Tb(KR)-NHS in anhydrous dimethylsulfoxide (1 µmol). The mixture was stirred for one hour. The reaction was monitored by HPLC on a Merck Lichrospher RP °18, 5 µm, 125×4.6 column with a gradient of acetonitrile in water containing 25 mM of triethylammonium acetate.

A purification by preparative HPLC was carried out on a Vydac C18, 10 µm, 250×22 column with a gradient of acetonitrile in water containing 25 mM of triethylammonium acetate.

The fractions were collected and concentrated under reduced pressure. A white solid was obtained (650 nmol by optical density measurement, 65%) corresponding to the desired product.

MS (ES$^+$) m/z: [M+H$^+$] 1685.6.

Compound 6:
4-((2,2,2-trifluoroacetamido)methyl)benzoic acid

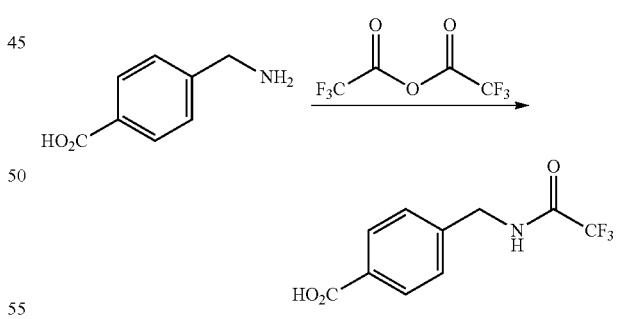

Weighed into a 100 ml round-bottomed flask were 2.38 g (15.7 mmol) of 4-(aminomethyl)benzoic acid. The round-bottomed flask was put into a bath of water and ice and 5.6 ml (59 mmol) of trifluoroacetic anhydride were slowly added. At the end of the addition, the reaction mixture was left to return to ambient temperature and the reaction mixture was left stirring for two hours.

16.5 ml of water at 4° C. were added. The precipitate was filtered over a frit, rinsed with 2×3 ml of water at 4° C. and dried under vacuum in the presence of phosphorus pentoxide for 48 h.

A white solid (3.27 g-13.2 mmol—84%) was obtained corresponding to the desired product.
MS (ES⁻) m/z: [M−H⁺] 246.2.

Compound 7:
trifluoroacetamidomethylbenzamide-BG

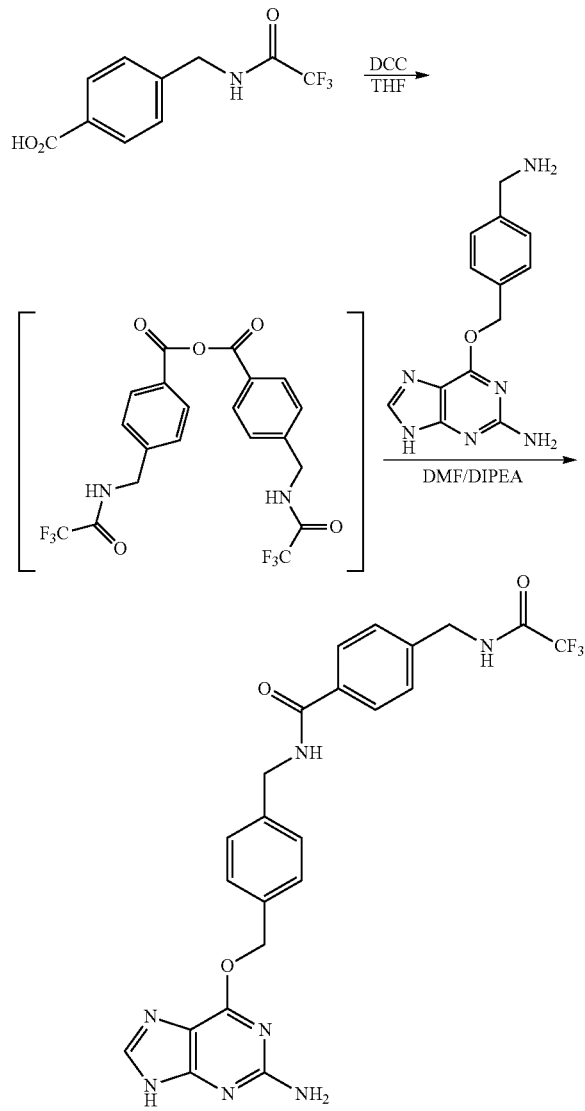

Weighed into a 10 ml round-bottomed flask were 593 mg (2.4 mmol) of trifluoroacetamidomethyl benzoic acid. This acid was dissolved in 4 ml of anhydrous tetrahydrofuran and 324.4 mg (1.2 mmol) of 1,3-dicyclohexylcarbodiimide were added. It was left stirring, at ambient temperature, for 2 hours. The white precipitate of dicyclohexylurea obtained was filtered over a frit.

Weighed into a 25 ml round-bottomed flask were 162.2 mg (0.6 mmol) of 6-aminobenzylguanine and 2 ml of anhydrous dimethylformamide were added. Next, the solution of trifluoroacetamidomethylbenzoic anhydride in THF and 200 μl of diisopropylethylamine were added. The reaction mixture was left, stirring, at ambient temperature for two hours. The reaction was monitored by HPLC on a Merck Lichrospher RP °18, 5 μm, 125×4.6 column with a gradient of acetonitrile in water containing 0.2% of trifluoroacetic acid.

The reaction mixture was evaporated to dryness under reduced pressure until a yellow solid was obtained. It was triturated in 5 ml of acetonitrile and filtered over a frit. It was then rinsed with 2×1 ml of acetonitrile and dried under vacuum for 48 h.

A beige solid (289 mg-0.58 mmol—96%) was obtained corresponding to the desired product. MS (ES⁺) m/z: [M+H⁺] 500.1.

Compound 8: aminomethylbenzamide-BG

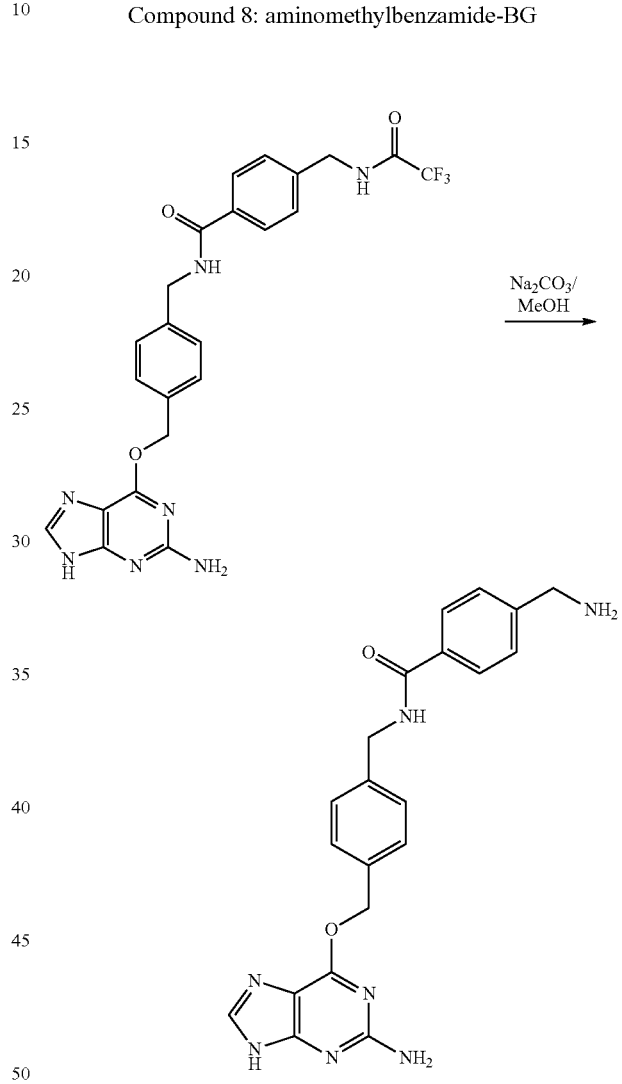

Weighed into a 50 ml round-bottomed flask were 25 mg (50 μmol) of N-(4-((2-amino-9H-purin-6-yloxy)methyl)benzyl)-4-((2,2,2-trifluoroacetamido)methyl)benzamide. 10 ml of methanol, 2 ml of an aqueous solution saturated with Na₂CO₃ and 4 ml of water were added. It was left stirring overnight at ambient temperature. The deprotection was monitored by HPLC on a Merck Lichrospher RP °18, 5 μm, 125×4.6 column with a gradient of acetonitrile in water containing 0.2% of trifluoroacetic acid.

A purification by preparative HPLC was carried out on a Vydac C18, 10 μm, 250×22 column with a gradient of acetonitrile in water containing 0.2% of trifluoroacetic acid.

The fractions were collected and concentrated under reduced pressure. A white solid (17.5 mg-43 μmol—87%) was obtained corresponding to the desired product.
MS (ES⁺) m/z: [M+H⁺] 404.3.

Compound 9: DY647-methylbenzamide-BG

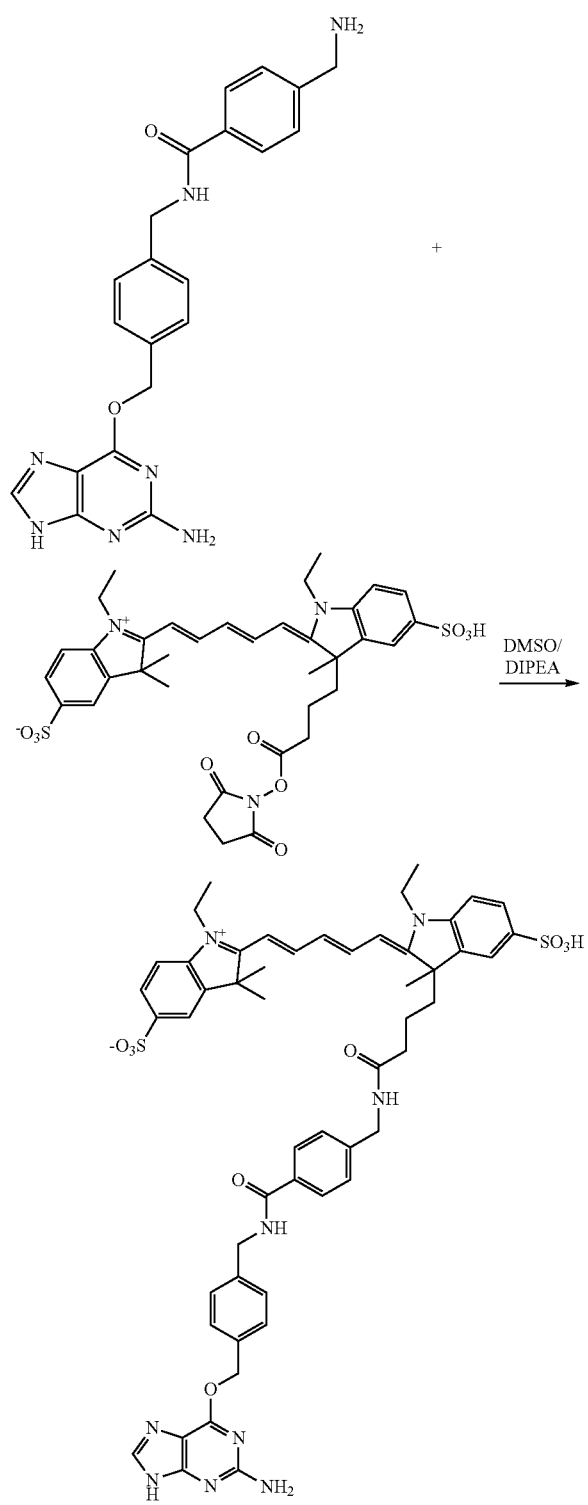

2 μmol of aminomethylbenzamide-BG were taken up in 100 μl of anhydrous dimethylsulfoxide. 2 μmol of DY647-NHS in solution in 300 μl of anhydrous dimethylsulfoxide and 2 μl of diisopropylethylamine were added. It was left stirring for two hours at ambient temperature.

The reaction was monitored by HPLC on a Merck Lichrospher RP °18, 5 μm, 125×4.6 column with a gradient of acetonitrile in water containing 0.2% of trifluoroacetic acid.

A purification by preparative HPLC was carried out on a Vydac C18, 10 μm, 250×22 column with a gradient of acetonitrile in water containing 0.2% of trifluoroacetic acid.

The fractions were collected and concentrated under reduced pressure. A blue solid was obtained (1 μmol by optical density measurement, 50%) corresponding to the desired product. MS (ES+) m/z: [M+H+] 1028.4.

Compound 10: ATTO647N-methylbenzamide-BG

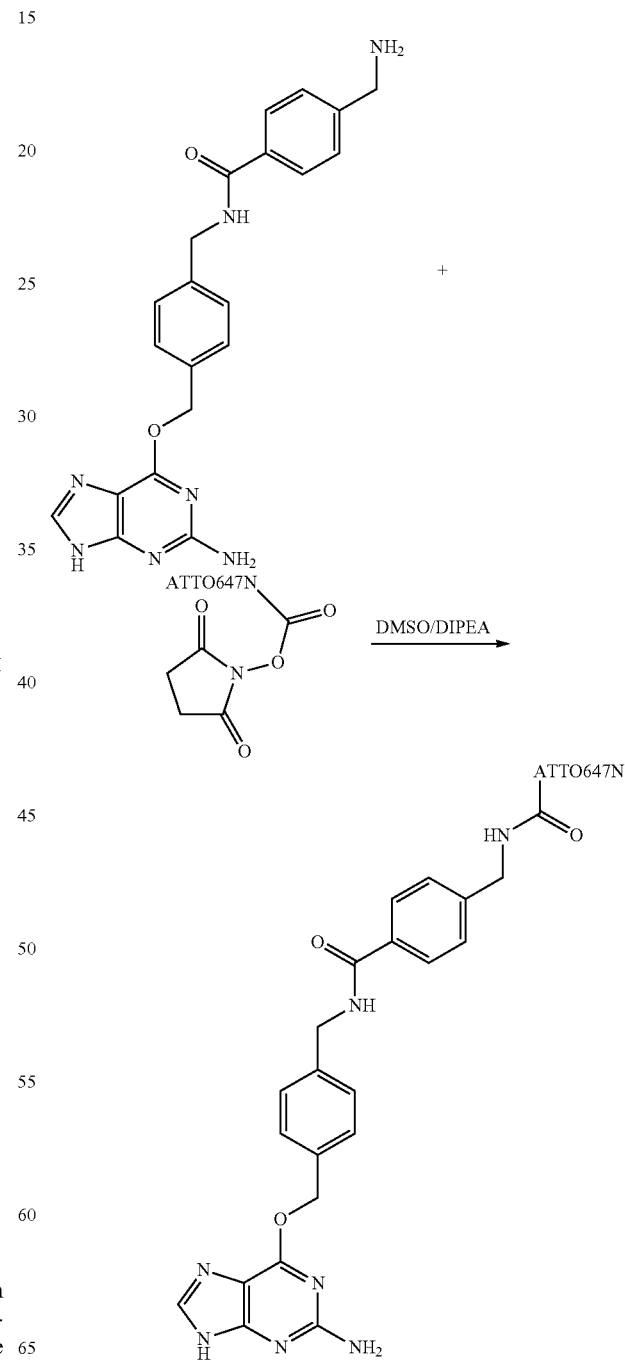

200 nmol of aminomethylbenzamide-BG were taken up in 100 µl of anhydrous dimethylsulfoxide. 200 nmol of ATTO647N-NHS in solution in 20 µl of anhydrous dimethylsulfoxide and 1 µl of diisopropylethylamine were added. The reaction mixture was left stirring for two hours at ambient temperature.

The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A blue solid was obtained (149 nmol by optical density measurement, 74%) corresponding to the desired product. MS (ES$^+$) m/z: [M$^+$] 1031.5.

Compound 11:
5,6-carboxyfluorescein-methylbenzamide-BG

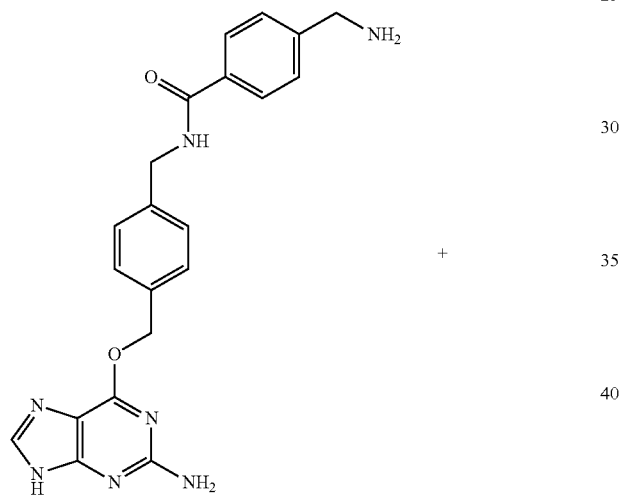

+

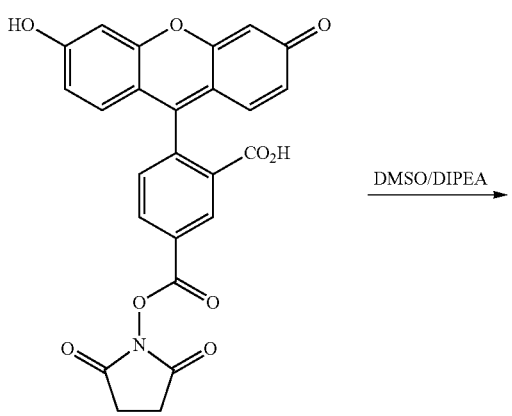

DMSO/DIPEA →

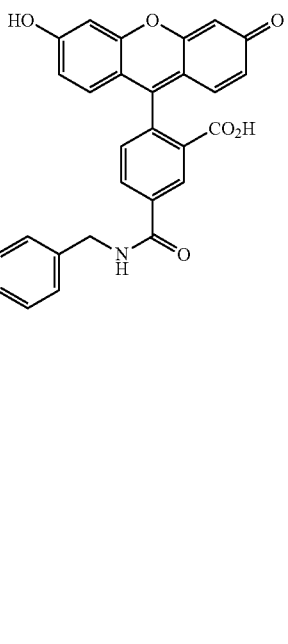

1 µmol of aminomethylbenzamide-BG were taken up in 100 µl of anhydrous dimethylsulfoxide (DMSO). 1 µmol of 5,6-carboxyfluorescein-NHS in solution in 50 µl of anhydrous dimethylsulfoxide and 2 µl of diisopropylethylamine were added. The reaction mixture was left stirring for one hour at ambient temperature.

The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A yellow solid was obtained (600 nmol by optical density measurement, 60%) corresponding to the desired product.

MS (ES$^+$) m/z: [M+H$^+$] 762.1.

Compound 12: fluorescein-5-EX-benzylamide-BG

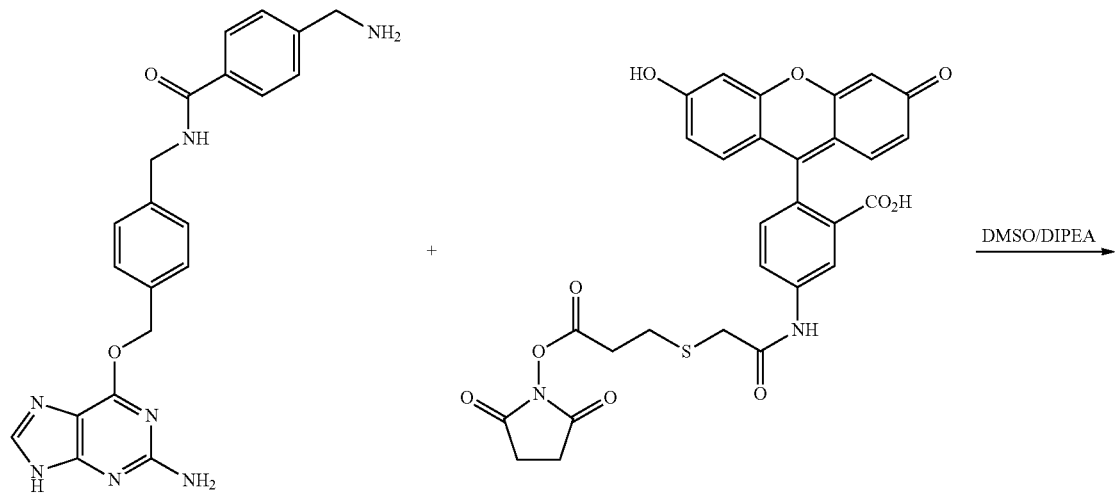

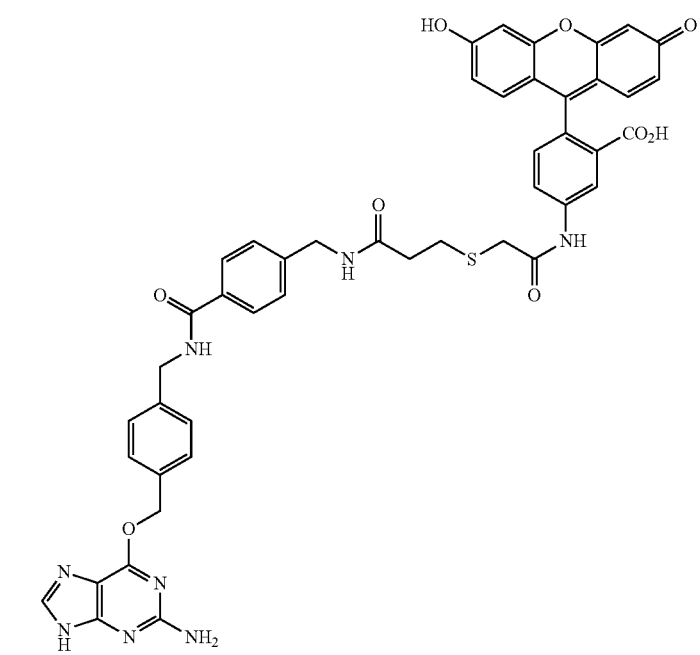

1 µmol of aminomethylbenzamide-BG was taken up in 100 µl of anhydrous dimethylsulfoxide. 1 µmol of fluorescein-5-EX-NHS in solution in 40 µl of anhydrous dimethylsulfoxide and 2 µl of diisopropylamine were added. The reaction mixture was left stirring for one hour at ambient temperature.

The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A yellow solid was obtained (400 nmol by optical density measurement, 40%) corresponding to the desired product.

MS (ES$^+$) m/z: [M+H$^+$] 879.3.

Compound 13: Tb(KR)-methylbenzamide-BG

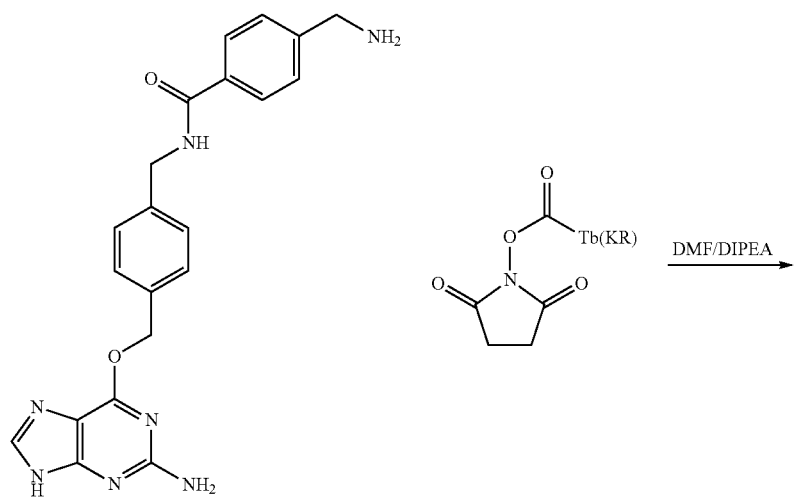

Weighed into a 10 ml round-bottomed flask were 2.3 mg (8.5 μmol) of aminomethylbenzamide-BG in 2 ml of anhydrous dimethylformamide. 6 μmol of Tb(KR)-NHS in solution in 2 ml of anhydrous dimethylformamide and 20 μl of diisopropylamine were added. The reaction mixture was left stirring for two hours at ambient temperature. The reaction was monitored by HPLC on a Merck Lichrospher RP °18, 5 μm, 125×4.6 column with a gradient of acetonitrile in water containing 25 mM of triethylammonium acetate, pH 6.

The DMF was evaporated under reduced pressure and the residue was taken up in water. A purification by preparative HPLC was carried out on a Vydac C18, 10 μm, 250×22 column with a gradient of acetonitrile in water containing 25 mM of triethylammonium acetate, pH 6.

The fractions were collected and concentrated under reduced pressure. A white solid (2.2 μmol by optical density measurement, 36%) was obtained corresponding to the desired product. MS (ES⁺) m/z: [M+H⁺] 1819.3.

Compound 14: Preparation of BG-SH

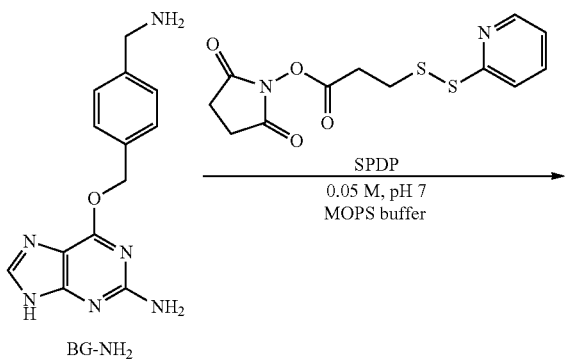

59
-continued

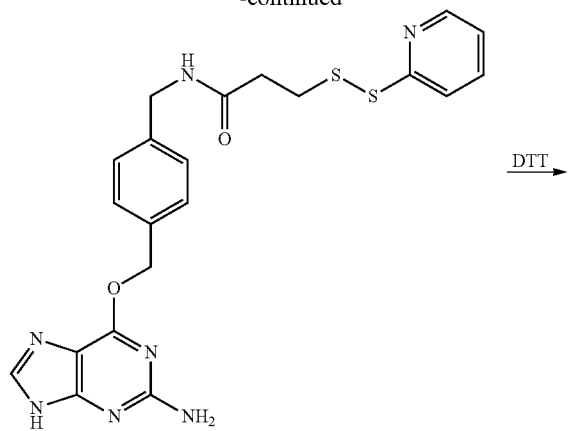

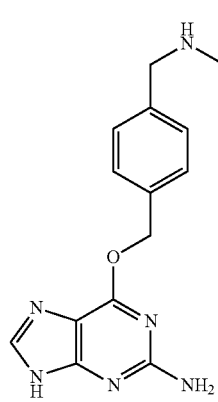

BG-SH

Weighed into a 10 ml round-bottomed flask were 0.8 mg (3 μmol) of 6-aminomethylbenzylguanine that was dissolved in 200 μl of anhydrous dimethylformamide and 1.5 ml of 0.05 M, pH 7, MOPS buffer. 1.1 mg (3.6 μmol) of SPDP were added. The reaction mixture was left stirring for one hour. The reaction was monitored by HPLC on a Merck Lichrospher RP °18, 5 μm, 125×4.6 column with a gradient of acetonitrile in water containing 0.2% of trifluoroacetic acid.

Added to the reaction mixture were 2.2 mg (14.4 μmol) of DTT and this reaction mixture was left stirring for two hours. The reaction was monitored by HPLC.

A purification by preparative HPLC was carried out on a Vydac C18, 10 μm, 250×22 column with a gradient of acetonitrile in water containing 0.2% of trifluoroacetic acid.

The fractions were collected and concentrated under reduced pressure. A white solid was obtained (2.1 μmol by optical density measurement, 70%) corresponding to the desired product. (ES+) m/z: [M+H+] 358.9.

60
Compound 15: BG-methylbenzamide-SH

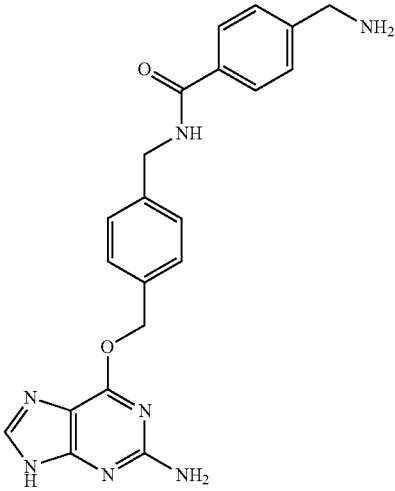

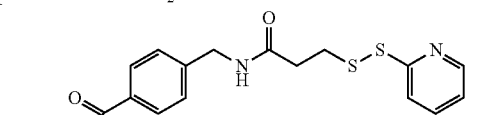

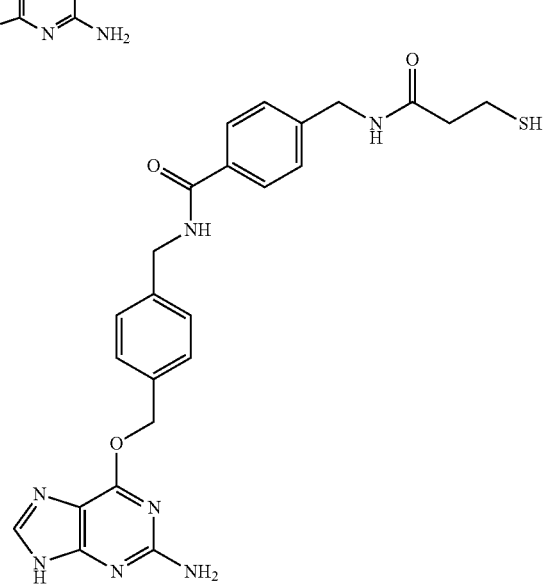

In a 10 ml round-bottomed flask, 4.5 μmol of aminomethylbenzamide-benzylguanine were taken up in 200 μl of anhydrous dimethylformamide and 1.5 ml of 0.05 M, pH 7, MOPS buffer. 1.7 mg (5.4 μmol) of SPDP were added. The reaction mixture was left stirring for one hour. The reaction was monitored by HPLC on a Merck Lichrospher RP °18, 5 μm, 125×4.6 column with a gradient of acetonitrile in water containing 0.2% of trifluoroacetic acid.

Added to the reaction mixture were 2.5 mg (16.2 μmol) of DTT and this reaction mixture was left stirring for two hours. The reaction was monitored by HPLC.

A purification by preparative HPLC was carried out on a Vydac C18, 10 μm, 250×22 column with a gradient of acetonitrile in water containing 0.2% of trifluoroacetic acid.

The fractions were collected and concentrated under reduced pressure. A white solid was obtained (3 μmol by optical density measurement, 66%) corresponding to the desired product.

MS (ES$^+$) m/z: [M+H$^+$] 492.2.

Compound 16:
2-(trifluoroacetamidomethyl)nicotinic acid

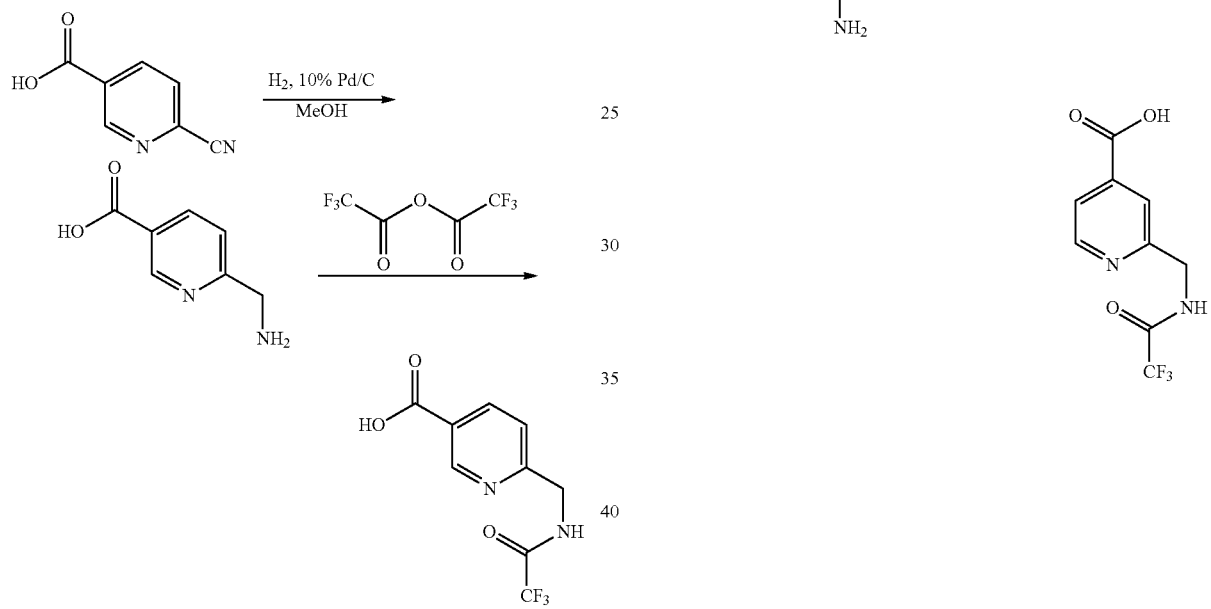

Compound 17:
2-(trifluoroacetamidomethyl)isonicotinic acid

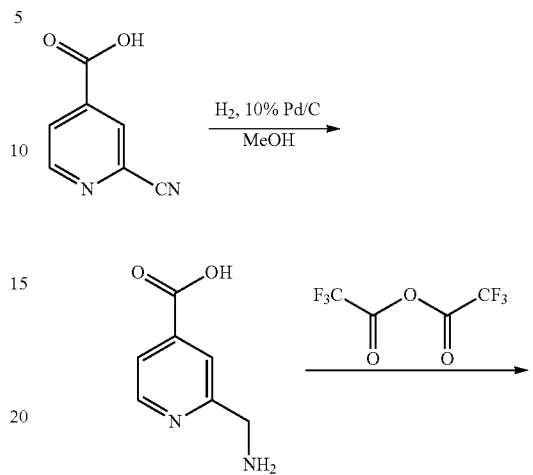

Weighed into a 100 ml round-bottomed flask were 500 mg (3.58 μmol) of 6-cyanopyridine-3-carboxylic acid which was dissolved in 50 ml of methanol. Added next were 30 mg of 10% palladium on carbon and hydrogen at one atmosphere for four hours. The reaction is followed by HPLC on a Merck Lichrospher RP °18, 5 μm, 125×4.6 column with a gradient of acetonitrile in water containing 0.2% of trifluoroacetic acid. The product formed was precipitated.

40 ml of demineralized water were added to the reaction mixture, then the palladium was filtered over Celite and the reaction mixture was concentrated under reduced pressure in a 50 ml round-bottomed flask. The round-bottomed flask was placed in an ice/water bath and 4 ml of trifluoroacetic anhydride were slowly added. The reaction mixture was left to return to ambient temperature under stirring for two hours. The reaction was monitored by HPLC.

20 ml of ether were added to the reaction mixture and it was placed in an ice/water bath for 20 min. The precipitate was filtered over a frit and it was dried under vacuum for 48 h.

A white solid (450 mg-1.81 mmol—54%) was obtained corresponding to the desired product. MS (ES$^+$) m/z: [M+H$^+$] 249.

Weighed into a 50 ml round-bottomed flask were 100 mg (675 μmol) of 6-cyanopyridine-4-carboxylic acid which was dissolved in 30 ml of methanol. Added next were 10 mg of 10% palladium on carbon and hydrogen at one atmosphere for four hours. The reaction was followed by HPLC on a Merck Lichrospher RP °18, 5 μm, 125×4.6 column with a gradient of acetonitrile in water containing 0.2% of trifluoroacetic acid. The product formed was precipitated.

20 ml of demineralized water were added to the precipitate, the palladium was filtered over Celite and the mixture was concentrated under reduced pressure in a 50 ml round-bottomed flask. The round-bottomed flask was placed in an ice/water bath and 3 ml of trifluoroacetic anhydride were slowly added. The reaction mixture was left to return to ambient temperature and was kept stirring for two hours. The reaction was monitored by HPLC.

10 ml of ether were added to the reaction mixture and it was placed in an ice/water bath for 20 min. The precipitate was filtered over a frit and it was dried under vacuum for 48 h.

A white solid (110 mg-443 mmol—67%) was obtained corresponding to the desired product.

MS (ES$^+$) m/z: [M+H$^+$] 249.

Compound 18:
DY647-aminomethylisonicotinamide-benzylguanine

Compound 19:
DY647-aminomethylnicotinamide-benzylguanine

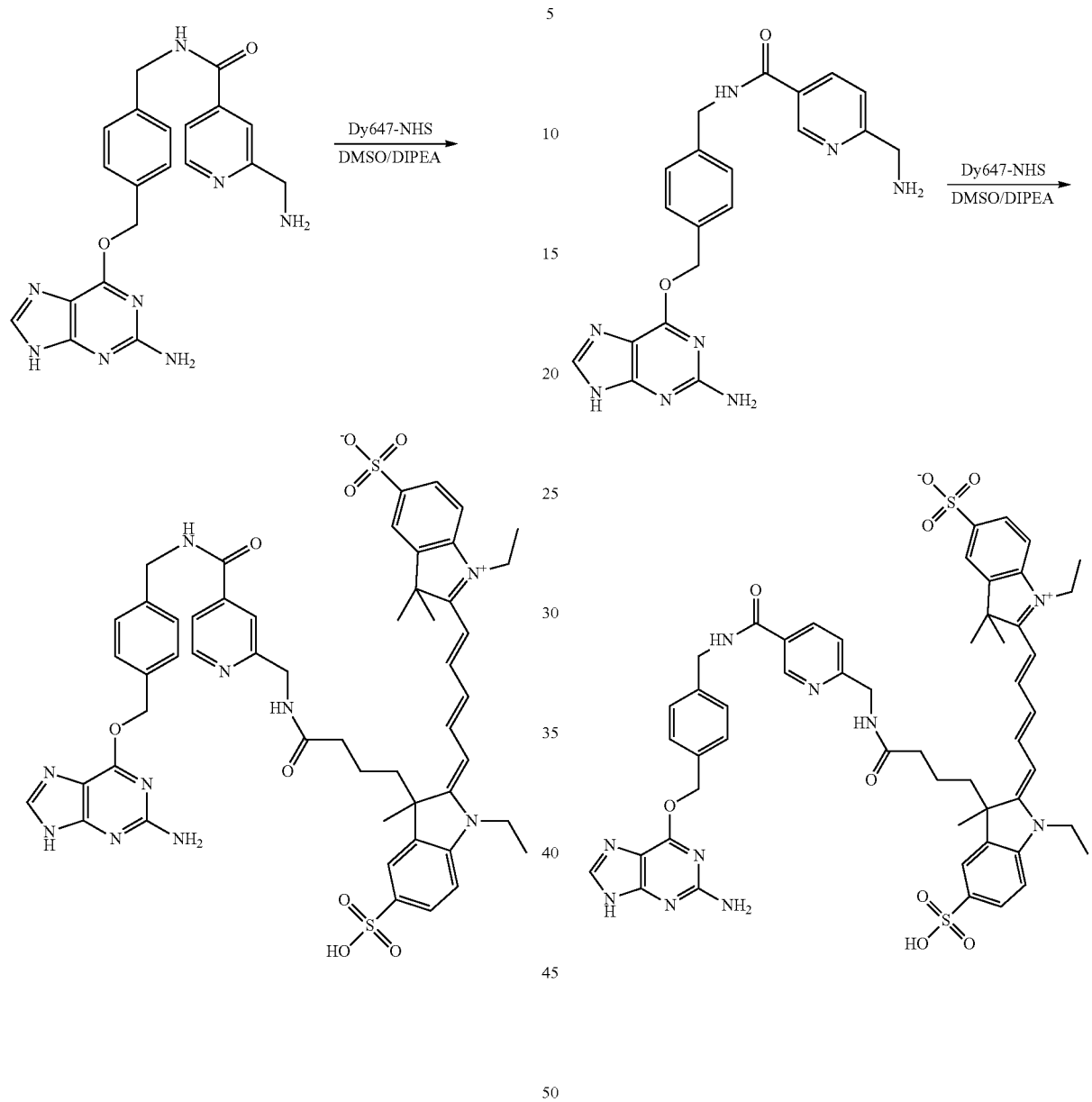

Added to a 1.5 ml Eppendorf tube containing 1 µmol of aminomethylisonicotinamide-benzylguanine was a solution of 1 µmol of Dy647-NHS in 100 µl of anhydrous dimethylsulfoxide and 2 µl of diisopropylethylamine. The reaction mixture was left stirring for one hour. The reaction was monitored by HPLC on a Merck Lichrospher RP °18, 5 µm, 125× 4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A blue solid was obtained (470 nmol by optical density measurement, 47%) corresponding to the desired product. MS (ES$^+$) m/z: [M+H$^+$] 1029.3.

Added to a 1.5 ml Eppendorf tube containing 1 µmol of aminomethylnicotinamide-benzylguanine was a solution of 1 µmol of Dy647-NHS in 100 µl of anhydrous dimethylsulfoxide and 2 µl of diisopropylethylamine. The reaction mixture was left stirring for one hour. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A blue solid was obtained (540 nmol by optical density measurement, 54%) corresponding to the desired product. MS (ES$^+$) m/z: [M+H$^+$] 1029.3.

Compound 20: Tb(KR)-aminomethylnicotinamide-benzylguanine

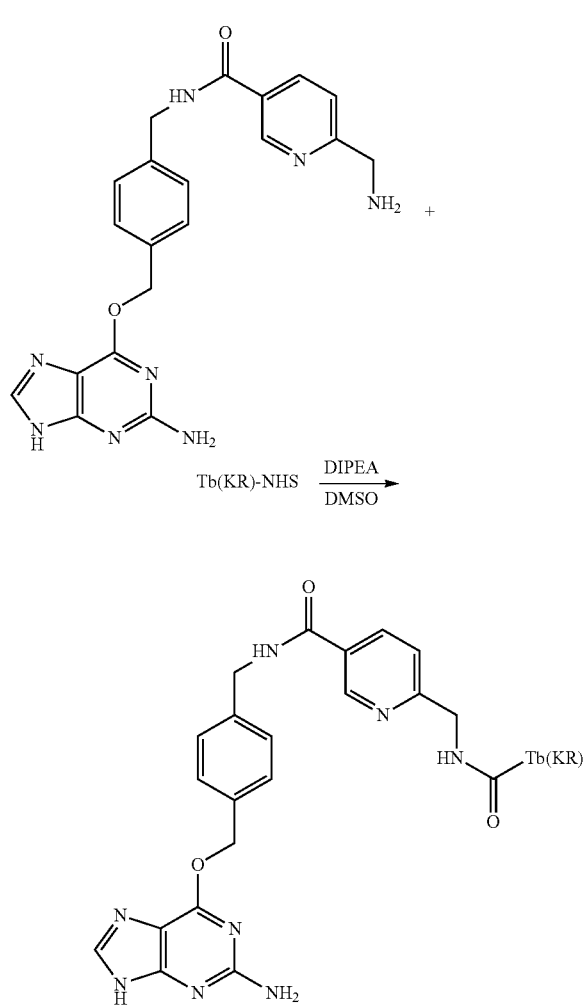

Compound 21: benzylguanine-N-Fmoc-piperidine

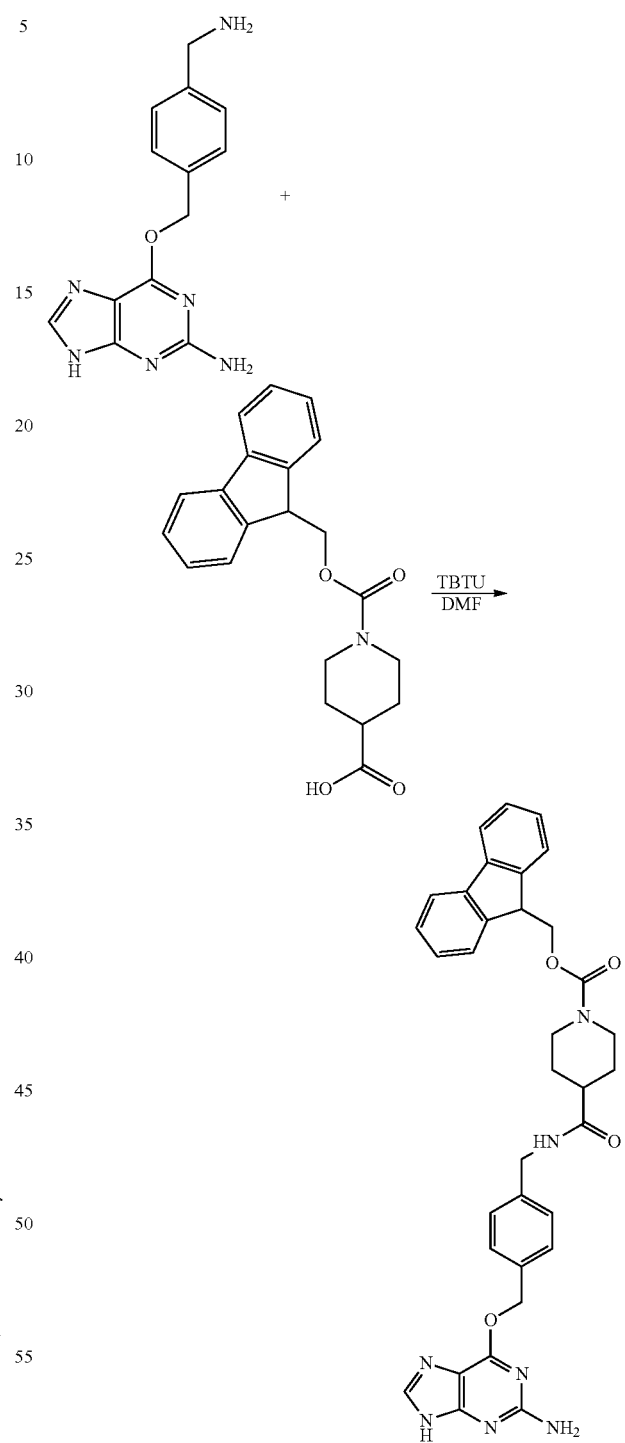

Added to a 1.5 ml Eppendorf tube containing 1 µmol of aminomethylnicotinamide-benzylguanine was a solution of 1 µmol of Tb(KR)-NHS in 100 µl of anhydrous dimethylsulfoxide and 2 µl of diisopropylethylamine. The reaction mixture was left stirring for one hour. The reaction was monitored by HPLC on a Merck Lichrospher RP °18, 5 µm, 125×4.6 column with a gradient of acetonitrile in water containing 25 mM of triethylammonium acetate, pH 6.

A purification by preparative HPLC was carried out on a Vydac C18, 10 µm, 250×22 column with a gradient of acetonitrile in water containing 25 mM of triethylammonium acetate, pH 6.

The fractions were collected and concentrated under reduced pressure. A blue solid was obtained (400 nmol by optical density measurement, 40%) corresponding to the desired product. MS (ES$^+$) m/z: [M+H$^+$] 1820.3-[M+2H$^+$]/2=910.5.

Weighed into a 50 ml round-bottomed flask were 48.1 mg (178 µmol) of 6-aminomethylbenzylguanine which was partially dissolved in 10 ml of anhydrous dimethylformamide. 62.5 mg (178 µmol) of 4-carboxy-N-Fmoc-piperidine and 57.1 mg (178 µmol) of TBTU were added. The reaction mixture was left stirring for two hours. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A white solid (38 mg, 35%) was obtained corresponding to the desired product. MS (ES$^+$) m/z: [M+H$^+$] 604.5.

Compound 22: benzylguanine-piperidine

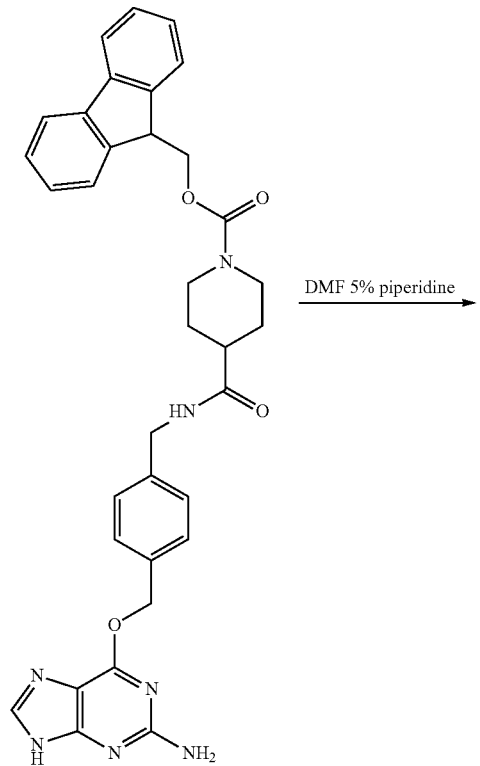

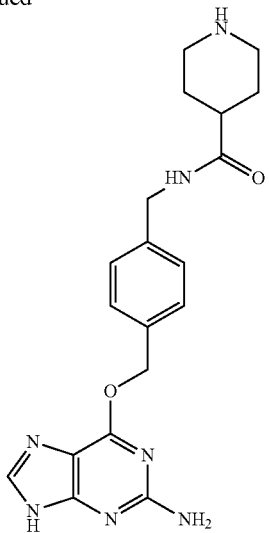

Weighed into a 1.5 ml Eppendorf tube were 1.8 mg (3 µmol) of benzylguanine-N-Fmoc-piperidine which was dissolved in 190 µl of anhydrous dimethylformamide. 10 µl of piperidine were added and the reaction mixture was left stirring for one hour. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A white solid was obtained corresponding to the desired product. It was used directly in the following reaction without measuring the yield. MS (ES$^+$) m/z: 382.3.

Compound 23: DY647-piperidine-benzylguanine

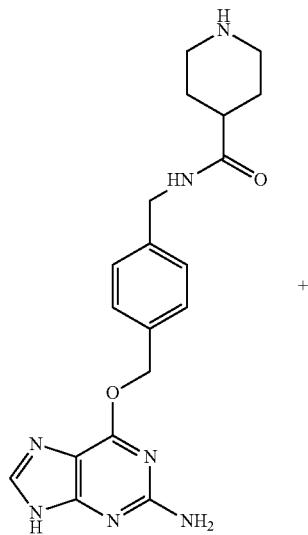

+

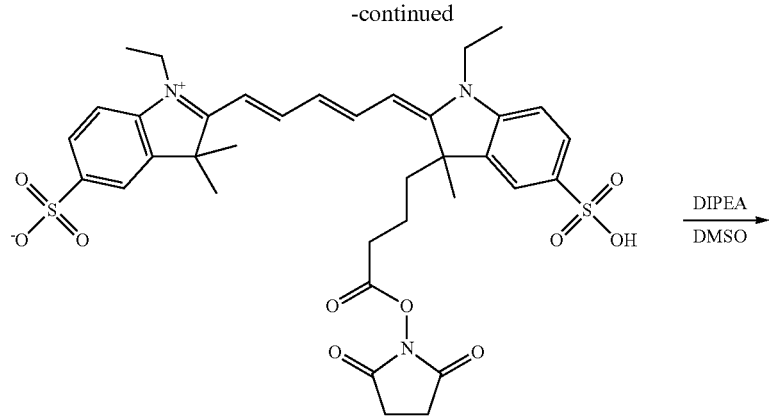

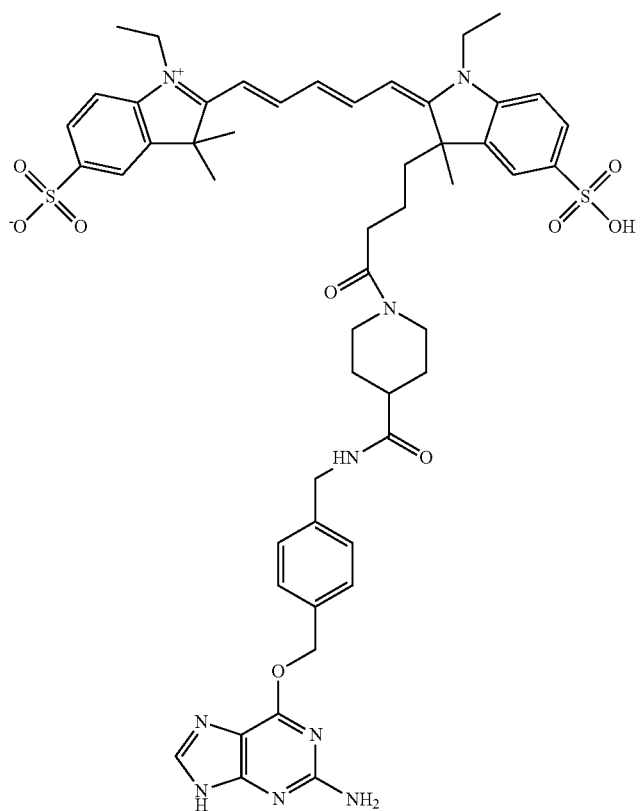

Added to a 25 ml round-bottomed flask containing 1.8 μmol of benzylguanine-piperidine were 800 μl of anhydrous dimethylsulfoxide, 4 μl of diisopropylethylamine and 0.14 mg (1.8 μmol) of Dy647-NHS. The reaction mixture was left stirring for one hour. The reaction was monitored by HPLC on a Merck Lichrospher RP °18, 5 μm, 125×4.6 column with a gradient of acetonitrile in water containing 0.2% of trifluoroacetic acid.

A purification by preparative HPLC was carried out on a Vydac C18, 10 μm, 250×22 column with a gradient of acetonitrile in water containing 0.2% of trifluoroacetic acid.

The fractions were collected and concentrated under reduced pressure. A blue solid was obtained (700 nmol by optical density measurement, 40%) corresponding to the desired product. MS (ES$^+$) m/z: 1006.75.

Compound 24:
benzylguanine-trans-4-(Fmoc-amino)cyclohexane

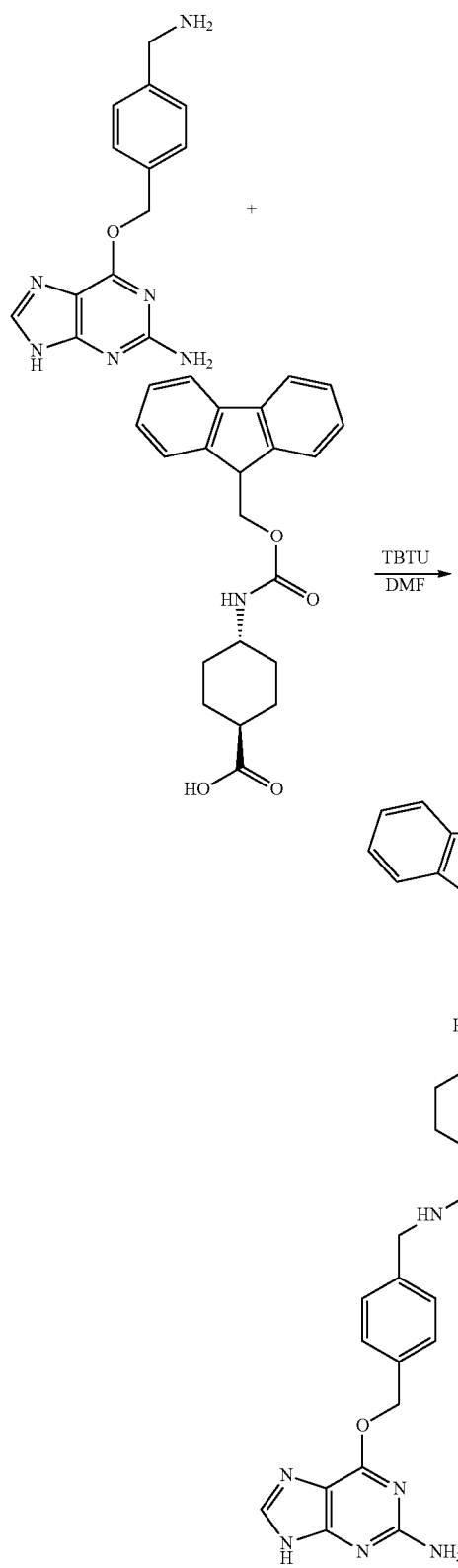

Weighed into a 50 ml round-bottomed flask were 51 mg (189 μmol) of 6-aminomethylbenzylguanine which was partially dissolved in 20 ml of anhydrous dimethylformamide. 69 mg (189 μmol) of trans-4-(Fmoc-amino)carboxycyclohexane and 60.7 mg (189 μmol) of TBTU were added. The reaction mixture was left stirring for two hours. The reaction was monitored by HPLC on a Merck Lichrospher RP °18, 5 μm, 125×4.6 column with a gradient of acetonitrile in water containing 0.2% of trifluoroacetic acid.

A purification by preparative HPLC was carried out on a Vydac C18, 10 μm, 250×22 column with a gradient of acetonitrile in water containing 0.2% of trifluoroacetic acid.

The fractions were collected and concentrated under reduced pressure. A white solid (16 mg, 13.7%) was obtained corresponding to the desired product.

MS (ES$^+$) m/z: [M+H$^+$] 618.6.

Compound 25:
benzylguanine-trans-4-aminocyclohexane

Weighed into a 1.5 ml Eppendorf tube were 1.2 mg (2 µmol) of benzylguanine-trans-4-(Fmoc-amino)cyclohexane which was dissolved in 190 µl of anhydrous dimethylformamide. 10 µl of piperidine were added and the reaction mixture was left stirring for one hour. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A white solid was obtained corresponding to the desired product. It was used directly in the following reaction without measuring the yield.

MS (ES$^+$) m/z: 396.3.

Compound 26:
DY647-trans-cyclohexane-benzylguanine

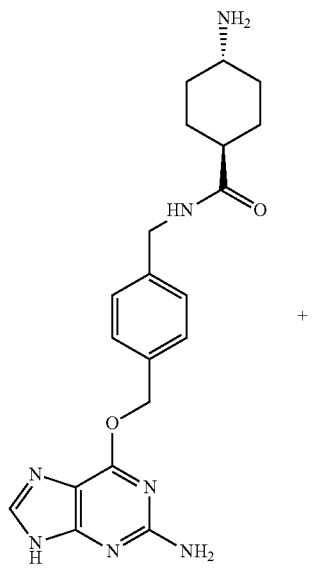

+

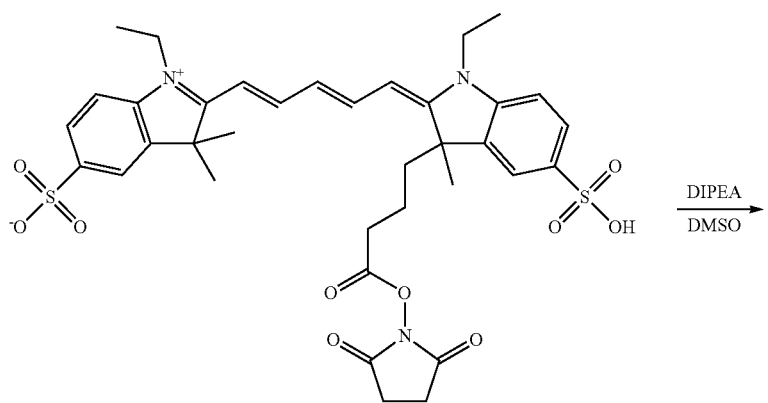

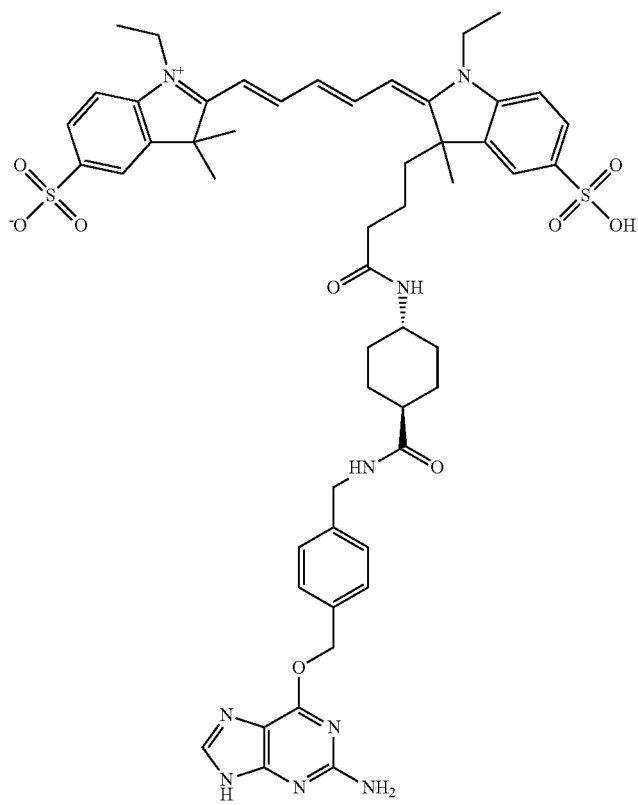

Added to a 25 ml round-bottomed flask containing 2 µmol of benzylguanine-trans-4-aminocyclohexane were 800 µl of anhydrous dimethylsulfoxide, 4 µl of diisopropylethylamine and 0.14 mg (1.8 µmol) of DY647-NHS. The reaction mixture was left stirring for one hour. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A blue solid was obtained (600 nmol by optical density measurement, 33%) corresponding to the desired product.

MS (ES$^+$) m/z: 1020.8.

Compound 27:
benzylguanine-cis-4-(Fmoc-amino)cyclohexane

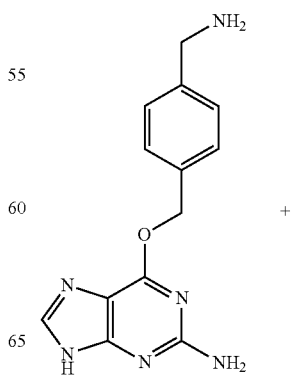

-continued

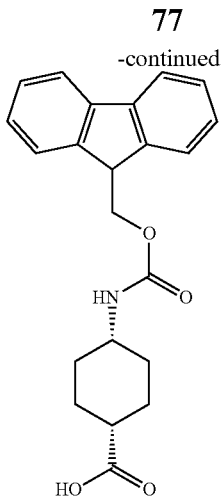

Compound 28:
benzylguanine-cis-4-aminocyclohexane

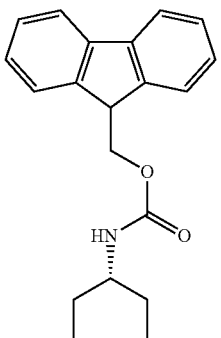
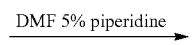

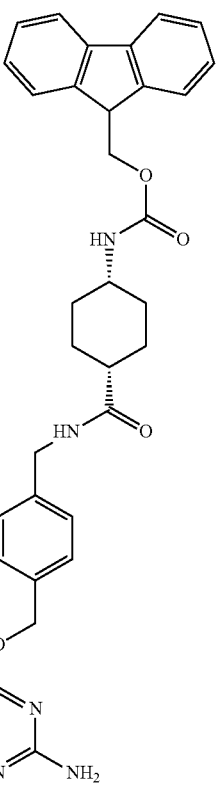
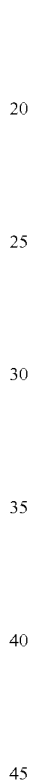

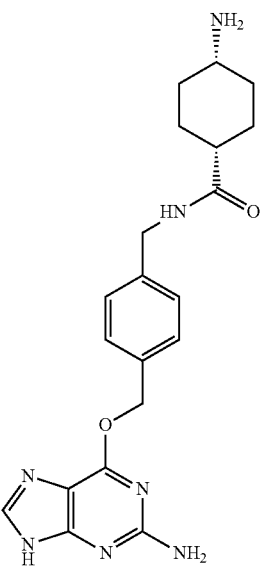

Weighed into a 50 ml round-bottomed flask were 61.3 mg (226 µmol) of 6-aminomethylbenzylguanine which was partially dissolved in 20 ml of anhydrous dimethylformamide. 82.7 mg (226 µmol) of cis-4-(Fmoc-amino)carboxycyclohexane and 72.8 mg (226 µmol) of TBTU were added. The reaction mixture was left stirring for two hours. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A white solid (28 mg, 20%) was obtained corresponding to the desired product.

MS (ES$^+$) m/z: [M+H$^+$] 618.6.

Weighed into a 1.5 ml Eppendorf tube were 0.7 mg (1.1 µmol) of benzylguanine-cis-4-(Fmoc-amino)cyclohexane which was dissolved in 190 µl of anhydrous dimethylformamide. 10 µl of piperidine were added and the reaction mixture was left stirring for one hour. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A white solid was obtained corresponding to the desired product. It was used directly in the following reaction without measuring the yield. MS (ES⁺) m/z: [M+H⁺] 396.3.
Compound 29:
DY647-cis-cyclohexane-benzylguanine
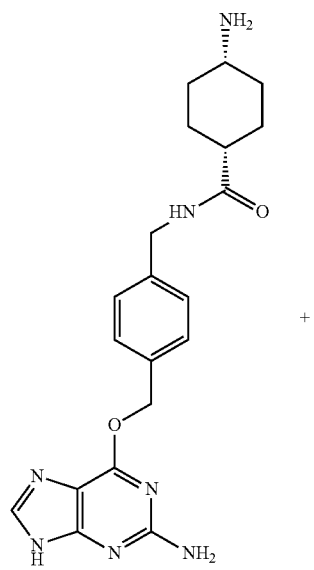
+
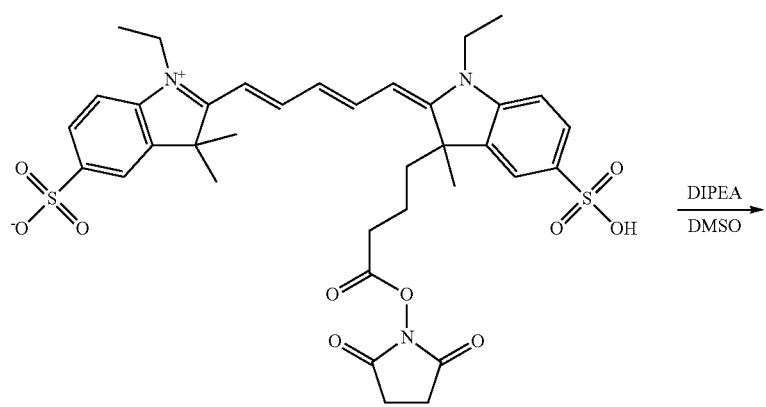

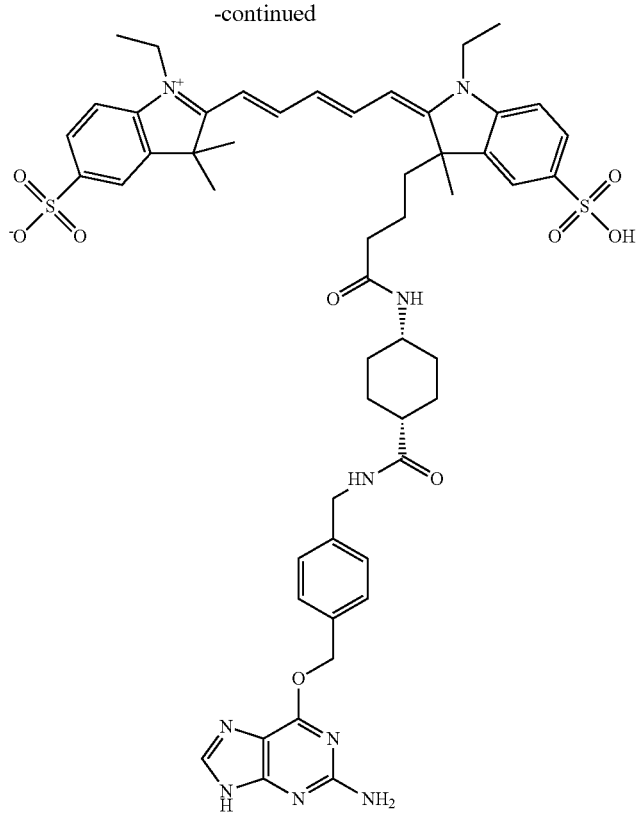

Added to a 25 ml round-bottomed flask containing 1 μmol of benzylguanine-cis-4-aminocyclohexane were 800 μl of anhydrous dimethylsulfoxide, 4 μl of diisopropylethylamine and 0.7 mg (1 μmol) of DY647-NHS. The reaction mixture was left stirring for one hour. The reaction was monitored by HPLC on a Merck Lichrospher RP °18, 5 μm, 125×4.6 column with a gradient of acetonitrile in water containing 0.2% of trifluoroacetic acid.

A purification by preparative HPLC was carried out on a Vydac C18, 10 μm, 250×22 column with a gradient of acetonitrile in water containing 0.2% of trifluoroacetic acid.

The fractions were collected and concentrated under reduced pressure. A blue solid was obtained (400 nmol by optical density measurement, 40%) corresponding to the desired product.

MS (ES$^+$) m/z: 1020.8.

Compound 30: Benzylcytosine-DY647

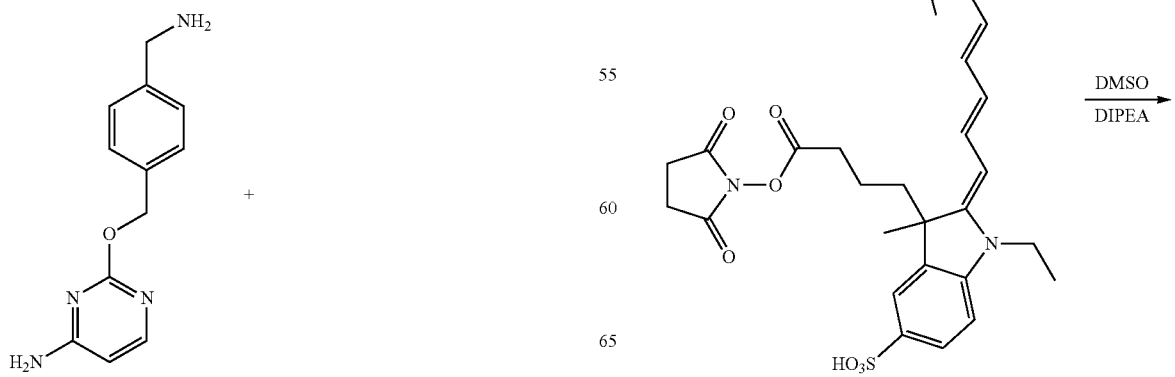

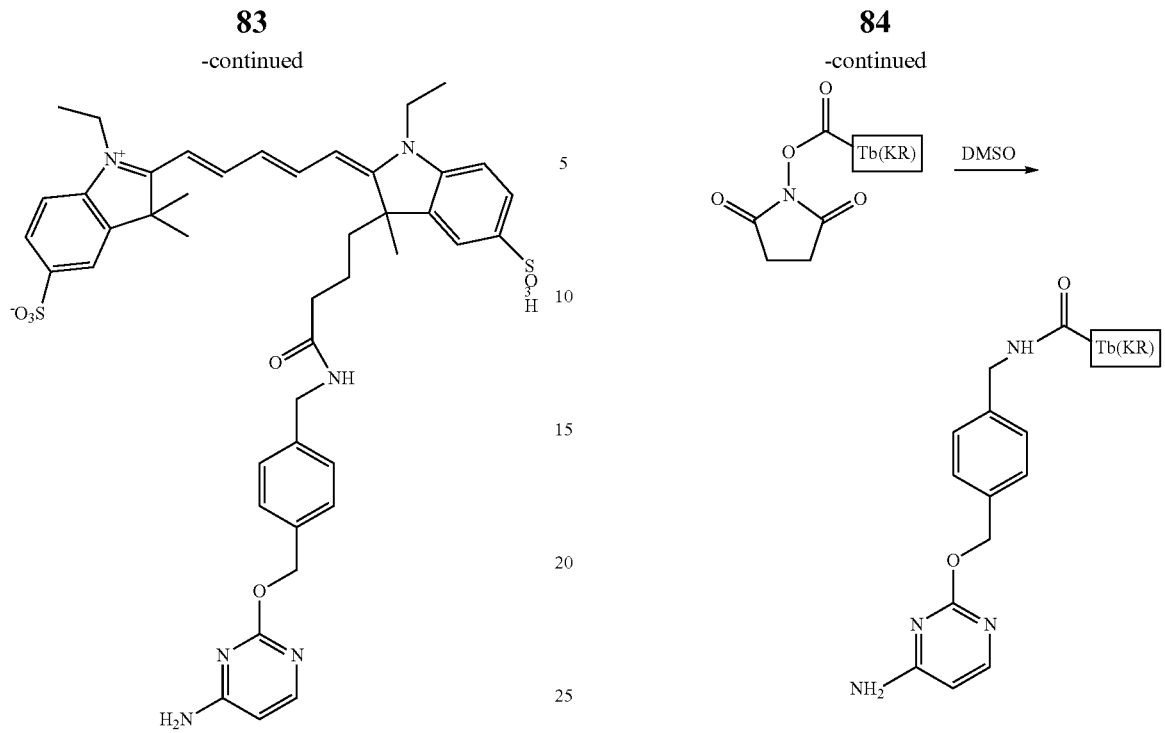

Added to a 1.5 ml Eppendorf tube were 1 μmol of aminomethylbenzylcytosine in solution in 26 μl of anhydrous dimethylsulfoxide, 1 μmol of DY647-NHS in solution in 76 μl of anhydrous dimethylsulfoxide and 4 μl of diisopropylethylamine.

The reaction mixture was stirred for one hour. The reaction was monitored by HPLC on a Merck Lichrospher RP °18, 5 μm, 125×4.6 column with a gradient of acetonitrile in water containing 0.2% of trifluoroacetic acid.

A purification by preparative HPLC was carried out on a Vydac C18, 10 μm, 250×22 column with a gradient of acetonitrile in water containing 0.2% of trifluoroacetic acid.

The fractions were collected and concentrated under reduced pressure. A blue solid was obtained (600 nmol by optical density measurement, 60%) corresponding to the desired product. MS (ES+) m/z: [M+H$^+$] 855.6 [M+Na+] 877.6.

Added to a 1.5 ml Eppendorf tube were 1 μmol of aminomethylbenzylcytosine in solution in 26 μl of anhydrous dimethylsulfoxide, 1 μmol of Tb(KR)-NHS in solution in 110 μl of anhydrous dimethylsulfoxide and 4 μl of diisopropylethylamine.

The reaction mixture was stirred for two hours. The reaction was monitored by HPLC on a Merck Lichrospher RP °18, 5 μm, 125×4.6 column with a gradient of acetonitrile in water containing 25 mM of triethylammonium acetate.

A purification by preparative HPLC was carried out on a Vydac C18, 10 μm, 250×22 column with a gradient of acetonitrile in water containing 25 mM of triethylammonium acetate.

The fractions were collected and concentrated under reduced pressure. A white solid was obtained (350 nmol by optical density measurement, 35%) corresponding to the desired product.

MS (ES+) m/z: [M+H$^+$] 1645.2 [M+2H+]/2 823.4.

Compound 31: Benzylcytosine-Tb(KR)

Compound 32: aminomethylbenzamide-BC

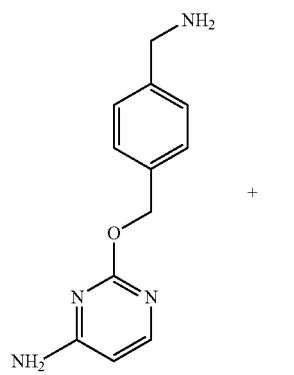

+

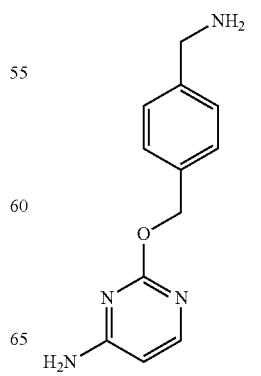

+

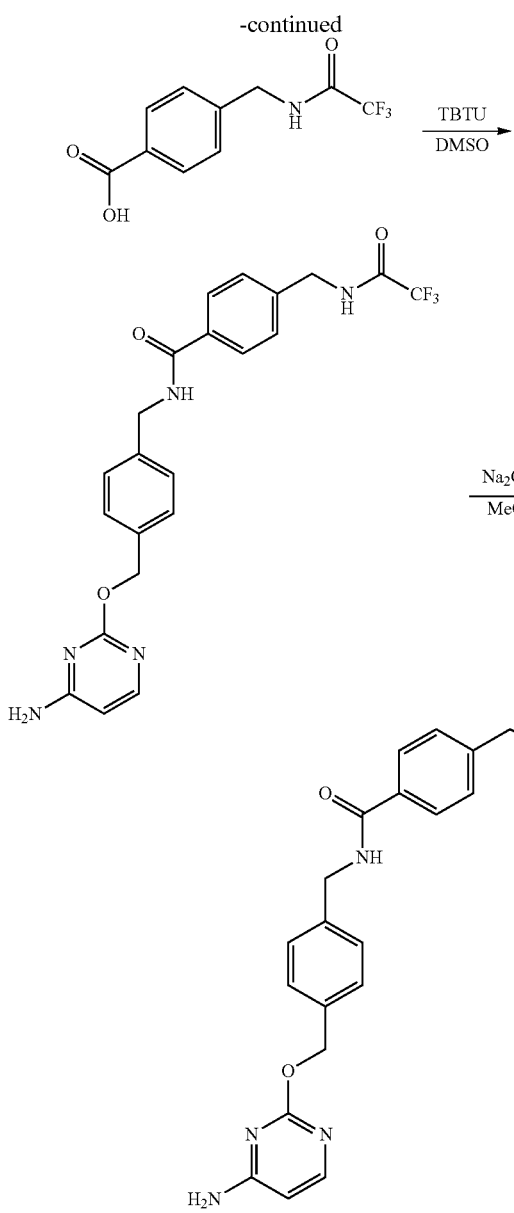

Weighed into a 2 ml Eppendorf tube were 6 mg (26 μmol) of aminomethylbenzylcytosine and 6.4 mg (26 μmol) of trifluoroacetamidomethylbenzoic acid. The mixture was dissolved in 600 μl of anhydrous dimethylsulfoxide and 9.2 mg (28.6 μmol) of TBTU and 8 μl of diisopropylethylamine were added. The reaction mixture was stirred for two hours. The reaction was monitored by HPLC on a Merck Lichrospher RP °18, 5 μm, 125×4.6 column with a gradient of acetonitrile in water containing 0.2% of trifluoroacetic acid.

A purification by preparative HPLC was carried out on a Vydac C18, 10 μm, 250×22 column with a gradient of acetonitrile in water containing 0.2% of trifluoroacetic acid.

The reaction mixture was evaporated to dryness under reduced pressure until a white solid was obtained. It was taken up in 2 ml of methanol, and 2 ml of an aqueous solution saturated with Na₂CO₃ and 4 ml of water were added. The mixture was stirred overnight. The deprotection was monitored by HPLC.

A purification by preparative HPLC was carried out on a Vydac C18, 10 μm, 250×22 column with a gradient of acetonitrile in water containing 0.2% of trifluoroacetic acid.

The fractions were collected and concentrated under reduced pressure. A white solid was obtained (8.5 μmol by optical density measurement, 32%) corresponding to the desired product. MS (ES+) m/z: [M+H⁺] 364.4.

Compound 33: DY647-methylbenzamide-BC

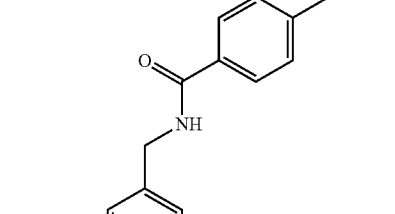

+

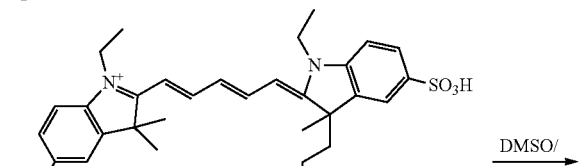

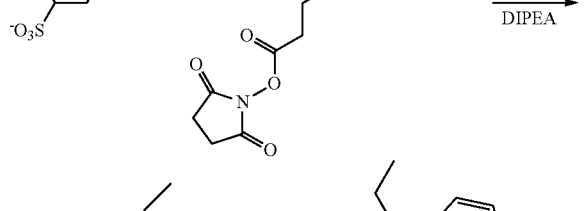

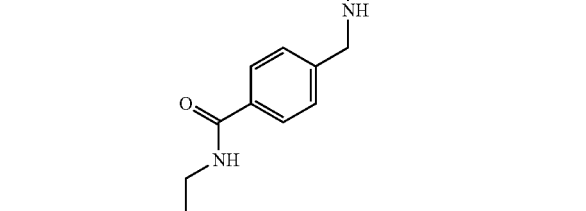

Added to a 1.5 ml Eppendorf tube containing 1 µmol of aminomethylbenzamide-BC were 1 µmol of DY647-NHS in solution in 140 µl of anhydrous dimethylsulfoxide and 4 µl of diisopropylethylamine.

The reaction mixture was stirred for one hour. The reaction was monitored by HPLC on a Merck Lichrospher RP °18, 5 µm, 125×4.6 column with a gradient of acetonitrile in water containing 0.2% of trifluoroacetic acid.

A purification by preparative HPLC was carried out on a Vydac C18, 10 µm, 250×22 column with a gradient of acetonitrile in water containing 0.2% of trifluoroacetic acid.

The fractions were collected and concentrated under reduced pressure. A blue solid was obtained (400 nmol by optical density measurement, 40%) corresponding to the desired product. MS (ES+) m/z: [M+H$^+$] 988.6 [M+Na+] 1010.6 [M+K+] 1026.6.

Compound 34: Tb(KR)-methylbenzamide-BC

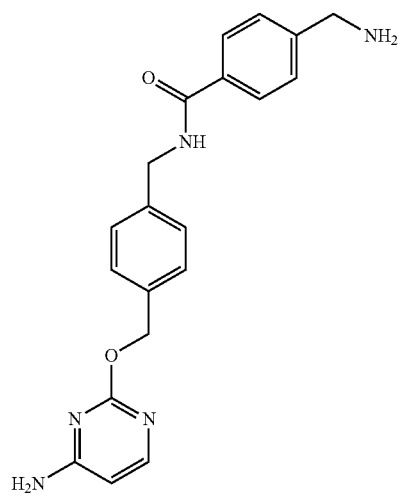

+

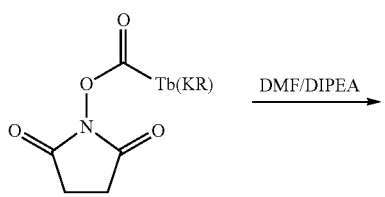 DMF/DIPEA

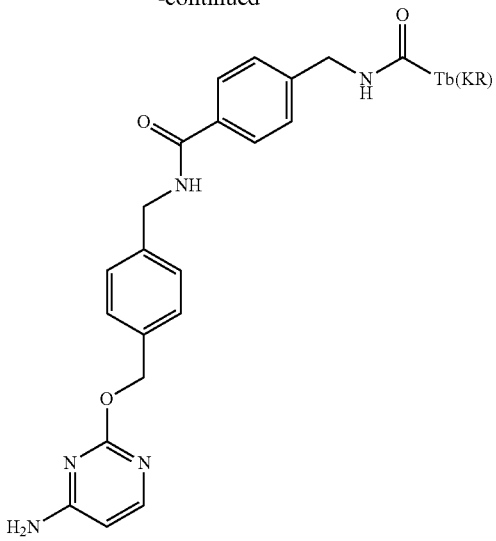

Added to a 1.5 ml Eppendorf tube containing 1 µmol of aminomethylbenzamide-BC were 1 µmol of Tb(KR)-NHS in solution in 120 µl of anhydrous dimethylsulfoxide and 4 µl of diisopropylethylamine.

The reaction mixture was stirred for one hour. The reaction was monitored by HPLC on a Merck Lichrospher RP °18, 5 µm, 125×4.6 column with a gradient of acetonitrile in water containing 25 mM of triethylammonium acetate.

A purification by preparative HPLC was carried out on a Vydac C18, 10 µm, 250×22 column with a gradient of acetonitrile in water containing 25 mM of triethylammonium acetate.

The fractions were collected and concentrated under reduced pressure. A white solid was obtained (270 nmol by optical density measurement, 27%) corresponding to the desired product. MS (ES+) m/z: [M+H$^+$] 1779.3 [M+2H+]/2 890.

Compound 35: Atto465-BG

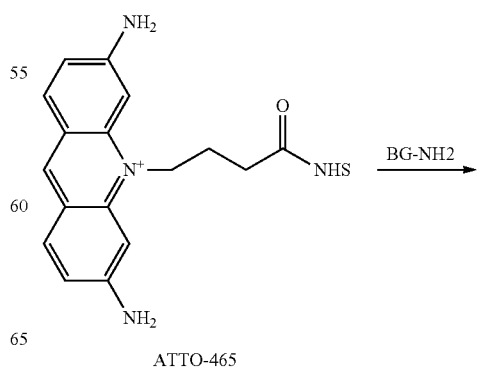

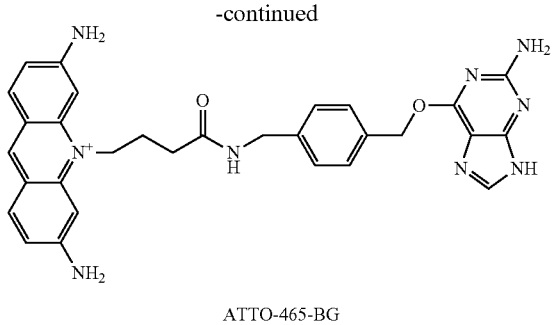

ATTO-465-BG

Introduced into a 1.5 ml Eppendorf tube were a solution of BG-NH$_2$ (0.3 µmol dissolved in 100 µl of anhydrous DMSO), a solution of ATTO-465-NHS (0.254 µmol dissolved in 100 µl of anhydrous DMSO), and also 3 µl of DIPEA. The reaction mixture was left stirring at ambient temperature for 1.5 hours. The reaction was monitored by HPLC on an Xbridge C18, 3.5 µm, 4.6×100 mm column with a gradient of acetonitrile in water containing 0.2% of trifluoroacetic acid.

A purification by preparative HPLC was carried out on an Xbridge C18, OBDTM, 19×100 mm column with a gradient of acetonitrile in water containing 0.2% of trifluoroacetic acid.

The fractions were collected and concentrated under reduced pressure. A yellowy-orange solid (0.128 µmol, 50% yield) was obtained corresponding to the desired product. MS (ES+) m/z: [M+H$^+$] 548.

Compound 36: Atto465-methylbenzamide-BG

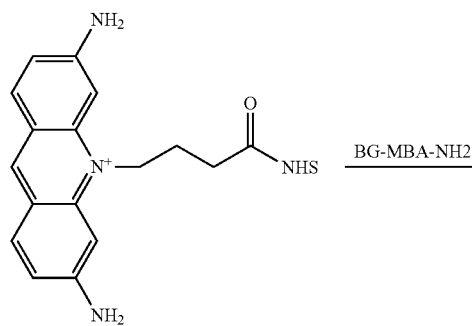

ATTO-465

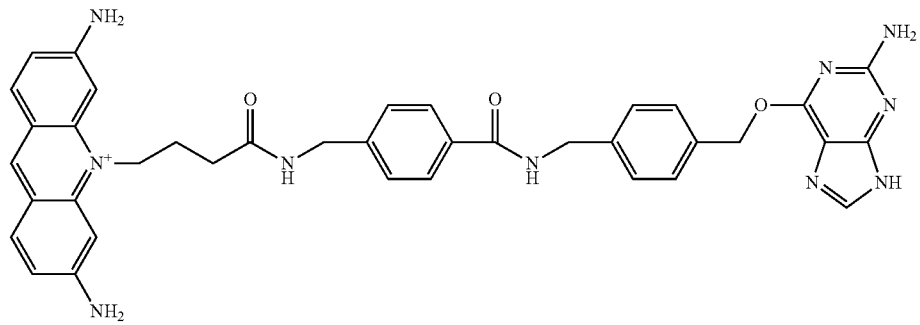 [SMILES: Nc1ccc2cc3ccc(N)cc3[n+](CCCC(=O)NCc3ccc(C(=O)NCc4ccc(COc5cc(N)nc6[nH]cnc56)cc4)cc3)c2c1]

ATTO-465-MBA-BG

Introduced into a 1.5 ml Eppendorf tube were a solution of BG-MBA-NH$_2$ (0.3 µmol of compound 8 dissolved in 100 µl of anhydrous DMSO), a solution of ATTO-465-NHS (0.254 µmol dissolved in 100 µl of anhydrous DMSO), and also 3 µl of DIPEA. The reaction mixture was left stirring at ambient temperature for 1.5 hours. The reaction was monitored by HPLC on an Xbridge C18, 3.5 µm, 4.6×100 mm column with a gradient of acetonitrile in water containing 0.2% of trifluoroacetic acid.

A purification by preparative HPLC was carried out on an Xbridge C18, OBDTM, 19×100 mm column with a gradient of acetonitrile in water containing 0.2% of trifluoroacetic acid.

The fractions were collected and concentrated under reduced pressure. A yellowy-orange solid (0.205 µmol, 80% yield) was obtained corresponding to the desired product. MS (ES+) m/z: [M+H$^+$] 681.

The invention claimed is:

1. A compound of formula (I'):

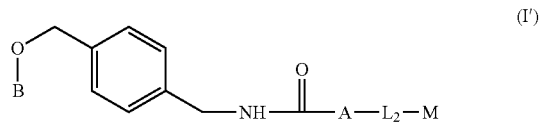

(I')

wherein:
B represents a group of formula (II') or (III') below:

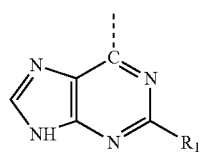
(II')

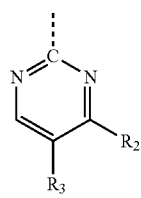
(III')

wherein the dotted lines represent the bonds with the oxygen of the formula (I'),
$R_1$ is selected from: H, $NH_2$, an OH group or an oxo group,
$R_2$ is selected from: $NH_2$, OH or oxo,
$R_3$ is selected from: H or a $CH_3$ group;
$L_2$ is a linker selected from;

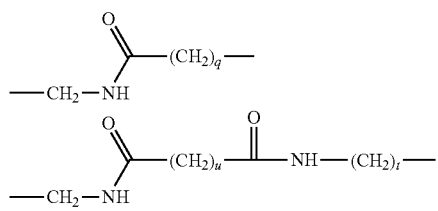

wherein q, u and t are integers between 1 and 10;
M is a label capable of generating or modulating a measurable signal, selected from a luminescent compound, a radioactive molecule, a member of a pair of binding partners, a molecule capable of interacting with other biological molecules, a molecule capable of bonding covalently or non-covalently with other molecules, a molecule capable of generating hydroxyl radicals when it is exposed to $H_2O_2$ and ascorbic acid, a molecule capable of generating reactive radicals after exposure to light, a molecule covalently bound to a solid support, a lipid or any other molecule capable of inserting itself into the plasma membrane, a biomolecule and a reactive group selected from an acrylamide, an amine, an ester, an aldehyde, an alkyl halide, an anhydride, an aniline, an azide, an aziridine, a carboxylic acid, a diazoalkane, a haloacetamide, a halotriazine, a hydrazine, an imido ester, an isocyanate, an isothiocyanate, a maleimide, a sulfonyl halide, a thiol, a ketone, an acid halide, an azidonitrophenyl, an azidophenyl, a 3-(2-pyridyldithio)-propionamide, and glyoxal; and
A is selected from the following divalent groups:

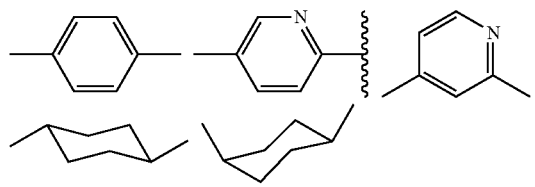

2. The compound of claim 1, wherein B is a group of formula (II') and $R_1$ is an $NH_2$ group.

3. The compound of claim 1, wherein B is a group of formula (III'), $R_2$ is an $NH_2$ group and $R_3$ is H.

4. The compound of claim 1, wherein M is a label capable of generating or modulating a measurable signal.

5. The compound of claim 1, wherein M is selected from a luminescent compound, a radioactive molecule, a member of a pair of binding partners, a molecule capable of interacting with other biological molecules, a molecule capable of bonding covalently or non-covalently with other molecules, a molecule capable of generating hydroxyl radicals when it is exposed to $H_2O_2$ and ascorbic acid, a molecule capable of generating reactive radicals after exposure to light, a molecule covalently bound to a solid support, a lipid or any other molecule capable of inserting itself into the plasma membrane, and a biomolecule.

6. The compound of claim 1, wherein M is avidin, streptavidin, or biotin.

7. The compound of claim 1, wherein M is an organic fluorophore, a protein fluorophore or a fluorescent lanthanide complex.

8. The compound of claim 1, wherein M is selected from

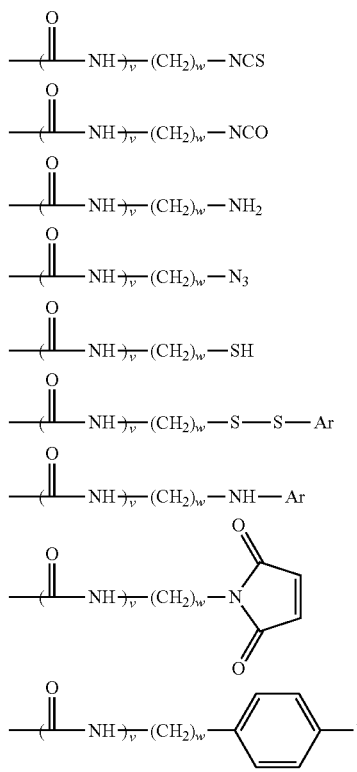

-continued

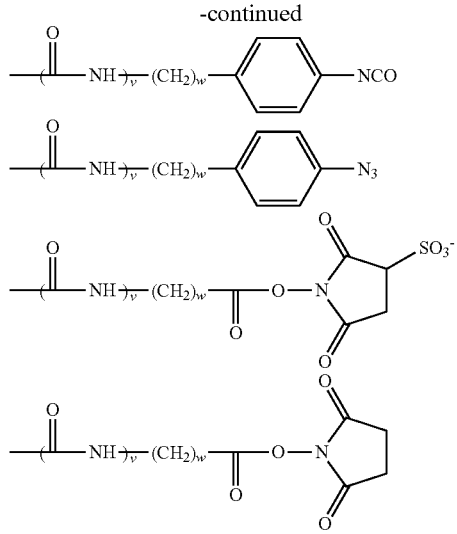

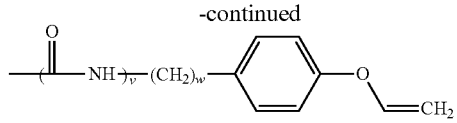

wherein w is an integer from 0 to 8, v is 0 or 1, and Ar is a saturated or unsaturated heterocycle having 5 or 6 ring members, comprising 1 to 3 heteroatoms, optionally substituted by a halogen atom.

9. The compound of claim 1, wherein M is a reactive group selected from a carboxylic acid, an amine, a succinimidyl ester of carboxylic acid, a haloacetamide, a hydrazine, an isothiocyanate, and a maleimide group.

10. The compound of claim 1, which corresponds to one of the following formulae:

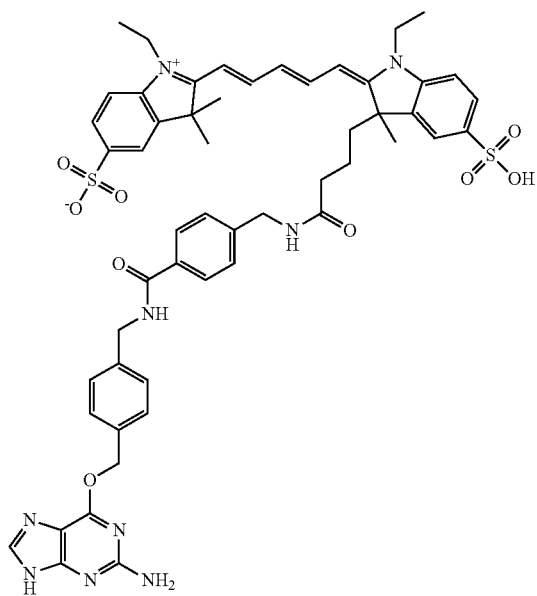

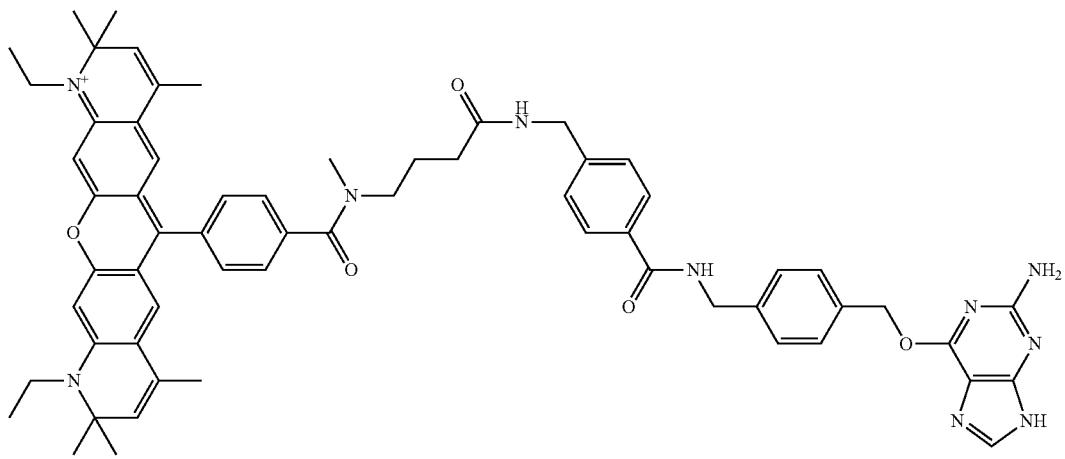

95 96
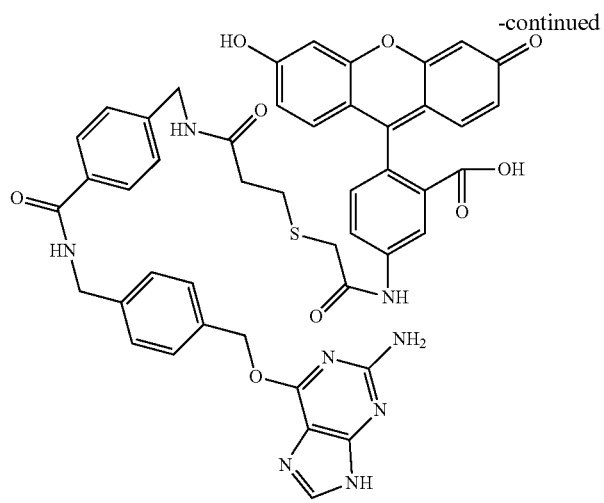
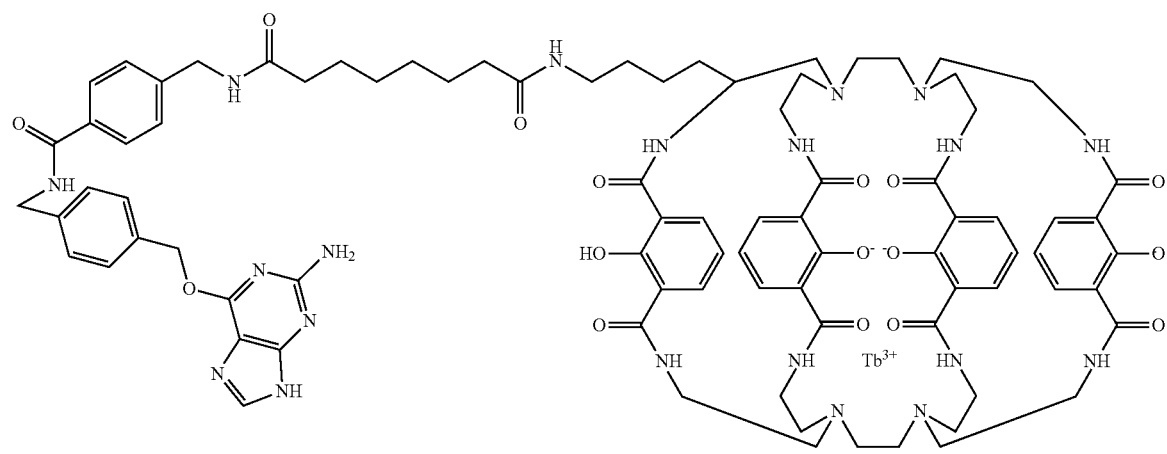
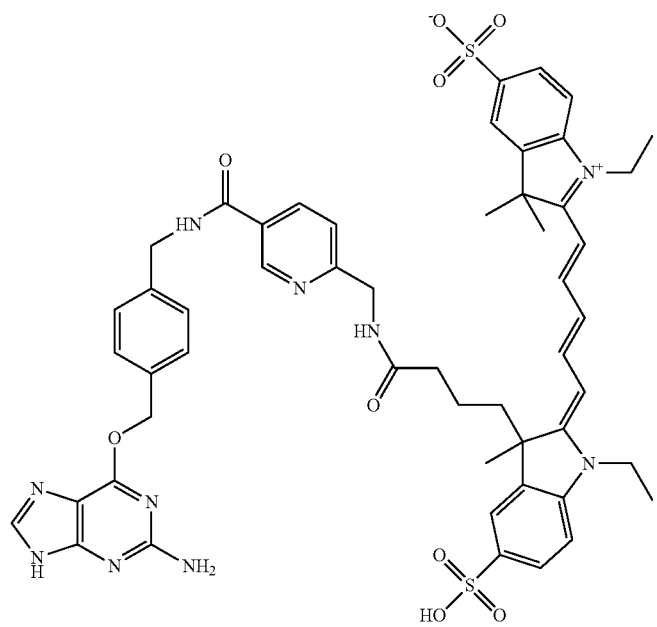

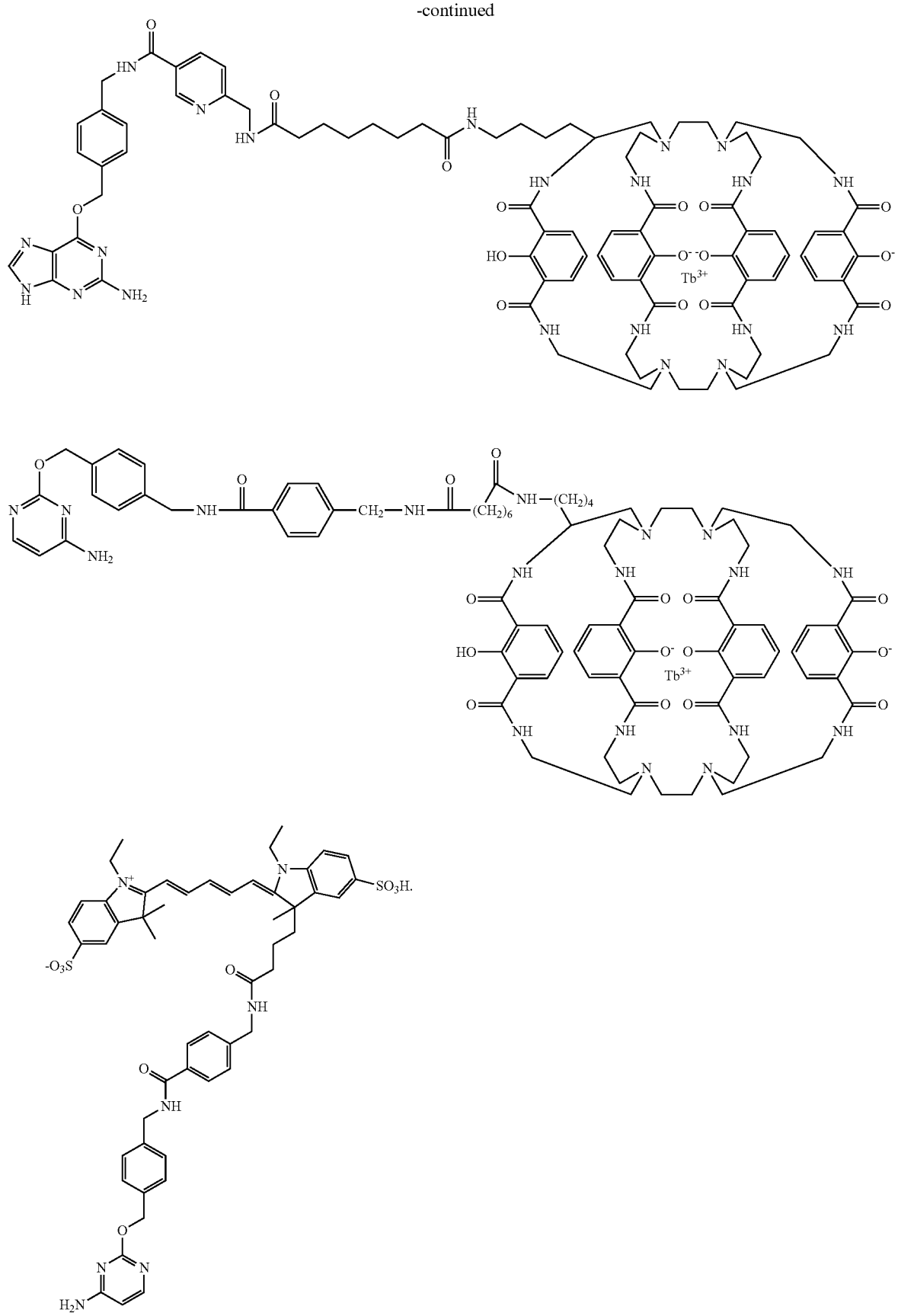

11. The compound of claim 1, which corresponds to one of the following formulae:

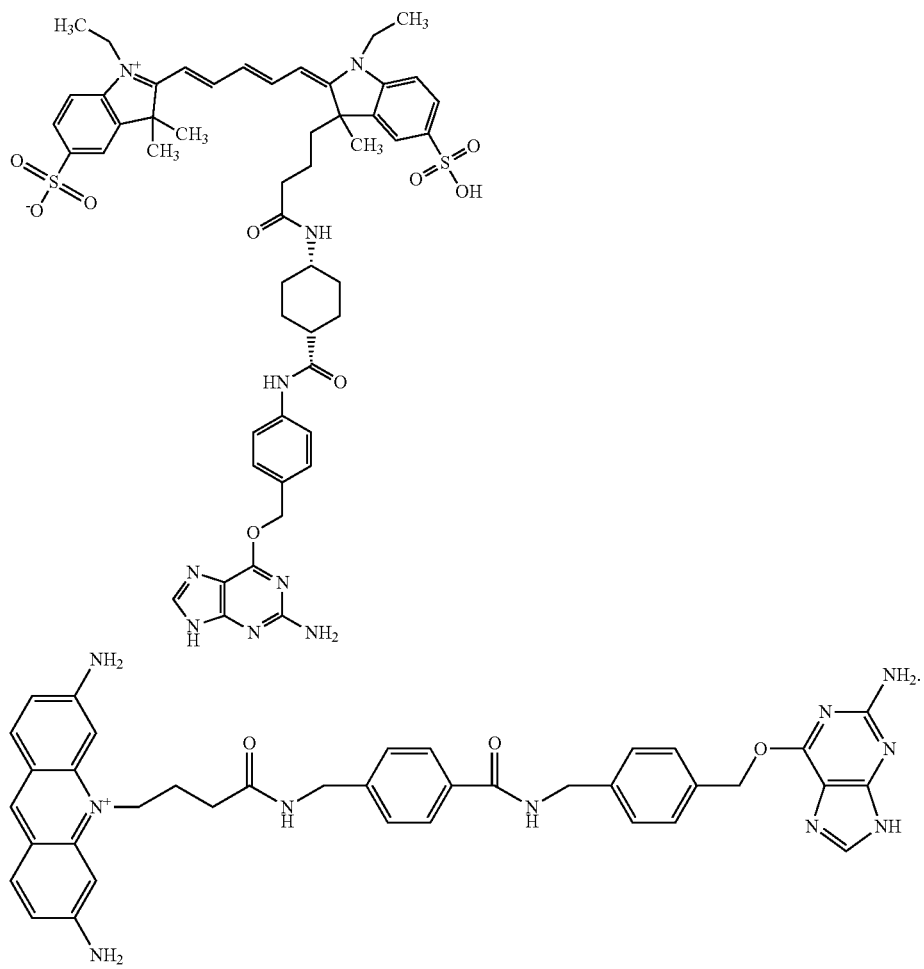

12. A method of labeling a protein of interest with a group M, said protein of interest being expressed in the form of a fusion protein with an AGT enzyme, which comprises a step of bringing said fusion protein into contact with a compound of claim 1.

13. The compound of claim 7, wherein the organic fluorophore is selected from cyanines and derivatives thereof, fluorescein and derivatives thereof, coumarin and derivatives thereof, rhodamine and derivatives thereof, carbopyronine and derivatives thereof, oxazine and derivatives thereof, AlexaFluors, Crystal Violet and derivatives thereof, perylene bisimides and derivatives thereof, squaraines, bore-dipyromethenes (BODIPYs), NBD (nitrobenzoxadiazole) and derivatives thereof, and DABCYL (4-((4-(dimethylamino) phenyl)azo)benzoic acid) and derivatives thereof.

14. The compound of claim 7, wherein the protein fluorophore is selected from GFP and variants thereof, fluorescent proteins extracted from corals, and phycobiliproteins.

15. The compound of claim 14, wherein the phycobiliprotein is selected from B-phycoerythrin, R-phycoerythrin, C-phycocyanin, and allophycocyanins.

16. The compound of claim 7, wherein the fluorescent lanthanide complex is a lanthanide cryptate or a lanthanide chelate.

17. The compound of claim 16, wherein the fluorescent lanthanide complex is a chelate or cryptate of europium, terbium, samarium, dysprosium, or neodymium.

* * * * *